United States Patent
Akiyama et al.

(10) Patent No.: US 8,778,490 B2
(45) Date of Patent: Jul. 15, 2014

(54) ABSORBENT COMPOSITE MATERIAL COMPRISING WATER-ABSORBENT RESIN PARTICLES HAVING SPECIFIC SURFACE STRENGTH, AND METHOD FOR MANUFACTURING THE SAME

(75) Inventors: Tsutomu Akiyama, Tokyo (JP); Tamotsu Kodama, Tokyo (JP); Masataka Nishi, Tokyo (JP); Hiroshige Okamoto, Tokyo (JP)

(73) Assignee: Asahi Kasei Chemicals Corporation, Tokyo (JP)

(*) Notice: Subject to any disclaimer, the term of this patent is extended or adjusted under 35 U.S.C. 154(b) by 1464 days.

(21) Appl. No.: 11/920,232

(22) PCT Filed: May 12, 2006

(86) PCT No.: PCT/JP2006/309536
§ 371 (c)(1),
(2), (4) Date: Dec. 8, 2008

(87) PCT Pub. No.: WO2006/121148
PCT Pub. Date: Nov. 16, 2006

(65) Prior Publication Data
US 2009/0177174 A1    Jul. 9, 2009

(30) Foreign Application Priority Data

May 13, 2005 (JP) .................. 2005-141371
May 18, 2005 (JP) .................. 2005-144837
Sep. 27, 2005 (JP) .................. 2005-279976

(51) Int. Cl.
*B32B 5/16* (2006.01)
*A61F 13/53* (2006.01)
*A61F 13/15* (2006.01)
*A61F 13/537* (2006.01)

(52) U.S. Cl.
CPC ........... *A61F 13/15617* (2013.01); *A61F 13/53* (2013.01); *A61F 13/53743* (2013.01)
USPC ............................. 428/327; 604/361; 604/372

(58) Field of Classification Search
USPC .................. 428/403, 407, 327; 604/367, 372
See application file for complete search history.

(56) References Cited

U.S. PATENT DOCUMENTS

| 4,260,443 | A | 4/1981 | Lindsay et al. |
| 4,654,039 | A | 3/1987 | Brandt et al. |

(Continued)

FOREIGN PATENT DOCUMENTS

| EP | 0 164 743 | 12/1985 |
| EP | 0 359 615 | 3/1990 |

(Continued)

OTHER PUBLICATIONS

European Search Report issued Apr. 3, 2009 in corresponding European Patent Appiication 06746333.1.

(Continued)

*Primary Examiner* — Hoa (Holly) Le
(74) *Attorney, Agent, or Firm* — Staas & Halsey LLP

(57) ABSTRACT

An absorbent composite comprising: a base material and water-absorbent resin particles; wherein the following conditions (1) to (4) are fulfilled: (1) the weight ratio of water-absorbent resin relative to the total weight of the base material and water-absorbent resin is 65 to 99 wt %, (2) the water-absorbent resin particles adhering directly to the base material constitute 50 wt % or more of the total water-absorbent resin particles; (3) the average absorption capacity of the water-absorbent resin particles is 50 g/g or more; and (4) the amount of residual monomers in the water-absorbent resin is 200 ppm or less.

25 Claims, 24 Drawing Sheets

(56) References Cited

U.S. PATENT DOCUMENTS

| | | | |
|---|---|---|---|
| 4,721,647 A | 1/1988 | Nakanishi et al. | |
| 4,851,069 A | 7/1989 | Packard et al. | |
| 5,061,259 A | 10/1991 | Goldman et al. | |
| 5,075,344 A | 12/1991 | Johnson | |
| 5,373,066 A | 12/1994 | Rebre et al. | |
| 5,451,613 A | 9/1995 | Smith et al. | |
| 5,494,622 A | 2/1996 | Heath et al. | |
| 5,560,878 A * | 10/1996 | Dragoo et al. | 264/115 |
| 5,599,335 A * | 2/1997 | Goldman et al. | 604/368 |
| 5,601,542 A | 2/1997 | Melius et al. | |
| 5,651,862 A | 7/1997 | Anderson et al. | |
| 5,795,344 A | 8/1998 | Chappell | |
| 5,866,678 A | 2/1999 | Kajikawa et al. | |
| 5,919,178 A | 7/1999 | Widlund | |
| 5,977,014 A | 11/1999 | Plischke et al. | |
| 5,985,944 A * | 11/1999 | Ishizaki et al. | 521/64 |
| 5,993,433 A | 11/1999 | St. Louis et al. | |
| 6,187,872 B1 | 2/2001 | Yanase et al. | |
| 6,388,000 B1 | 5/2002 | Irie et al. | |
| 6,590,136 B1 * | 7/2003 | Young et al. | 604/369 |
| 7,435,477 B2 * | 10/2008 | Adachi et al. | 428/407 |
| 8,163,124 B2 | 4/2012 | Moriura et al. | |
| 8,563,127 B2 * | 10/2013 | Akiyama et al. | 428/327 |
| 2003/0181115 A1 | 9/2003 | Nagasuna et al. | |
| 2003/0205318 A1 | 11/2003 | Ko et al. | |
| 2004/0214946 A1 | 10/2004 | Smith et al. | |
| 2005/0096623 A1 | 5/2005 | Nhan et al. | |
| 2005/0221980 A1 * | 10/2005 | Adachi et al. | 502/402 |
| 2006/0128827 A1 * | 6/2006 | Matsumoto et al. | 522/150 |
| 2006/0160455 A1 | 7/2006 | Sugyo et al. | |
| 2006/0276598 A1 * | 12/2006 | Wada et al. | 525/330.3 |
| 2007/0093766 A1 | 4/2007 | Yoshino et al. | |
| 2008/0119626 A1 * | 5/2008 | Fujimaru et al. | 526/317.1 |
| 2009/0169891 A1 * | 7/2009 | Higashimoto et al. | 428/402 |
| 2009/0177174 A1 | 7/2009 | Akiyama et al. | |
| 2010/0062165 A1 | 3/2010 | Suzuki et al. | |
| 2010/0062934 A1 | 3/2010 | Suzuki et al. | |
| 2010/0063470 A1 | 3/2010 | Suzuki et al. | |
| 2011/0204289 A1 * | 8/2011 | Higashimoto et al. | 252/194 |
| 2012/0108421 A1 * | 5/2012 | Akiyama et al. | 502/402 |

FOREIGN PATENT DOCUMENTS

| | | |
|---|---|---|
| EP | 0 695 541 | 2/1996 |
| EP | 1 142 696 | 10/2001 |
| EP | 1 364 985 | 11/2003 |
| EP | 1 621 165 | 2/2006 |
| JP | 61-62463 | 3/1986 |
| JP | 5-31362 | 2/1993 |
| JP | 5-230747 | 9/1993 |
| JP | 6-370 | 1/1994 |
| JP | 6-57010 | 3/1994 |
| JP | 6-218007 | 8/1994 |
| JP | 6-287886 | 10/1994 |
| JP | 7-132126 | 5/1995 |
| JP | 7-184956 | 7/1995 |
| JP | 9-156013 | 6/1997 |
| JP | 9-239912 | 9/1997 |
| JP | 10-118114 | 5/1998 |
| JP | 10-118115 | 5/1998 |
| JP | 10-508521 | 8/1998 |
| JP | 10-508528 | 8/1998 |
| JP | 10-510447 | 10/1998 |
| JP | 10-512183 | 11/1998 |
| JP | 2904791 | 3/1999 |
| JP | 11-137600 | 5/1999 |
| JP | 2000-238161 | 9/2000 |
| JP | 2001-96654 | 4/2001 |
| JP | 2001-171027 | 6/2001 |
| JP | 2001-252307 | 9/2001 |
| JP | 2002-165837 | 6/2002 |
| JP | 2002-361079 | 12/2002 |
| JP | 2002-370025 | 12/2002 |
| JP | 2003-11118 | 1/2003 |
| JP | 2003-290290 | 10/2003 |
| JP | 2004-001355 | 1/2004 |
| JP | 2004-049380 | 2/2004 |
| JP | 2004-124303 | 4/2004 |
| JP | 2004-313580 | 11/2004 |
| JP | 2004-358797 | 12/2004 |
| JP | PL 365287 | 12/2004 |
| JP | 2005-13724 | 1/2005 |
| JP | 2005-200630 | 7/2005 |
| RU | 2 186 797 C2 | 8/2002 |
| RU | 2 197 213 C2 | 1/2003 |
| RU | 2 203 010 C2 | 4/2003 |
| RU | 2 222 303 C2 | 1/2004 |
| WO | 96/07476 | 3/1996 |
| WO | 96/16624 | 6/1996 |
| WO | 96/17573 | 6/1996 |
| WO | 98/37149 | 8/1998 |
| WO | 00/10499 | 3/2000 |
| WO | 01/34082 | 5/2001 |
| WO | 01/64153 | 9/2001 |
| WO | 02/053605 | 7/2002 |
| WO | 03/030955 | 4/2003 |
| WO | 2004/108274 | 12/2004 |
| WO | 2004/110328 | 12/2004 |
| WO | 2005/011548 | 2/2005 |

OTHER PUBLICATIONS

*Modern Superabsorbent Polymer Technology*, Edited by Fredric L. Buchholz and Andrew T. Graham, Wiley-VCH, 1998, pp. 19, 69-74, 95-103 and 158-159.

U.S. Office Action for co-pending U.S. Appl. No. 13/317,645, mailed Sep. 10, 2012.

U.S. Office Action for co-pending U.S. Appl. No. 13/317,647, mailed Mar. 11, 2013.

U.S. Office Action for copending U.S. Appl. No. 13/317,647, issued Sep. 25, 2013, 13 pages.

* cited by examiner

FIG.13
A    B    C    D    E
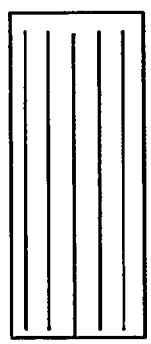 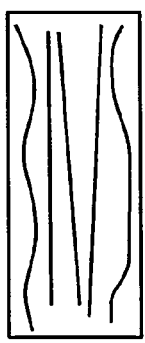  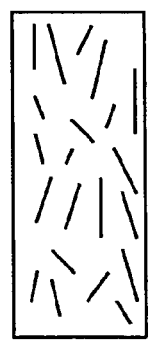 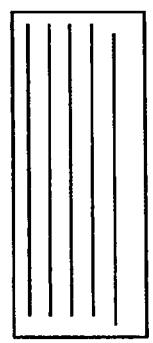
F    G    H    I
 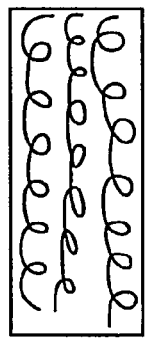 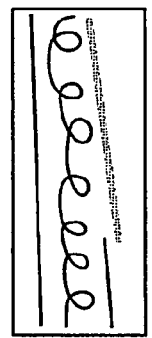 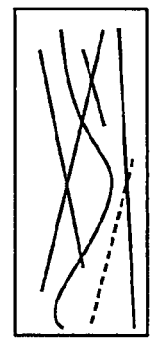

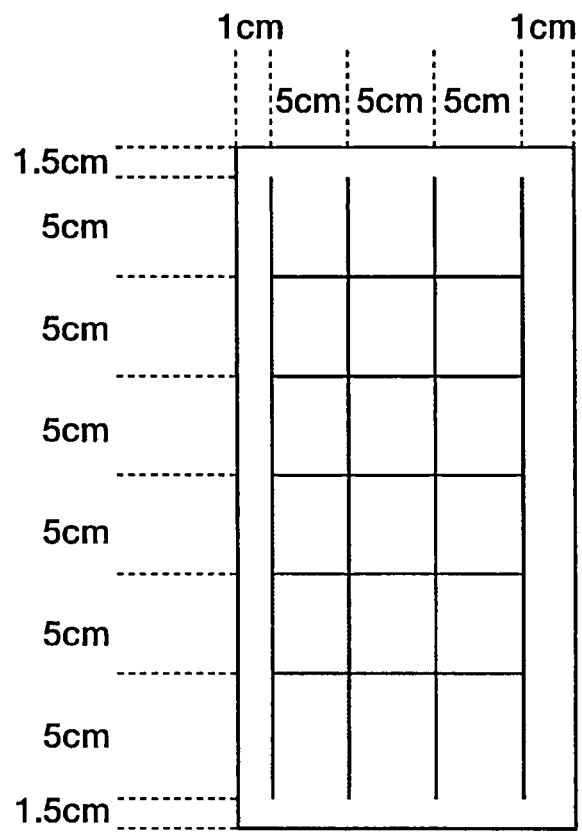
FIG.22
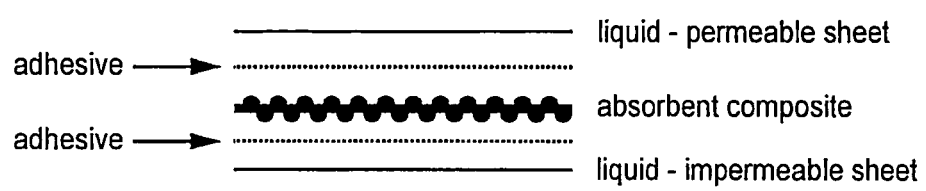

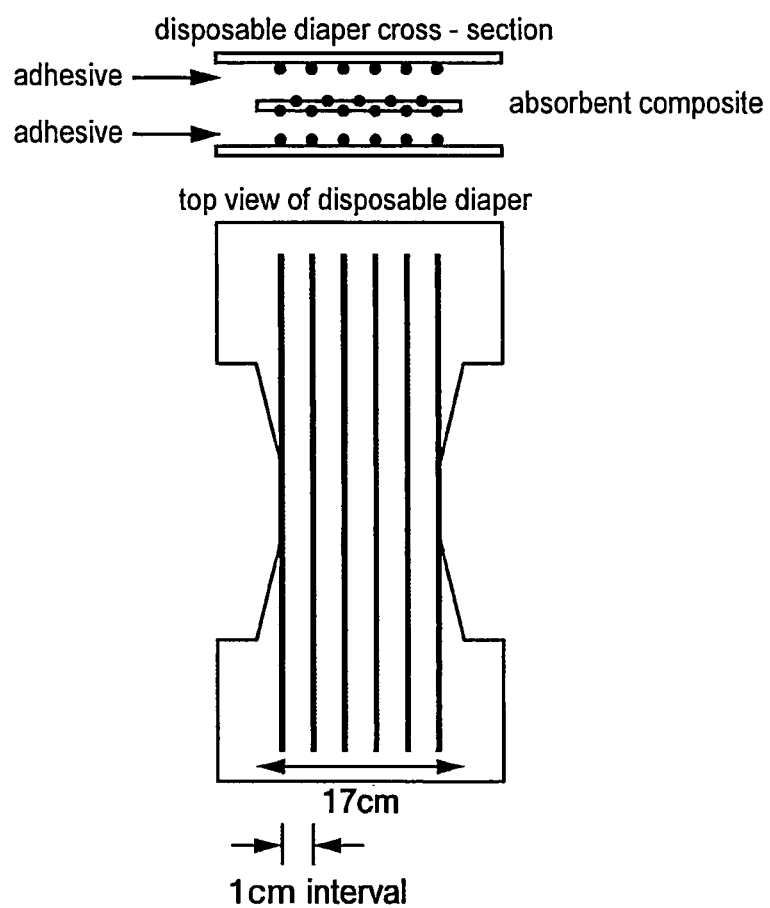

ABSORBENT COMPOSITE MATERIAL COMPRISING WATER-ABSORBENT RESIN PARTICLES HAVING SPECIFIC SURFACE STRENGTH, AND METHOD FOR MANUFACTURING THE SAME

CROSS REFERENCE TO RELATED APPLICATIONS

This application claims the benefit under 35 U.S.C. Section 371, of PCT International Application Number PCT/JP2006/309536, filed May 12, 2006 and Japanese Application Nos. 2005-141371 filed May 13, 2005; 2005-144837 filed May 18, 2005 and 2005-279976 filed Sep. 27, 2005; in Japan, the contents of which are incorporated herein by reference.

TECHNICAL FIELD

The present invention relates to a thin, lightweight sheet-shaped absorber, and to a method for manufacturing the same. Because this absorber is an absorbent composite with excellent water-absorbing capability, absorption speed and high-dispersion properties, it is suitable for use in hygiene products such as disposable diapers and sanitary napkins. The present invention also relates to an environmentally-friendly absorber which is capable of reducing the amount of pulp, water-absorbent resin and the like commonly used in sanitary materials.

BACKGROUND ART

Disposable diapers, sanitary napkins and other sanitary materials have an absorber body for absorbing bodily fluids and other liquids, a soft, liquid-permeable top sheet on the side that contacts the body, and a liquid-impermeable back sheet on the side away from the body. The absorber is normally made from a mixture of pulp or another fibrous substance and a water-absorbent resin.

There has been increasing demand in recent years for thinner, more lightweight sanitary materials to resolve problems of design, distribution, garbage disposal and the like. The most common method currently used to meet these demands in sanitary materials is to reduce the amount of fiber or other support material for the water-absorbent resin in the sanitary material and use larger amounts of water-absorbent resin. Such sanitary materials having a smaller proportion of hydrophilic fiber and a higher proportion of water-absorbent resin may be better at simply storing liquid, but are not necessarily good at distributing and dispersing the liquid when the diaper is actually used. That is, the large amount of water-absorbent resin turns into a soft gel when it absorbs liquid, resulting in a phenomenon called gel blocking which greatly inhibits dispersal of the liquid. Once gel blocking occurs the resin no longer performs properly, and not only does it absorb less water but absorption speed decreases.

The proportions of hydrophilic fiber and water-absorbent resin must both be restricted in order to avoid this problem and maintain the absorbent properties of the absorber, so there are limits on reducing the hydrophilic fiber and reducing the thickness of the sanitary material. Moreover, pulp is most commonly used as the fiber in sanitary materials, especially virgin pulp is normally used because of its cleanliness, therefore the use of large quantities of fiber increase of burdens on forest resources.

Methods that have been proposed for preventing the gel blocking that occurs when amount of fiber is reduced and large amounts of water-absorbent resin are used include a method using two different water-absorbent resins with different absorption abilities (see for example Patent Document 1), a method using a composition containing a cationic ion-exchange hydrogel-forming polymer and an anionic ion-exchange hydrogel-forming polymer (see for example Patent Document 2) a method using a water-absorbent resin crosslink density on the surface of which is high (see for example Patent Document 3), a method using a water-absorbent resin the salt density of which near the surface is lower than the overall salt density (see for example Patent Document 32), and a method extruding and foaming a mixture of a water-absorbent resin and a thermoplastic resin into a sheet (see for example Patent Document 4). However, these suffer from such problems as high cost and inadequate absorption properties for use in an absorber with a high water-absorbent resin concentration. Moreover, because these methods reduce the relative amount of hydrophilic fiber, which serves to hold the water-absorbent resin, the particles of absorbent resin tend to become unevenly distributed before use or to move around during use. The absorbent product loses its shape when the water-absorbent resin shifts from its intended position in this way, and the excreted urine or other liquid does not contact the water-absorbent resin in the absorbent product, resulting in leakage.

In another method, the method of mixing the fiber and water-absorbent resin is fine-tuned so as to prevent uneven distribution and blocking of one part of the water-absorbent resin by another part (see for example Patent Document 5). In this method, the degree of mixing is high because the water-absorbent resin and pulp are first mixed in water and then dry mixed with hydrophilic fiber and formed into a web with air. However, the problem is that the water-absorbent resin may clog the web during the process of air formation. Once this occurs, it becomes necessary to remove it from the drum, decreases productivity. It is also preferable to use a relatively hard absorbent resin in order to prevent clogging and facilitate removing when clogging occurs. In general, hard water-absorbent resins tend to have low absorption capacity, making it necessary to use a large quantity of water-absorbent resin in order to absorb the target amount of liquid. This method is also unsatisfactory in terms of preventing movement and uneven distribution of the water-absorbent resin in the product.

In order to resolve these problems, particularly the problem of movement and uneven distribution of the water-absorbent resin, methods of bonding the water-absorbent resin onto a support have been studied. Examples include a method of embossing an absorber, a method in which a thermoplastic binder fiber is included in an absorber comprising a water-absorbent resin and hydrophilic fiber, and the absorbent body is then thermally fused, a method in which a synthetic resin with high recovery from deformation is included in an absorbent body comprising a water-absorbent resin and hydrophilic fiber, and the absorbent body is then thermally fused (see for example Patent Documents 6 and 7), a method in which the surface of a water-absorbent resin having anionic groups is coated with a cationic polymer, so that the particles adhere and are fixed to one another as the resin swells (see for example Patent Document 8 and 9), a method of using an emulsion binder to fix the water-absorbent resin and hydrophilic fiber, and a method of using a hot melt adhesive to fix the water-absorbent resin to a base material (see for example Patent Document 10 and 11) and the like. Because in such examples the particles of water-absorbent resin are stacked on each other on the support so as to increase the proportion of water-absorbent resin, the blocking effect is greater and a large quantity of binder must be used. When a large quantity of binder is used to fix the water-absorbent resin on the base material in this way, moreover, the binding force itself may restrict the swelling of the water-absorbent resin. In particular, the inherent absorbent abilities of the water-absorbent resin may not be fully exploited if the water-absorbent resin, hydrophilic fiber and the like are fixed with a thermoplastic binder or emulsion.

Techniques for reducing restrictions on the swelling of the water-absorbent resin when it is fixed on a support include a water absorbable composite material comprising a water-absorbent resin part of which is held within a bulky nonwoven fabric, while the exposed surface of the resin is coated with fine cellulose fiber and the outer surface of the composite is covered with a fibrillated hot melt (see for example Patent Document 12) and an absorbent composite sheet comprising a water-absorbent resin part of which is held within a bulky nonwoven fabric and part of which is exposed on the surface, wherein the outer surface of the resin is coated with a fiber net-like double hot melt layer consisting of two layers with different sized mesh (see for example Patent Document 13). However, although swelling is less restricted with these methods, the absorption properties are affected by the fixing process. As has already been shown, the absorption properties of water-absorbent resin include not only the absorption capacity, absorption speed, absorption capacity under pressure, dispersion-absorption capacity under pressure and liquid permeability of the swollen gel, but also the capillary absorption factor, which is an absorption property based on the capillary force in the gaps between particles (see for example Patent Document 14 and 15). It has been shown that this capillary absorption capacity and other absorption properties of water-absorbent resin are greatly affected by conventional fixing means. That is, even using highly functional water-absorbent resins the absorption properties of absorbent bodies obtained by fixing those resins often have not reflected the inherent absorption properties of the water-absorbent resins. It has also been said that it is not necessary to insist so much on the performance of the water-absorbent resin as long as it fulfills a minimum performance requirement (see for example Patent Document 16), and differences in the absorption properties of water-absorbent resin have in fact been hard to distinguish when the resin is made into an absorbent body, making it hard to differentiate absorbent bodies.

In some cases, an adhesive has been used to bond an absorbent gel to a chemically strengthened cellulose fiber (see for example Patent Document 17). In this method the chemically strengthened cellulose fiber ensures a space for swelling of the absorbent gel, effectively separating the water-absorbent resin particles and allowing the resin to function more easily. However, the fibers are not fixed to each other, and the fiber inevitably moves inside the absorbent body, resulting in a corresponding movement of the absorbent gel. Also, large quantities of cellulose need to be used because the absorbent gel must be enveloped in cellulose fiber to ensure space for swelling, and the swelling space itself is not adequate. A large quantity of adhesive must also be used, which inevitably restricts swelling. Adhesion has also been accomplished using a base material and a crosslinking agent (see for example Patent Document 18). In this method, it appears that an absorbent composite with good liquid permeability has been obtained by using a crosslinking agent which does not restrict swelling of the gel, along with a low weight of particles to prevent gel blocking. However, a crosslinking agent is required for adhesion, and the absorption capacity of the particles could be reduced when some of them are crosslinked. Moreover, it is also said that performance under load is improved when the degree of surface crosslinking is increased, but in this case the blocking prevention effect would not be adequate. In addition, the absorption capacity of the composite is low because a low weight of particles is used.

In some cases, a water-absorbent resin has also been fixed to a base material without using a binder. In one method, absorbent polymer particles are bonded to a fibrous base material during polymerization, and polymerization is performed on the fibrous base material (see for example Patent Document 19). In this method, the fibrous base material penetrates between the polymer particles and the particles are strongly fixed, but it is difficult to complete the reaction in the base material, and there is likely to be considerable residual monomer and residual crosslinking agent. In another example, a certain amount or more of an aqueous monomer solution is carried as fine particles on a raised nonwoven fabric, and then polymerized and thermally compressed (see for example Patent Document 20). The absorption performance of the composite is high in this case because of the large quantity of water-absorbent resin, and because a nonwoven fabric is used there is less movement than with pulp. However, because polymerization is performed in a nonwoven fabric there is still the problem of residual monomers. Another method is to re-impregnate a water-absorbent resin with an aqueous solution of unpolymerized monomer, apply it to a base material and polymerize the impregnated monomer to thereby bond the water-absorbent resin to the base material (see for example Patent Document 31), but it is difficult to completely polymerize the residual monomer after it adheres to the base material, and large quantities of residual monomers occur.

In a similar example, the water-absorbent resin is made into a slurry and applied to a base material (see for example Patent Document 21). Productivity is certainly improved by applying a slurry, but expensive microfibril fiber must be used as the dispersion medium, and the adhesive force may not be adequate. In thin sanitary materials and other absorbent materials with a higher proportion of water-absorbent resin, because more water-absorbent resin is used the resin can swell and become rather bulky after absorbing water depending on how it is positioned. The more strongly the water-absorbent resin is fixed, the more it presses on the body when it becomes bulky.

A method has also been proposed of printing drops of low-viscosity aqueous monomer solution on fabric, and then performing a polymerization reaction with the fabric to thereby provide gaps between polymerized particles and prevent gel blocking (see for example Patent Document 30). In this case, large amounts of residual monomers and low-molecular-weight components remain because of the difficulty of achieving complete polymerization on a base material. This not only makes the product undesirable for use as a sanitary material, but also reduces the absorption speed. When arranging resin on both sides of one sheet of fabric in an effort to achieve the desired level of absorption relative to area, moreover, the resin must have a large particle size of 550 μm or more, and the extremely small surface area/volume of the spherical, semi-spherical and deformed spherical particles obtained by this method does not provide sufficient absorption speed for actual use.

From the standpoint of comfort, it is important to prevent not only leakage but also dampness in a hygiene product. Absorbent products have been proposed in which dampness is reduced by controlling the rise in humidity that occurs during use (see for example Patent Document 22 and 23). In the techniques described in these publications, the absorbent bodies contain absolute dry pulp, a large quantity of highly-absorbent polymer and a hygroscopic material such as silica gel or lithium chloride, in combination with a moisture permeable back sheet. Some absorbent products also use a moisture permeable back sheet (see for example Patent Document 24). Another technique combines two moisture permeable sheets in order to prevent liquid from seeping through the moisture permeable back sheet even under pressure. However, because in these methods the secreted bodily fluid remains unfixed between the fibers of the paper or pulp, when a large amount of bodily fluid is excreted the unfixed liquid may produce steam, resulting in dampness.

There have also been proposed a sanitary napkin wherein rewetting from the absorbent body is prevented through the use of an absorbent body in which the centrifugal holding capacity after equilibrium absorption swelling of false blood and the false blood permeating speed are at or above a fixed value (see for example Patent Document 25), a multilayer absorbing paper having a surface layer to be first contacted with a liquid and made of mixed bulky cellulose fiber and one or more base material layers laminated to the surface layer (see for example Patent Document 26), and an absorbent sheet comprising hydrophilic fine fibers or a hydrophilic fine powder contained in an absorbent sheet comprising a highly-absorbent polymer and bulky cellulose fiber (see for example Patent Document 27). However, these publications do not describe the configuration of an absorbent article that allows steam to be dramatically controlled and humidity to be dramatically suppressed even when the amount of excretion (amount of liquid to be absorbed) is large.

Another method for controlling dampness uses fiber with a low water-holding capacity for the absorbent layer (see for example Patent Document 28). There is certainly less dampness with this method, but because the fiber functions hardly at all as an absorbent body, absorption is dependent entirely on an absorbent resin with a slow absorption speed, resulting in slower absorption. Because the fiber expands very little as it swells, moreover, gel blocking is likely and it is difficult for the water-absorbent resin to perform properly.

It has been reported that the absorbent capability of a water-absorbent resin is affected by the shape of the particles (see for example Patent Document 29). Commonly used water-absorbent resin particles are not especially long and thin and have a particle diameter of about 45 to 850 μm with a mass median particle diameter of about 200 to 370 μm, but the absorbent capability of a structure and the effective capability of the water-absorbent resin in it were improved by means of a relatively large particle size distribution, with a median particle diameter of 400 to 700 μm. Conventionally, however, when the absorbent capability is improved the effect of blocking cannot be avoided because there is more contact between particles. Because of the low proportion of water-absorbent resin, moreover, the absorbent capability of the absorbent body is low.

Thus, most absorbent bodies in which a water-absorbent resin is bonded to a base material use adhesion by monomer polymerization (raising the issue of residual monomers) or adhesion using an adhesive (which restricts swelling), and no satisfactory adhesion method currently exists. Moreover, only absorbent bodies with poor performance have been produced because the resin is not in a state that allows high absorption performance after adhesion. That is, no thin, lightweight absorbent body has been obtained having high liquid holding capability and absorption speed, high liquid dispersibility and high stability of the absorbent body.

[Patent Document 1] Japanese Patent Application Laid-open No. 2001-252307
[Patent Document 2] WO98/037149
[Patent Document 3] Japanese Patent Application Laid-open No. 06-057010
[Patent Document 4] WO01/64153
[Patent Document 5] Japanese Patent Application Laid-open No. 5-230747
[Patent Document 6] Japanese Patent Application Laid-open No. 10-118114
[Patent Document 7] Japanese Patent Application Laid-open No. 10-118115
[Patent Document 8] Japanese Patent Application Laid-open No. 5-31362
[Patent Document 9] Japanese Patent Application Laid-open No. 6-370
[Patent Document 10] Japanese Patent Application Laid-open No. 2000-238161
[Patent Document 11] Japanese Translation of PCT International Publication No. 10-510447
[Patent Document 12] Japanese Patent Application Laid-open No. 2001-96654
[Patent Document 13] Japanese Patent Application Laid-open No. 2001-171027
[Patent Document 14] Japanese Patent Application Laid-open No. 2004-001355
[Patent Document 15] Japanese Patent Application Laid-open No. PL365287
[Patent Document 16] Japanese Patent Application Laid-open No. 2001-96654
[Patent Document 17] Japanese Patent Application Laid-open No. 10-512183
[Patent Document 18] Japanese Translation of PCT International Publication No. 10-508528
[Patent Document 19] Japanese Patent Application Laid-open No. 2003-11118
[Patent Document 20] Japanese Patent Application Laid-open No. 2004-124303
[Patent Document 21] Japanese Patent Application Laid-open No. 11-137600
[Patent Document 22] Japanese Patent Application Laid-open No. 6-218007
[Patent Document 23] Japanese Patent Application Laid-open No. 7-132126
[Patent Document 24] Japanese Translation of PCT International Publication No. 10-508521
[Patent Document 25] Japanese Patent Application Laid-open No. 7-184956
[Patent Document 26] Japanese Patent Application Laid-open No. 6-287886
[Patent Document 27] Japanese Patent Application Laid-open No. 9-156013
[Patent Document 28] Japanese Patent Application Laid-open No. 2002-165837
[Patent Document 29] Japanese Patent Application No. 2904791
[Patent Document 30] US2003/0205318 A1
[Patent Document 31] Japanese Patent Application Laid-open No. 9-239912
[Patent Document 32] Japanese Patent Application Laid-open No. 2005-200630

DISCLOSURE OF INVENTION

Problem to be Solved by the Invention

It is an object of the present invention to provide a thin, lightweight absorbent body and bodily fluid-absorbing article with high absorption capability, absorption speed and dispersibility. In particular, it is an object of the present invention to provide an absorber and bodily fluid-absorbing article that can be used favorably in disposable diapers, sanitary napkins, incontinence pads and the like. More particularly, it is an object of the present invention to provide an absorber and bodily fluid-absorbing article which can absorb stably with almost no movement or uneven distribution of the absorber in a sanitary product, and that can absorb liquid to be absorbed with a minimum amount of material used. In addition, it is an object of the present invention to provide an environmentally-friendly absorber and bodily fluid-absorbing article whereby the pulp and other resources commonly used in hygiene products can be conserved.

Means for Solving the Problems

As a result of exhaustive research to address the above-identified problem, we found that high absorption capability could be achieved with a small amount of water-absorbent resin while reducing the amount of other materials by using an absorbent composite wherein a base material and water-absorbent resin particles are made into a composite as the absorber, and the base material and water-absorbent resin particles are combined in specific proportions and in a specific arrangement.

That is, the following absorbent composite, method for manufacturing the absorbent composite and device for manufacturing the absorbent composite are provided.

An absorbent composite comprising: a base material and water-absorbent resin particles: wherein the following conditions (1) to (4) are fulfilled:

(1) the weight ratio of water-absorbent resin relative to the total weight of the base material and water-absorbent resin is 65 to 99 wt %, (2) the water-absorbent resin particles adhering directly to the base material constitute 50 wt % or more of the total water-absorbent resin particles;

(3) the average absorption capacity of the water-absorbent resin particles is 50 g/g or more; and (4) the amount of residual monomers in the water-absorbent resin is 200 ppm or less.

A method for manufacturing an absorbent composite comprising a base material and water-absorbent resin particles, comprising making the base material and/or the water-absorbent resin absorb water, followed by removing water from and drying the base material and water-absorbent resin while making them be in contact with each other.

A device for manufacturing an absorbent composite comprising a base material and water-absorbent resin particles, comprising: a base material feed part; a rotating drum for adhering the resin particles to the base material: a part for supplying the resin particles to the rotating drum: a drying part for removing water from the base material with the resin particles adhered thereto: and a part for supplying a specific amount of moisture to the base material and/or resin particles: wherein the device has the following features (1) and (2):

(1) the rotating drum has multiple dimples on its surface, and (2) teach of the dimples has a ventilation hole at its bottom, through which a gas can be blow out from the inside of the rotating drum.

Effect of the Invention

The present invention is an integrated absorbent composite comprising many water-absorbent resin particles adhered onto a base material, thereby providing a thin absorber with high liquid dispersibility and liquid holding capability. By using this absorber in a sanitary material or other bodily fluid-absorbing article, the process of manufacturing the sanitary material can be simplified, and the water-absorbent resin is utilized efficiently, thus the amount of the water-absorbent resin and paper, fabric and other materials used in the absorber can be reduced. As a result, unprecedented thin, lightweight sanitary materials and other bodily fluid-absorbing articles can be provided.

BEST MODE FOR CARRYING OUT THE INVENTION

The present invention is explained in more detail below.

1. Overview of the Structure and Performance of the Absorbent Composite of the Present Invention In the present invention, an absorbent composite means a combination of a water-absorbent resin and a base material. In this composite, 50 wt % or more of the water-absorbent resin particles adhered directly to the base material, thus there is little change in the positions of the resin particles. Consequently, the base material maintains its sheet shape. The absorption capability as an absorber of this absorbent composite is preferably adjusted by mixing pulp or other short fibers or other sheet-shaped materials into the absorbent composite.

In the present invention, the water-absorbent resin particles are preferably relatively large particles (particle diameter 550 µm to 2100 µm) [hereinafter referred to as "large particles"], as the absorbent composite using these particles has high absorption capacity per area and the absorption speed that allows the composite to be used as a sanitary material. Large particles have conventionally been avoided in absorber for sanitary materials because of their slow absorption speed, but when they are directly adhere to the fibers of a base material, the liquid can be transported inside the particles via the adhered fibers, a stress resulting from morphological change of fibers in contacting with water are loaded on the adhering large particles, and the absorption speed of large particles is dramatically improved, thus allowing them to be used as constituents of an absorbent product for sanitary materials.

In arranging the resin particles on the base material, it is preferable to maintain an area occupancy rate of the large particles to be 1 to 30% on at least one side, as the swollen resin particles will bump against each other and block each other from swelling and the resin in the composite will not absorbed adequately if sufficient space is not provided for the particles to swell in a direction parallel to the plane of the base material. In this case, it is more preferable to arrange the particles so as to prevent them from contacting each other, and it is more preferable to space out the water-absorbent resin particles. Preferably, the water-absorbent resin particles are arranged in a single layer so that they do not overlap each other. Moreover, the large particles are preferably arranged on both sides, and maintain the area occupancy rate of the large particles in the range of 1 to 30% on both sides. If the composite also contains relatively small particles, they will only swell down below the large particles without greatly blocking the large particles from swelling, so it is possible and preferable to adjust the absorption speed to the required speed for the absorber by adding such small particles. When such relatively small water-absorbent resin particles are added to adjust the absorption speed, the total surface area coefficient (explained in detail below) is preferably adjusted to the range of 0.3 to 3 in order to provide a good balance between absorption capacity and absorption speed in the composite.

Since a relatively high absorption capacity is required for purposes of a sanitary material, the weight ratio of the water-absorbent resin relative to the total weight of the water-absorbent resin and the base material must be between 65 and 99 wt %.

The reason why gel blocking does not occur even with such a high weight ratio is that 50 wt % or more of the resin particles adhere to the base material, thereby ensuring a certain space between the resin particles. The proportion of the adhering resin particles is preferably at least 60 wt %, more preferably at least 70 wt %, or further more preferably at least 90 wt % or ideally 95 wt % or more. It is preferable that the water-absorbent resin particles adhere to the base material, because it can prevent the water-absorbent resin particles from moving during transportation or absorption of bodily fluid.

The method for directly adhering the water-absorbent resin particles to the base material is not particularly limited. It is preferable that some of the fibers of the base material are incorporated into the water-absorbent resin particles. It is preferable that at least 50 wt % of the directly adhering water-absorbent resin particles are adhere with incorporating some of the fibers therein, and preferably at least 70%, more preferably at least 90 wt % or still more preferably at least 95% of the water-absorbent resin are adhere in such a manner. When the water-absorbent resin particles adhere with incorporating some of the fibers therein, the fibers act as a conduit when the water-absorbent resin absorbs bodily fluid, the absorption capacity of the resin particles under pressure as well as the absorption speed increase.

It is impossible to achieve a high absorption capacity of the absorber merely by using large particles and thus increasing volume of resin relative to area, and the resin particles must also have a high absorption capacity. That is, the average absorption capacity of the water-absorbent resin particles used must be at least 50 g/g. Water-absorbent resin particles having such a high absorption capacity are generally liable to gel blocking, and their swelling may also be greatly blocked when the resin particles bump against each other, so an absorbent composite meeting with various requirements cannot be achieved just by using a composite with a high resin proportion of more than 50 wt %. Consequently, in the past it has been necessary to use hard resin particles with a high degree of crosslinking on the surface and inside which have a high absorbing capability under pressure and a low absorption capacity. In the present invention, the water-absorbent resin particles are arranged so as to avoid gel blocking, and due to the presence of conduits in the resin in some cases, high absorbing capability under pressure can be achieved even using soft resin particles with a high absorption capacity. As a result, the absorbent composite has high absorption capability under pressure or under no pressure.

Moreover, because the absorbent composite of the present invention has high bodily fluid dispersibility and makes all of the water-absorbent resin maximize its absorption capability, an excess of water-absorbent resin need not to be used and the absorbent composite can be made lightweight. To improve the absorption capacity of the composite it is preferable to increase the proportion of highly absorbent resin, and it is more preferable to use a highly absorbent resin with a higher absorption capacity.

As is regulated by the voluntary standards of the Japan Hygiene Products Industry Association regarding the water-absorbent resin, reductions of residual monomers is required. One feature of the absorbent composite of the present invention is that the residual monomers in the water-absorbent resin have been reduced to a dramatically low value of 200 ppm or less. Such a value is hard to achieve by polymerizing resin on a base material that is commonly used method to adhere resin directly to a base material. This low level of residual monomers can be achieved by polymerizing the water-absorbent resin in advance followed by using the resin with a specific low level of residual monomers as the water-absorbent resin of the composite.

2. Adhesion

In the present invention, it is preferable that at least 60 wt %, preferably at least 70 wt %, more preferably at least 90 wt %, or still more preferably at least 99 wt % of the total water-absorbent resin particles are adhere to the base material at the time when the absorbent composite is used.

In the present invention, the status in which the water-absorbent resin particles adhere to the base material means the status in which the water-absorbent resin particles are fixed on the base material, and positional relationship between the base material and the water-absorbent resin particles does not essentially change. Specifically, adhering particles means that the particle that is not detached after shaking back and forth the absorbent composite with the surface having the adhering particles underneath for one minute at a rate of 2 complete (back and forth) shakes per second with a shake distance of 20 cm (back (20 cm) and forth (20 cm)), while holding the edge of the absorbent composite by hand.

If the positional relationship between the base material and water-absorbent particles does not change, the absorption capability of the absorbent composite will not change due to transportation before use, and this is also preferable from the standpoint of repeated absorption.

The percentage of adhering particles can be determined by detaching the adhering particles by force with tweezers or the like and measuring the weight of them.

In the present invention, at least 50 wt % of the total water-absorbent particles adhere directly to the base material at the time when the absorbent composite is used. Preferably, at least 60 wt %, more preferably at least 70 wt %, still more preferably at least 90 wt % or ideally at least 99 wt % adhere directly to the base material.

Adhere directly, as used herein, means that they adhere without using any components such as adhesive other than the components including the base material, the water-absorbent resin particles and derivatives thereof. However, they are still considered to adhere directly if an adhesive is used to such an extent as not to inhibit swelling.

The percentage of directly adhering particles can be determined by measuring the amount of water-absorbent resin particles still adhering after 1 hour of immersion of the absorbent composite in a solvent that dissolves the adhesive.

The method for adhering directly is not particularly limited, and includes adhesion by chemical bonding between the base material and the water-absorbent resin particles, adhesion by physical interaction and adhesion by incorporating the fiber into the water-absorbent resin.

Of these, adhesion by incorporating the fiber into the water-absorbent resin is preferred. Specifically, it is preferable that at least 50 wt % of the total water-absorbent resin particles adhere with fibers incorporated into the water-absorbent resin. Preferably at least 60 wt %, more preferably at least 70 wt % or still more preferably at least 90 wt % of the particles adhere in this manner.

Fibers incorporated into the water-absorbent resin means that fibers of the base material are present in the water-absorbent resin matrix. There are no particular limitations on the shape and length of the incorporated fibers. Because water can be taken up into the water-absorbent resin via the fibers, adhesion of this type provides superior absorption capability from the standpoint of absorbed volume and absorption speed. An electron microscope can be used to determine whether the particles adhere with fibers incorporated into the water-absorbent resin. The proportion can be determined by selecting 30 adhering particles at random, detaching them by force from the base material, and observing them with an electron microscope.

In the present invention, the method of adhesion of the remaining water-absorbent resin particles does not matter as long as at least 50 wt % of the total water-absorbent resin particles adhere directly to the base material.

However, it is preferable not to use adhesive from the standpoint of preventing the blocking of swelling when liquid is absorbed. It is not preferable to use adhesive because it may block the water-absorbent resin from swelling. Examples of adhesives include thermoplastic fibers and polymers, emulsion binders, hot melt adhesives and the like.

The adhering large particles are preferably arranged with a resin area occupancy rate (described below) of 1 to 30%. The absorption capability of the large particles is facilitated if they are arranged in such a way that they do not come in contact with each other when they absorb the expected amount of liquid. The large particles may adhere only to one side of the base material or may adhere to both sides of the base material. It is preferable that they adhere to both sides is desirable because it increases the absorption amount per unit area.

3. Absorbent Resin Weight Ratio

The weight ratio of the water-absorbent resin in the present invention is given as the weight percentage of the water-absorbent resin relative to the total weight of the base material and the water-absorbent resin, and is specifically determined by the following formula (Formula 1):

Weight ratio (wt %) of resin=$A/B \times 100$ (Formula 1)

(wherein the weight of the water-absorbent resin in the absorbent composite is A (g) and the total weight of the base material and the water-absorbent resin is B (g)).

The weight ratio must be at least 65 wt % and not more than 99% at the time when the absorbent composite is used, and is preferably at least 70 wt % and not more than 99 wt % or more preferably at least 80 wt % and not more than 99 wt %. The higher the weight ratio, the higher the total amount absorbed by the composite. The weight of the water-absorbent resin is measured after having detached all of the particles.

3. Resin Area Occupancy Rate

The resin area occupancy rate of the water-absorbent resin particles in the particle size range from 550 to 2100 μm (that is, large particles) in the present invention is an indicator of possibility of contact between particles when the absorbent resin particles have absorbed a liquid. In the present invention, the resin area occupancy rate of the large particles is measured as follows.

A photograph of the surface of the absorbent composite is taken with an optical microscope or electron microscope. The measurement conditions and magnification are set so that the water-absorbent resin can be distinguished from the base material, and that 10 or more water-absorbent resin particles with a diameter of 550 to 2100 μm (that is, large particles) appear in one photograph. The enlarged photocopy of the photograph is prepared, the parts corresponding to the water-absorbent resin particle are cut out from the parts corresponding to the base, and the large particles are selected from the water-absorbent resin particle parts. The following method is used for selection.

Square paper corresponding to a 500 μm-square of on the composite is prepared by calculating based on the magnification of the photograph and the magnification of the enlarged copy. Square paper corresponding to a 2500 μm-square is also prepared in the same way. The large particles are selected by laying each part of the copy of the water absorbent resin particles over these squares and excluding those particles whose copies are small enough to fit within the 500 μm-square or large enough to protrude even slightly from the 2500 μm-square.

The weight of selected cutout parts corresponding to large particles and whole enlarged copy are weighed, and the resin area occupancy rate of large particles is calculated based on the following formula (Formula 2). Any five or more points on the absorbent composite or photographed, and the average is determined to be the area occupancy rate. When water-absorbent resin particles are adhere to both sides of the base material, the occupancy rate of each side is determined respectively.

Resin area occupancy rate (%)=weight of cutout parts corresponding to large particles/weight of whole enlarged copy×100 (Formula 2)

The resin area occupancy rate is preferably 1 to 30(%), more preferably 2 to 25, or still more preferably 3 to 20 at the time when the absorbent composite is used. If the area occupancy rate is too high, the water-absorbent resin particles will contact with each other when they swell, resulting in blocking so that the water-absorbent resin cannot maximize its absorption capability. If the resin area occupancy rate is too low, the amount of absorption per unit area of the absorbent composite will be undesirably low.

4. Total Surface Area Coefficient

In the present invention, the total surface area coefficient is an indicator of the surface area of water-absorbent resin particles per unit area of the absorbent composite. A greater total surface area coefficient is preferable, as the greater the total surface area coefficient, the faster the absorption speed of the absorbent composite.

The total surface area coefficient is preferably about 0.1 to 3, and when especially rapid absorption is required in the early stages (within first 1 minute after initiation of use), it is preferably 0.3 to 3, more preferably 0.4 to 3 or still more preferably 0.5 to 3 at the time when the absorbent composite is used.

The total surface area coefficient in the present invention is determined according to (Formula 3) by collecting the water-absorbent resin particles used in the absorbent composite, classifying them by particle size, measuring the weight and the bulk density of particles in respective particle size range.

$$\text{Total surface area coefficient} = \sum_r \frac{3 \times Wr}{\Pi \times r \times Cr \times S} \quad \text{(Formula 3)}$$

(wherein Wr is the total weight (g) of water-absorbent resin particles of particle size r (cm), Cr is the bulk density (g/cm$^2$) of water-absorbent particles of particle size r (cm) and S is the area (cm$^2$) of the absorbent composite).

The water-absorbent resin particles are taken out (by peeling when they adhere to the base material) and collected to measure particle size and bulk density of the water-absorbent resin particles, and where fibers or the like adheres to the surfaces of the water-absorbent resin particles, they are removed before measurement. Where fibers are incorporated into the water-absorbent resin particles, the fibers on the particle surfaces are cut off before measurement. Where adhesive or the like has been applied to the surfaces of the water-absorbent resin particles, the adhesive is removed using a solvent that is not absorbed by the water-absorbent resin.

The particle size of the water-absorbent resin particles is measured by sieving them with sieves with a sieve opening of mesh of 106 µm, 212 µm, 300 µm, 425 µm, 500 µm, 600 µm, 710 µm, 850 µm, 1000 µm, 1180 µm, 1400 µm, 1700 µm and 2500 µm. In the present invention, the particle size is determined to be an intermediate value between the value of sieve opening of two sieves through which a particle passes and through which it does not pass. The particle size of particles that passes through a sieve with a sieve opening of 106 µm is determined to be 53 µm, and the particle size of particles that remains on a sieve with a sieve opening of 2500 µm is determined to be 2700 µm. By this operation, the particles are classified into particle sizes of 53 µm, 159 µm, 256 µm, 362.5 µm, 462.5 µm, 550 µm, 655 µm, 780 µm, 925 µm, 1090 µm, 1290 µm, 1550 µm, 1850 µm, 2100 µm and 2700 µm.

The bulk density of the water-absorbent resin particles is determined by measuring out a 2 cm$^3$ of water-absorbent resin using a 2 cm$^3$ measurement flask, and dividing the weight in two. The bulk density is measured 5 times, and the average value is taken. Bulk density is measured for particles in each particle size grade after having been sieve-classified.

5. Water-Absorbent Resin Particles (Water-absorbent Resin)

The water-absorbent resin constituting the water-absorbent resin particles in the present invention is explained first.

In the present invention, the water-absorbent resin preferably have a residual monomer concentration of 200 ppm or less, more preferably 100 ppm or less, further more preferably 50 ppm or less or still more preferably 10 ppm or less relative to the weight of the water-absorbent resin. It is not preferable that the water-absorbent resin include residual monomer in high concentration, as they elute during liquid absorption.

Residual monomers can be reduced by completing polymerization by heat treatment either during or after manufacturing the absorbent composite. The residual monomer concentration of the absorbent resin before contacting with the base material is preferably 5% or less, more preferably 1% or less, further more preferably 0.1% or less or still more preferably 0.05% or less. It is not preferable to use the water-absorbent resin with many residual monomers as a starting material, as it becomes difficult to complete polymerization during manufacturing the composite, and a large quantity of residual monomers still remain at the end. The texture of the base material may also be adversely affected by the polymerization reaction method.

For such reasons, in the present invention, it is preferable to use amorphous particles manufactured by a method comprising aqueous solution polymerization followed by pulverization and/or particles manufactured by reverse-phase suspension polymerization.

The amount of residual monomers can be measured by the following method.

The water-absorbent resin is added to 0.9% saline in the amount of 250 times the weight of the resin, the residual monomers are extracted for 6 hours by stirring at room temperature, and filtered. The amount of residual monomers of the filtrate is determined by liquid chromatography.

In the present invention, the type of water-absorbent resin is not particularly limited, and any kind of water-absorbent resin can be used. A water-absorbent resin having acid groups in the side chains is preferred, and a resin having carboxylic acid groups in the side chains is especially preferred. It is desirable that 50% or more of the acid groups are neutralized in the form of salts, and especially desirable that 50% or more of the acid groups are neutralized in the form of ammonium salts. A water-absorbent resin having acid groups in the side chain is preferred because the absorption speed is enhanced due to static repulsion between the acid groups during liquid absorption. It is desirable for the acid groups to be neutralized because thereby the liquid is absorbed into the inside of the water-absorbent resin by osmotic pressure. It is preferable that the acid groups are neutralized in the form ammonium of salts, because ammonium salts have a high affinity for water and are therefore more absorbent.

Many types of water-absorbent resin are known, including crosslinked partially-neutralized polyacrylic acid (see for example Japanese Patent Application Laid-open No. S55-84304), hydrolyzed starch-acrylonitrile graft polymer (see for example Japanese Patent Publication No. S49-43395), neutralized starch-acrylic acid graft polymer (see for example Japanese Patent Application Laid-open No. S51-125468), saponified vinyl acetate-acrylic acid ester copolymer (see for example Japanese Patent Application Laid-open No. S52-14689), hydrolyzed acrylonitrile copolymer or acrylamide copolymer (see for example Japanese Patent Publication No. S53-15959), polyglutamic acid salts (see for example Japanese Patent Application Laid-open No. 2003-192794) and the like.

Polyacrylic acid salt copolymers and crosslinked partially-neutralized polyacrylic acid, which are commonly used for sanitary materials, are preferred from the standpoint of absorption performance and cost.

Crosslinked polyacrylic acid is explained below as a desirable example of a water-absorbent resin, along with a manufacturing method the same.

In crosslinked polyacrylic acid, preferably at least 50 mol %, more preferably at least 80 mol % or still more preferably at least 90 mol % of the repeating units in the polymer molecule chains are carboxyl group-containing units. It is not preferable that the proportion of the carboxyl group-containing unit in the repeating units is 50 mol % or less because absorption capability is adversely affected.

It is preferable that the carboxyl groups in the polymer molecule chains are partially neutralized, and alkali metal salt including sodium, potassium and lithium; and nitrogen-containing basic substance including ammonia may be used as a salt. Preferably at least 50% and more preferably at least 70% of the carboxyl groups are neutralized. In terms of the kind of salt, it is preferable that the carboxyl groups are partially neutralized with at least one salt including ammonia, and it is most preferable that the carboxyl groups are partially neutralized with ammonia alone. From the standpoint of absorption capability, at least 50 mol %, more preferably at least 70 mol %, still more preferably at least 90 mol % or ideally all of the carboxyl group neutralized salts in the polymer molecule chains are ammonia salts. It is preferable that the proportion of ammonia salts is high from the standpoint of absorption capacity and adhesiveness to the base material. The proportion of ammonia salts in the water-absorbent resin can be calculated from the total amount of nitrogen atoms in the water-absorbent resin. The total amount of nitrogen atoms in the water-absorbent resin can be determined by the Kjeldahl method.

The monomers constituting the water-absorbent resin may be neutralized salts of unsaturated carboxylic acid monomers such as (meth)acrylic acid, ethacrylic acid, itaconic acid, maleic acid, crotonic acid, fumaric acid, sorbic acid, cinnamic acid and anhydrides thereof, and preferably a neutralized salt of (meth)acrylic acid is used. The neutralized salt is preferably alkali metal salt including lithium, sodium and potassium or nitrogen-containing basic substance including ammonia. Other monomers may also be copolymerized, and examples of unsaturated monomers that may be copolymerized include anionic unsaturated monomers such as (meth) acrylic acid, ethacrylic acid, itaconic acid, maleic acid, crotonic acid, sorbic acid, cinnamic acid, anhydrides thereof, vinylsulfonic acid, allylsulfonic acid, styrenesulfonic acid, vinyltoluenesulfonic acid, 2-(meth)acrylicamide-2-methylpropanesulfonic acid, 2-(meth)acryloyl ethanesulfonic acid, 2-(meth)acryloyl propanesulfonic acid, 2-hydroxyethylacryloylophosphate, 2-hydroxylethyl methacryloyl phosphate, phenyl-2-acryloyloxyethyl phosphate and vinyl phosphoric acid and salts thereof, nonionic hydrophilic group-containing unsaturated monomers such as acrylamide, methacrylamide, N-ethyl (meth)acrylamide, N-n-propyl (meth)acrylamide, N-isopropyl (meth)acrylamide, N,N-dimethyl (meth)acrylamide, 2-hydroxyethyl (meth)acrylate, 2-hydroxypropyl (meth)acrylate, methoxypolyethylene glycol (meth)acrylate, polyethylene glycol mono(meth)acrylate, N-vinylpyrrolidone, N-acryloylpiperidine and N-acryloylpyrrolidine and, and hydrophilic monomers that yield water-absorbing property by hydrolysis of the functional groups after polymerization such as methyl (meth)acrylate, ethyl (meth)acrylate and vinyl acetate that form. Hydrophobic monomers that may be used in combination include styrene, vinyl chloride, butadiene, isobutene, ethylene, propylene, stearyl (meth)acrylate, lauryl (meth)acrylate and the like, and these may be used singly, or in combination of two or more thereof.

A crosslinking agent may be used with the monomers, and the resin may be crosslinked by reacting a condensation crosslinking agent with functional groups in the resin, by copolymerizing a polymerizable crosslinking agent with unsaturated monomers or by exposing the resin to electron beams or radiation or the like. A preferred crosslinking method is using a condensation crosslinking agent and a more preferred crosslinking method is copolymerizing a polymerizable crosslinking agent with unsaturated monomers in the presence of a condensation crosslinking agent that reacts with functional groups in the resin.

Examples of condensation crosslinking agents include glycidyl ether compounds such as ethylene glycol diglycidyl ether, trimethylol propane triglycidyl ether, (poly)glycerine polyglycidyl ether, diglycerine polyglycidyl ether and propylene glycol diglycidyl ether; polyvalent alcohols such as (poly)glycerine, (poly)ethylene glycol, propylene glycol, 1,3-propanediol, polyoxyethylene glycol, triethylene glycol, tetraethylene glycol, diethanolamine and triethanolamine; polyvalent amines such as ethylenediamine, diethylenediamine, polyethylenimine and hexamethylenediamine; and polyvalent ions such as zinc, calcium, magnesium and aluminum, and these crosslinking agents may be used in combination of two or more.

Examples of polymerizable crosslinking agents that copolymerize with unsaturated monomers include diethylene glycol diacrylate, N, N'-methylenebisacrylamide, polyethylene glycol diacrylate, polypropylene glycol diacrylate, trimethylol propane diallyl ether, allylglycidyl ether, pentaerythritol triallyl ether, pentaerythritol diacrylate monostearate, bisphenol diacrylate, isocyanuric acid diacrylate, tetraallyloxyethane and diallyloxyacetic acid salt, and these crosslinking agents may be used in combination of two or more.

The solvent for the monomer solution is not particular limited as long as it has excellent dissolving properties. Water alone is particularly desirable, but hydrophilic solvents such as ethanol, methanol and acetone may also be used either singly or in combination of two or more. A salt such as sodium chloride, a basic compound such as ammonia for controlling pH, or a suspending agent in the case of reverse-phase suspension polymerization may also be added as necessary.

The method of polymerizing the unsaturated monomers is not particularly limited, and a commonly used method such as aqueous solution polymerization, reverse-phase suspension polymerization, reverse-phase emulsion polymerization, spray polymerization, belt polymerization or the like may be used. The polymerization initiation method is also not particularly limited, and polymerization may be initiated by using a radical polymerization initiator, by exposure to radiation, electron beams or the like, or by using a photosensitizer in ultraviolet polymerization. The initiator used in radical polymerization may be a known initiator such as for example a persulfate such as potassium persulfate, ammonium persulfate or sodium persulfate; hydrogen peroxide; or an organic peroxide such as cumene hydroperoxide, t-butyl hydroperoxide, peracetic acid or the like. When using an oxidizing radical polymerization initiator, a reducing agent such as L-ascorbic acid or Rongalite may also be added.

An oxygen removal operation is preferably carried out in the monomer solution prior to initiating polymerization. An example is removing dissolved oxygen by bubbling or the like with an inactive gas for a sufficient period of time. The atmosphere in the reaction container is preferably substituted by an inactive gas such as nitrogen or helium. The inside of the reaction container may be under reduced pressure, normal pressure or increased pressure. The polymerization initiation temperature is generally preferably in the range of 0 to 100° C. or more preferably in the range of 20 to 70° C. If the initiation temperature is too high, polymerization occurs due to heat before adding the initiator, which is not desirable. A low initiation temperature is undesirable because reaction initiation takes longer. The temperature inside the container may be let follow its course during the reaction, or may be controlled by cooling or heating. The rate of temperature increase and maximum temperature during polymerization may not be strictly controlled, and the maximum temperature may exceed 100° C. The maximum temperature during polymerization is generally in the range of 20 to 140° C. or preferably 40 to 120° C. The concentration of the monomer solution is preferably 10 to 80% or more preferably 30 to 70%. It is not preferable that the concentration is too high because the reaction tends to get out of control. It is not preferable that the concentration is too low because the reaction takes to much time and the subsequent drying step becomes more difficult. It is preferable to terminate the polymerization when the reaction solution ceases to generate heat. Since polymerization is followed by heating process, such as drying, crosslinking and the like, polymerization may also be terminated before the reaction solution ceases to generate heat. The solution may also be heated or kept warm after it ceases to generate heat.

The polymer obtained after above-mentioned polymerization is dried when it is a wet gel. The drying method is not particularly limited. Azeotropic drying, fluidized drying, hot air drying, vacuum drying or the like can be preferably used, and hot air drying or vacuum drying is particularly desirable. The polymer is dried until the water content become 30 wt % or less or preferably 10 wt % or less. A wet gel may be dried in any form, it is preferable to dry the polymer after having increased the surface area by grounding them coarsely. The drying temperature is preferably in the range of 70° C. to 180° C. or more preferably 100 to 140° C.

The particle size of the dried polymer is adjusted as necessary by operations such as pulverization or classification. When crosslinked polyacrylic acid is used, the dried polymer may be pulverized into a specific particle size and then be heated. It is preferable to add a compound having 2 or more functional groups that are capable of reacting with the carboxyl groups used during this heat treatment. The compound having 2 or more functional groups capable of reacting with carboxyl groups may be added before polymerization, or may be added to the particles before heat treatment. When the compound is added before heat treatment, it is preferable that the compound is added by dissolving it in a hydrophilic solvent such as water, alcohol or ether, and dispersing the solution on the surface. The heat treatment temperature is not particularly limited, and is preferably in the range of 120 to 250° C., more preferably 150 to 240° C. or still more preferably 170 to 230° C. Heat treatment may be carried out continuously in the same unit after drying, or may be an independent step from the drying step.

An ordinary dryer or furnace may be used for this heat treatment, and for example a channel dryer, rotary drier, disc dryer, fluidized bed dryer, air current dryer, infrared dryer or the like may be used.

Deodorants, perfumes, various inorganic powders, foaming agents, pigments, dyes, antibacterial agents, hydrophilic short fibers, plasticizers, adhesives, surfactants, fertilizers, oxidizing agents, reducing agents, chelating agents, antioxidants, thermal stabilizers, ultraviolet absorbers, light stabilizers, water, salts and the like may be added to the water-absorbent resin as necessary.

Examples of above-mentioned inorganic powders include fine particles of various inorganic compounds that are inactive with water and hydrophilic organic solvents and fine particles of clay minerals. Inorganic powders that have a certain affinity for water but are insoluble or poorly soluble in water are particularly desirable as inorganic powders, and examples include metal oxides such as silicon dioxide, titanium; silicic acids (salts) such as natural zeolite, synthetic zeolite; kaolin; talc; clay; bentonite and the like.

The amount of inorganic powder that is used is normally 0.001 to 10 weight parts or preferably 0.01 to 5 weight parts per 100 weight parts of water-absorbent resin. The method of mixing the water-absorbent resin and inorganic powder is not particularly limited and may be dry blending, wet mixing or the like.

(Particle Shape)

The water-absorbent resin particles may be of any shape, and may be in the form of spherical particles widely used in absorbent compositions, amorphous particles, aggregated particles, short fibers, long fibers or particle with sheet shape. Amorphous particle obtained by pulverization, particle aggregates (such as grape clusters), particle with scale shape, granules and the like may also used. Preferred particles include aggregated particles, spherical particles or amorphous particles.

However, a water-absorbent resin that is used as large particles is preferably in the form of amorphous particles manufactured by polymerization by aqueous solution polymerization followed by pulverization, and/or particle aggregates manufactured by reverse-phase suspension polymerization. This is because that it is hard to achieve a satisfactory absorption speed for sanitary materials with spherical particles due to their extremely low specific surface area even if the absorption speed is increased due to the composite effect with the base material, (Salt Concentration Near the Surface)

The salt concentration of the water-absorbent resin particles near the surface before adhering to the base material (hereinafter referred as "surface salt concentration") is preferably at least 50 mol %, more preferably at least 60 mol %, further more preferably 70 mol % or still more preferably at least 80 mol %. The adhesiveness of the particles is low if the surface salt concentration before adhering to the base material is too low.

The ultimate surface salt concentration of the water-absorbent resin particles in the absorbent composite after adhering to the base material is not particularly limited, but it is preferably 90 mol % or less, more preferably 80 mol % or less or still more preferably 60 mol % or less. It is advantageous that the surface salt concentration of the water-absorbent resin particles in the final composite is low because it reduces stickiness of the product that is exposed to humid air. This is also extremely desirable because the dispersibility of aqueous solution in the absorbent composite can thus remain high even if the particles contact each other during swelling after the composite absorbs an aqueous solution. To maintain a high absorption capacity, it is necessary to increase the salt concentration of the absorbent resin particles as a whole, but to maintain high liquid dispersibility in the composite, it is better to have a lower salt concentration near the surface. That is, it is desirable that the surface salt concentration is reduced while the internal salt concentration is increased. Specifically, the surface salt concentration is preferably at least 10 mol % lower, more preferably at least 20 mol % lower or further more preferably at least 30 mol % lower than the salt concentration at the center of the resin. "Near the surface" means the outer layer of a thickness of about 1 μm from the surface of the resin. It is desirable to adjust the salt concentration near the surface at the same time as the resin is adhered to the base material because a high level of balance between adhesiveness and absorbability can thus be obtained.

The water-absorbent resin normally consists of acid groups such as carboxyl groups, sulfonic acid groups and neutralized salts thereof, and basic groups such as amino groups and neutralized salts thereof and the like. The surface salt concentration of the water-absorbent resin particles means the proportion of neutralized groups of the surface part of the water-absorbent resin particles. In the present invention, the salt concentration near the surface of the resin particles can be determined by microscopic ATR, a method of infrared absorption analysis. Since ATR generally provides structural information about the surface layer to a depth of 1 μm, the degree of neutralization of the resin particle surfaces can be measured directly by microscopic ATR. The degree of neutralization of the inner part is measured by microscopic ATR after cutting open the resin and exposing the center by using an ultramicrotome (Reichert, Ultracut N). A Bio-Rad FTS-575 is used for measurement.

A polyacrylic acid water-absorbent resin is used as an example below. In order to determine the ratio of carboxylic acid and carboxylate, the peak area ratio (1695/1558 cm$^{-1}$) of peak area at 1695 cm$^{-1}$ (carboxylic acid v C=O base materialline 1774-1616 cm$^{-1}$) and peak area at 1558 cm$^{-1}$ (carboxylate v COO$^-$ base materialline 1616-1500 cm$^{-1}$) was calculated. The ratio is determined based on calibration curve that was prepared by measuring standard samples of partially crosslinked polyacrylic acid neutralized by 10 mol %, 30 mol %, 50 mol %, 70 mol %, 90 mol % or 100 mol % with ammonia.

(Surface Strength)

The water-absorbent resin particles before being adhered to the base material preferably have a surface strength of 0.1 to 5.5 N, more preferably 0.1 to 5 N, further more preferably 0.2 to 4 N or still more preferably 0.2 to 3 N. A surface strength is a parameter indicating the tendency to be deformed of the particle surfaces. When water-absorbent resin particles that have absorbed to certain times and have swollen are placed in a container and subjected to load, the gel moves and deforms so as to fill in the gaps between the water-absorbent resin particles, which are packed in the container with gaps between them. Since surface strength is the elastic module of the water-absorbent particles when they have absorbed liquid and become to their actual volume, it signifies the degree of interaction between gel particles and the tendency to be deformed on their surface. If the surface strength of the water-absorbent resin particles is high, it means that the water-absorbent resin particles are not easily deformed. If the particles are not easily deformed, a strong negative force against swelling is generated when the water-absorbent resin particles absorb liquid, and thereby decrease the absorption capacity. If the surfaces are not easily deformed, the area of adhesion between the resin and base material is reduced, and thereby yield detachment of the particles from the composite. The surface strength of the water-absorbent resin particles of the present invention is determined as follows.

Equipment: Shimadzu Autograph AG-1

Sample: 0.10 g of water-absorbent resin particles are weighed precisely and distributed uniformly on the bottom of a cylindrical container with a height of 50 mm and an inner diameter of 20.5 mm on the bottom of which is pasted a nylon sheet with a pore size of 75 μm. A Petri dish with a diameter of 50 mm is prepared and filled with 0.90 g of saline, and the cylindrical container containing the water-absorbent resin particles is left in the Petri dish to absorb and swell for 1 hour.

Measurement: 1 kN load cell is prepared, and a cylindrical shaft with a diameter of 19.7 mm is attached to it. The measurement range is set at 0.2 kN, and starting from the height at which there is no load on the load cell, it is set to descent at a fixed rate of 0.6 mm/minute. The pressure loaded on the load cell is measured over time. Surface strength is indicated by the load (N) at the point when the particles become actual volume. The actual volume of the water-absorbent resin particles was calculated based on the relative density of saline of 1.010 g/cm$^3$ and the relative density of the water-absorbent resin particles.

(Absorption Capacity)

In the present invention, the average absorption capacity of the water-absorbent particles in the composite must be at least 50 g/g, and is preferably at least 60 g/g more preferably at least 70 g/g.

In the water-absorbent resin particles of the present invention, moreover, the absorption capacity of the water-absorbent resin under load or pressure of 0.8 psi is preferably at least 20 g/g, more preferably at least 25 g/g or still more preferably at least 30 g/g. It is desirable for the water-absorbent resin particles to have a high absorption capacity because the quantity of water-absorbent resin particles used can then be reduced.

In the present invention, the absorption capacity of the water-absorbent resin particles means the amount of 0.9% saline that the water-absorbent resin particles can absorb by freely swelling under the condition that no loads is loaded on the water-absorbent particles. The absorption capacity of the water-absorbent resin particles is measured by the following method.

0.05 g of water-absorbent resin particles are placed uniformly in a nonwoven pouch similar to a tea bag (60×40 mm), and immersed in 0.9% saline at 23° C. 180 minutes later, the tea bag is taken out, and obliquely-suspended with its corners fixed for 10 minutes to drip, and the weight is measured. A same measurement is carried out for the sample without water-absorbent resin particles, and the measured weight is given as the blank. The absorption capacity is calculated using (Formula 4). The value is measured 3 times, and the average of them is given as the absorption capacity.

Absorption capacity of water-absorbent resin particles (g/g)={(weight of tea bag after absorption)−(weight of blank tea bag after absorption)−(weight of water-absorbent resin particles)}/(weight of water-absorbent resin particles). (Formula 4)

The absorption capacity under pressure of the water-absorbent resin particles of the present invention is measured as follows. 0.02 g of water-absorbent resin particles are placed in an acrylic resin tube with a inner diameter of 25 mm and a height of 30 mm having a 250-mesh nylon nonwoven fabric on the bottom, a smoothly moving cylinder is placed in the tube to make it the measurement device, and the weight is measured. Load is applied by placing a 278.33 g load (corresponding to 0.8 psi) on top of the cylinder of the measurement device, and the device is placed in a 120 mm Petri dish containing 60 g of 0.9% saline. After 60 minutes the measurement device is taken out and left for 3 seconds on a Kimtowel to drain off water, the device is weighed after unloading the load, and the absorption capacity under pressure is calculated according to (Formula 5).

Absorption capacity (g/g) of water-absorbent resin particles under load=(weight (g) of the device after absorption−weight (g) of the device before absorption)/(weight of water-absorbent resin particles) (Formula 5)

An absorbent composite with a tensile breaking strength of 0.6 (N/20 mm) or more comprising water-absorbent resin particles with an absorbent capacity of 70 g/g or more and an absorbent capacity under load of 0.8 psi of 20 g/g or more is desirable for sanitary material applications such as disposable diapers because it exhibits excellent absorption properties both under no pressure and under pressure. Preferably the water-absorbent composite consists of water-absorbent resin particles and paper and/or fabric, and more preferably each water-absorbent resin particle is arranged with a space between each other so that blocking of the particles does not occur, and still more preferably 90 wt % or more of the water-absorbent resin particles adhere to paper and/or fabric. Water-absorbent resin particles having an absorption capacity under no pressure of 70 g/g or more and an absorption capacity under load of 0.8 psi of 20 g/g or more can be obtained by the following methods. They can be obtained by polymerizing unsaturated carboxylic acid monomers 70% or more of which are acrylic acid, wherein 50% or more of the carboxyl groups are neutralized as ammonium salts and 70% or more of the total monomers are neutralized. In this case, monomers include a compound having 2 or more unsaturated groups in one molecule that acts as a crosslinking agent in the amount of 0.0005 to 0.1 mol % of the total monomer components. 0.1 to 3 weight parts of a compound having two or more functional groups that can react with carboxyl groups may be used during any step either before or after polymerization. Radical polymerization is carried out by using a redox-type initiator, and the radical polymerization initiator is used in the amount of 0.005 to 0.5 mol % of the amount of unsaturated monomers. Reducing agent is used in the amount of 0.0001 to 1 g per 1 mole of monomer. Heating is also carried out as necessary under the conditions that fulfill (Formula 6) below. This heating is preferably carried out on the absorbent composite during the manufacturing process of it rather than on the water-absorbent resin particles alone.

$Y=-1.6X+345$ (Formula 6)

(wherein Y is the heating time (minutes) and X is the heating temperature (° C.)).

As the water-absorbent resin particles obtained in this way have a tendency to cause blocking, they show inferior results especially in the absorption speed and absorption capacity under pressure if they are measured by a conventional method in which the water-absorbent resin particles are in close contact with each other. However, the water-absorbent resin particles show excellent results in any of absorption speed, absorption capacity under no pressure and absorption capacity under pressure if they are measured by the above-mentioned method of the present invention in which they can maximize their absorption capability.

(Particle Size)

The weight-average particle size of the water-absorbent resin particles used in the present invention is preferably 100 to 2700 μm, more preferably 100 to 2100 μm or still more preferably 200 to 2100 μm or ideally 200 to 1400 μm. It is not preferable that the average particle size is too small from the standpoint of absorption capability. On the other hand, it is not preferable that the average particle size is too large, as it is difficult to adjust the total surface area coefficient within the desired range.

In the present invention, the particle size of the water-absorbent resin particles is determined by sieve classifying with sieves with a sieve-opening of 106 μm, 212 μm, 300 μm, 425 μm, 500 μm, 600 μm, 710 μm, 850 μm, 1000 μm, 1180 μm, 1400 μm, 1700 μm and 2500 μm. In the present invention, the particle size is determined to be the intermediate value between the values for sieve-openings in the sieves through which the particles pass and through which they cannot pass. The particle size of particles that pass through a sieve with a sieve-opening of 06 μm is determined to be 53 μm, and the particle size of particles that remains on a sieve with a sieve-opening of 2500 μm is determined to be 2700 μm. By this operation, the particles are classified into 53 μm, 159 μm, 256 μm, 362.5 μm, 462.5 μm, 550 μm, 655 μm, 780 μm, 925 μm, 1090 μm, 1290 μm, 1550 μm, 1850 μm, 2100 μm or 2700 μm.

The proportion of the water-absorbent resin particles in the composite of the present invention that pass through a sieve with a sieve-opening of 300 μm is preferably 50% or less, more preferably 40% or less. The proportion of particles that cannot pass through a sieve with a sieve-opening of 3000 μm is preferably 10% or less, more preferably 5% or less.

The particle size distribution of the water-absorbent resin particles in the absorbent composite of the present invention is closely related to the absorption capability of the absorbent composite. For example, the absorption speed tends to increase as the average particle size decrease, and the degree of swelling in the direction perpendicular to the base material and the absorption amount per unit area tend to increase as the average particle size increase. Comparing resin particles of the same weight, the area occupancy rate of the resin tends to decrease as the average particle size increases, and thus blocking of swelling is less likely to occur. The absorption speed of particles alone is too slow if the particle size is too large, but the absorption speed of large particles in the composite of the present invention is enhanced by the combination effect with fibers, thus it is preferable to use relatively large particles. From the standpoint of both absorption capacity and absorption speed, it is desirable to use both relatively large particles with a particle size of 550 μm or more and relatively small particles with a particle size of 300 μm or less, and preferably there are two or more peaks in the particle size distribution of the particles in the composite. The particle sizes of the two peaks preferably differ by a factor of 2 or more, more preferably 3 or more or still more preferably 4 or more. If there is a difference in the particle size, the particles are packed as close as closest packing, and the large particles and the small particles do not contact with each other when they swell, and each particle will be able to maximize its absorption capability.

(Large Particles)

Large particles are preferably used in the absorbent composite of the present invention. Large particles are particles with a particle size of 550 to 2100μ. Larger particles are more desirable for purposes of increasing the absorption capacity of the absorbent composite per unit area, but the absorption speed become very slow if the particles are too large, and they may cause a problem of pain or the like by sticking out when they are used in the absorber of a hygiene product. Consequently, the size of the large particles is preferably 655 to 1850 μm, more preferably 780 to 1550 μm or still more preferably 925 to 1290 μm.

Since the absorption speed of these large particles is greatly affected by their shape, they are preferably pulverized amorphous particles produced by a method comprising pulverization, and/or aggregated particles produced by reverse-phase suspension polymerization. Particles other than pulverized amorphous particles or aggregated particles whose specific surface area (surface area/volume) is smaller than these may cause a reduction in the absorption speed.

Aggregated particles used herein means aggregate formed by aggregation of two or more particles with an average particle size in the range of 10 to 550 μm (hereinafter refers as primary particles). The particle size distribution of the primary particles does not need to be uniform, and the primary particles may include particles with a particle size of exceeding 550 μm or below 10 μm. That is, it is sufficient that the average particle size of the primary particles before aggregation be in the range of 10 to 550 μm. It is desirable that the average particle size of the primary particle is small because it increases the absorption speed of the large particles. On the other hand, it is desirable that the average particle size of the large particle is large because it reduces the particle surface area after swelling, thereby reducing the contact area of the water-absorbent resin with the external and preventing the users from feeling coldness of the water-absorbent resin. This is also desirable because it prevents swollen resin from penetrating through the sheet between the absorbent composite and the body to the skin even when the swollen primary particles become detached. Consequently, the most desirable average particle size of the primary particles is 200 to 500 μm.

The salt concentration near the surface of the large particles is preferably 10 mol % or more, more preferably 20 mol % or more, or still more preferably 30 mol % or more lower than the salt concentration at the center of the resin. Where pulverized amorphous particles are used, it is particularly preferable to increase the absorption speed by transporting water into the inside of the particles using ion osmotic effect caused by a salt concentration difference between the surface and the center, because the specific surface area of large particles is smaller than that of aggregated particles. It is also preferable to crosslink the surface of the particles in order to reduce the blocking effect that blocks liquid from dispersing into the inside of the particles caused by swelling of the particle near its surface during absorption. When aggregated particles are used as the large particles, the absorption speed may be reduced by gel blocking effect of the constituent primary particles that prevent water from penetrating into inside of the large particles. Consequently, it is desirable to reduce the gel blocking effect by making the surface of the swollen particle dry by reducing the salt concentration near the surface of the primary particles, or by crosslinking near the surface of the primary particles.

In the absorbent composite of the present invention, the absorption capacity and absorption speed of the absorbent composite are preferably adjusted by using both large particles and other water-absorbent resin particles, and in this case the average particle size of the mixed resin particles is preferably in the range of 10 to 2700 μm, more preferably 100 to 1000 μm or still more preferably 200 to 550 μm. When resin particles other than large particles are included in the composite of the present invention for the purpose of improving absorption speed, it is desirable to include many water-absorbent resin particles with relatively small particle size. In this case, the content of particles that pass through a sieve with a sieve opening size of 300 μm is preferably 10 to 50 wt % based on the total water-absorbent resin particles in the absorbent composite. If the water-absorbent resin particles are too small the absorbent capability will be lower, therefore the content of water-absorbent resin particles with a particle size of less than 100 μm is preferably 10 wt % or less. More preferably, the content of water-absorbent resin particles with a particle size of less than 212 μm is preferably 10 wt % or less.

6. Base Material

A base material in the present invention means a material that can maintain a sheet form.

(Material)

In the present invention, the base material may be of any material that is in sheet form, but preferably it is of paper and/or fabric. Paper used herein means paper broadly defined by JISP0001, and fabric is a general term for sheet-shaped fiber products as defined by JISL0206. Fabric is classified into woven fabric, knitted fabric, lace, mesh and nonwoven fabric depending on the means of forming the sheet. Woven, knitted or nonwoven fabric is preferably used in the present invention and nonwoven fabric is particularly preferable. Paper and/or fabric are desirable because they have morphologic stability, unlike pulp and other short fibers. Nonwoven fabric is defined by JIS L 0222.

The material of the base material is not particularly limited, and more than one material may be combined. The base material fibers may be natural fibers or synthetic fibers, and multiple types of fibers may also be combined. The fibers may be either long or short. They may also be treated to increase strength or hydrophilicity. Hydrophilic fibers are more desirable than hydrophobic fibers from the standpoint of liquid absorption and water permeability. Continuous long fibers are also desirable than short fibers because they are excellent in liquid permeability.

Of the hydrophilic base materials, a cellulose base material is particularly desirable. In the present invention, a cellulose base material means a fabric and/or paper that are made mainly from cellulose, and a fabric and/or paper made of cellulose fiber, especially a nonwoven cellulose fabric, is desirable. A cellulose derivative obtained by esterification or etherification can be used as the cellulose. It may also be mixed with other fibers. Kinds of cellulose include natural fibers such as cotton and hemp, and reclaimed fibers such as rayon, polynosic, Lyocell and cupra and the like. A reclaimed fiber, especially reclaimed fiber made from the annual cottonseed, is preferred.

(Shape)

The shape of the base material is not particularly limited, and the thickness is preferably 0.001 mm to 1 cm, more preferably 0.01 mm to 5 mm, still more preferably 0.05 mm to 3 mm or ideally 0.1 mm to 1 mm. The weight is preferably 0.1 $g/m^2$ to 1 $kg/m^2$, more preferably 0.5 $g/m^2$ to 500 $g/m^2$ or still more preferably 1 $g/m^2$ to 100 $g/m^2$. From the standpoint of strength, the material that is too thin or too light is not preferable.

(Tensile Breaking Strength)

In the present invention, the tensile breaking strength after absorption of saline is preferably at least 0.6 N/20 mm, more preferably 0.6 to 5000 N/20 mm, still more preferably 0.7 to 500 N/20 mm or yet more preferably 0.85 to 100 N/20 mm or ideally 1 to 100 N/20 mm.

In the present invention, the direction in which the strength of the material is maximum is defined as lengthwise direction and the direction perpendicular to this direction is defined as crosswise direction, and the strength is preferably within the aforementioned range in the crosswise direction (that is, both in the lengthwise direction and in the crosswise direction).

In the present invention, the tensile breaking strength of the base material after absorption of saline means the tensile breaking strength that is measured after having made the base material absorb saline. A sanitary material sometimes continues to be used after having absorbed liquid without being changed. It may also be required to absorb liquid multiple times after having once absorbed liquid. If the absorber continues to be used after having absorbed liquid, it becomes to be in the same situation where it is under load with keeping water in it. If the base material breaks due to the load, the liquid permeability and liquid dispersion properties are adversely affected, and the absorption capability is adversely affected. It is preferable that the base material maintains its strength even after having absorbed saline from the standpoint of durability of the absorber. It is preferable that the base material has high strength, because it is disadvantageous to have low strength when the manufacturing process of the composite includes a process in which the base material absorbs water. However, the absorption capability does not further improved by using an excessively strong base material.

The tensile breaking strength after absorption of saline is determined as follows.

Sample: 15 cm×2 cm rectangular base material (various kinds with different directions are prepared)

Equipment: Tensile Tester (Shimadzu Autograph)

Methods: 700 g of 0.9% saline is taken in a 1 L beaker, and the base material is immersed therein for 10 minutes. The base material is pulled out and left on a Kim towel for 1 minute, then is fixed on the equipment at the points 2.5 cm inside from each edge so that the space between the points to be pulled is 10 cm, and the base material is pulled at a speed of 10 mm/minute until it breaks. The force at the time of break is recorded, and the maximum value is determined to be strength N/20 mm. If the base material has different strength depend on measurement direction, measurements are carried out for some different measurement directions.

(Absorption Capacity, Absorption Speed)

Absorption capacity and absorption speed are indicators of the hydrophilicity and liquid permeability of the base material. These are explained below.

In the present invention, the absorption capacity of the base material means the factor by which the base material increases in weight after having absorbed 0.9% saline over 60 minutes, and is specifically measured as follows.

A circular piece with a diameter of 59.5 mm is cut out from the base material and weighed, and a wire is passed through it 1 cm inside from the edge. 500 g or more of saline is provided at 23° C. in a 1 L beaker, and the base material is immersed in the saline together with the wire. After 60 minutes, the base material is taken out from the saline together with the wire, and suspended for 10 minutes without contacting with anything else. After 10 minutes, the wire is removed and the total weight of the wet base material and water adhering thereto is measured.

The absorption capacity of the base material is shown by (Formula 7).

$$\text{Absorption capacity of base material (g/g)} = \text{weight after absorption (g)/weight before absorption (g)} \quad \text{(Formula 7)}$$

In the present invention, the absorption capacity of the base material is preferably at least 6 g/g and not more than 200 g/g, more preferably at least 8 g/g and not more than 100 g/g, still more preferably at least 10 g/g and not more than 50 g/g or ideally at least 12 g/g and not more than 30 g/g.

Because in the absorbent composite the fiber has a faster absorption speed than the water-absorbent resin particles, the base material absorbs in the early stage of absorption and the water-absorbent resin particles absorbs in the late stage of absorption. It is desirable for the base material to have a higher absorption capacity because this means a faster liquid absorption speed in the early stage. Because the base materials generally absorb by capillary action, the liquid may be released under load, causing humidity during use. However, if the resin particles adhered with the fibers of the base incorporated therein, the water-absorbent resin absorbs liquid by capturing liquid from the base. As a result, there is little rewetting under load or steaminess during use.

In the present invention, the absorption speed of the base material means the speed at which the base with a width of 2 cm absorbs 0.9% saline in perpendicular direction.

The absorption speed of the base material is preferably at least 0.35 mg/sec and not more than 100 mg/sec, more preferably at least 0.45 mg/sec and not more than 50 mg/sec, further more preferably at least 0.55 mg/sec and not more than 30 mg/sec or still more preferably at least 0.65 mg/sec and not more than 10 mg/sec.

Specifically, the absorption speed of the base material is measured as follows.

Sample: 10 cm×2 cm rectangular base
2 or more samples are prepared with different directions if it has a lengthwise direction and a crosswise direction.
Equipment: Electronic scale, 90 mm dia. Petri dish
Methods: The Petri dish is placed on the electronic scale, and the base material is suspended vertically 10 cm above the Petri dish. The Petri dish is taken out from the scale, and filled with 60 g of 0.9% saline which was measured out with another scale. The Petri dish is replaced on the scale with the bottom of the base material being held by hand not to be in contact with the saline, and the scale is set to 0. The base material is carefully immersed in the saline, and the value of the scale is measured over time. The time (seconds) and the absolute value (mg) of the scale are plotted on a graph, and the gradient (mg/sec) between 120 and 240 seconds is determined to be the absorption speed. If the base material has directions, several measurements are carried out for different directions, and the fastest value is determined to be the absorption speed.

It is preferable that the absorption speed of the base material is different depend on directions. This is because in this case, liquid permeability is excellent in a particular direction and liquid disperses easily in the particular direction, thus the balance of absorption can be controlled in the absorber.

(Ratio of Tensile Breaking Elongation and Strength in the Lengthwise Direction and in the Crosswise Direction)

When the base material has directions, the strength and elongation are different depend on direction. As mentioned above, in the present invention, the direction in which the strength is maximum refers to as the lengthwise direction and the direction perpendicular to the lengthwise direction refers to as the crosswise direction.

The ratio of tensile breaking strength in the length direction and the crosswise direction is preferably at least 1.2:1, more preferably at least 1.5:1 and still more preferably at least 2:1, but not more than 10:1.

The ratio of tensile breaking elongation in the lengthwise direction and crosswise direction is preferably at least 1:1.2, more preferably at least 1:1.5 and still more preferably at least 1:2, but not more than 1:10. The elongation and strength of the base material can be determined in the same way as the strength of the base material after having absorbed saline by tensile testing with the base material in a dry state, not immersed in saline. The tensile test is continued until the base material breaks, and the force at which it exhibits maximum strength is determined to be the strength of the base material and the elongated distance at that time is determined to be the elongation.

(Contact Angle)

The base used in the present invention is preferable a non-woven fabric with a contact angle of 130° or less.

In the present invention, the contact angle is defined as the angle formed after a 44% aqueous ammonium polyacrylate solution with a viscosity of 74 cps is made be in contact with the base material at room temperature for 10 minutes. The angle is measured using a contact angle meter (CA-X150) made by FACE (Kyowa Interface Science). The solution is prepared by adjusting the viscosity of a 44% aqueous ammonium polyacrylate solution (70 to 110 cp) from Wako Pure Chemical with water. Viscosity is measured with a rotating disc viscometer.

The contact angle is preferably 130° or less, more preferably 120° or less, still more preferably 110° or less or ideally 100° or less. The affinity between the base material and water and the affinity between the base material and water-absorbent resin increase as the contact angle decreases, and thereby increase the absorption capability and adhesiveness.

7. Method for Manufacturing Absorbent Composite

The absorbent composite of the present invention is made from water-absorbent resin particles and a base material, and is preferably manufactured by a method including a step of adhering the water-absorbent resin particles to the base material.

The adhering method is not particularly limited, and may be one that fulfills the conditions mentioned above.

Examples of adhering methods including methods in which the water-absorbent resin is entangled with the base material and methods using adhesives, and a preferred method is one in which the water-absorbent resin and/or the base material is made to absorb 10 to 3000 weight parts of water per 100 weight parts of water-absorbent resin, and the water is then removed while the water-absorbent resin is in contact with the base material. The amount of water is preferably 20 to 2000 weight parts or more preferably 50 to 1000 weight parts per 100 weight parts of water-absorbent resin particles. This method of adhering is preferred because it does not require an adhesive, which becomes an impurity. In this method some of the fibers are also incorporated into the water-absorbent resin, which is desirable from the standpoint of absorption speed and absorption capacity. It is preferable to use more water, as it increases adhesiveness, but using too much water is inefficient because it takes longer to dry.

The water to be absorbed may contain impurities. Examples of impurities include cations such as sodium ions, ammonium ions and water-soluble organic compounds such as iron ions, and chlorine ions and other anions, and acetone, alcohols, ethers and amines. An acidic or basic substance may be used to adjust the pH of the water-absorbent resin and/or absorbent composite. From the standpoint of contact between the water-absorbent resin and base material and absorption capability, it is desirable to use ion-exchange water or distilled water without impurities alone.

It is preferable to dissolve and/or disperse a substance having a deodorant or other function in the water to thereby functionalize the resulting absorbent composite. Examples of deodorants that can be used in this case include organic and inorganic deodorants. When using a deodorant that is insoluble in water, it is desirable to use a dispersant or surfactant as necessary. An inorganic deodorant can also be dispersed in water without using a dispersant by reducing the particle size to the nanometer level, therefore it is preferable to use a fine-particle inorganic deodorant without a dispersant.

The wetting method is not particularly limited, and examples include immersing in a water bath, spraying with water, making be in contact with a wet body, exposing to humidification and the like. Of these, the water spraying method is most preferred because it is industrially simple and easy to adjust the water content. It is preferable to use a water spraying system which provides a uniform water content in the fabric or other base material. If the water content varies widely with location of the base material, the particle size of the resin in the dried water absorbent composite become nonuniform, as the amount of water the water-absorbent resin particles absorb after they come in contact with the base material and before the drying step starts differ by location, and the foaming behaviors caused by removal of water in the drying step will differ by location The texture of the absorbent composite with nonuniformly-sized resin particles may not good.

In wetting the base material and adhering to the water-absorbent resin particles, the water content of the base material is preferably in the range of 50 to 500 wt %. It is preferable to increase a water content to increase the adhesiveness between the water-absorbent resin particles and the base material, but if the water content is too large, the drum used in manufacturing method mentioned below will be covered with large amount of water and it will cause the problem that the water-absorbent resin particles adhere to other parts of the drum than the dimples. Of course, if the water content is too low, adhesiveness between the base material and the resin will be adversely affected. Therefore, the water content is preferably in the range of 50 to 200 wt % or more preferably 80 to 150 wt %.

In order to wet the base material, the water-absorbent resin particles may contain water for adhering, but since this makes the water-absorbent resin more likely to adhere to other objects than the base, the water-absorbent resin particles before adhering are preferably dried to the extent that they do not adhere to other objects or to other resin particles. The water content of the water-absorbent resin particles in this case is preferably 1 to 50 wt % or more preferably 5 to 30 wt %.

Examples of contacting methods include scattering the water-absorbent resin particles on the base material from above, holding the water-absorbent resin particles in the dimples on the surface of a drum followed by transferring the water-absorbent particles in the dimples to the surface of the base material, and filling the inside of a drum roll having surface dimples with water-absorbent resin particles followed by expelling the particles from the drum and putting them onto the base material with pressure. A Preferred method is the one that allows the water-absorbent resin particles to be arranged so that they do not contact with each other after swelling, because it maximize the absorption capability of the water-absorbent resin particles.

Any method can be used for removal of water. Examples include drying by heating, blowing dry air or nitrogen, vacuum drying, freeze drying, azeotropic drying, fluid drying, microweb drying and the like, and drying by heating is preferred. The heating conditions are preferably 1 to 1000 seconds at 70 to 350° C., more preferably 1 to 1000 seconds at 100 to 340° C., still more preferably 1 to 1000 seconds at 120 to 330° C. or ideally 1 to 1000 seconds at 150 to 300° C. The higher the temperature the shorter the drying time, but the absorption capability of some types of resin may be adversely affected by long-term heating at high temperatures. Surface treatment such as crosslinking may be applied at the same time as drying. Removal of water may be carried out at any stage before completion of the final product, and is preferably carried out shortly after wetting in order to avoid deterioration of the water-absorbent resin.

(Preferred Method for Manufacturing the Absorbent Composite)

One desirable example of a method for manufacturing the absorbent composite of the present invention is explained below.

FIG. 1 is an explanatory diagram of a desirable manufacturing device for manufacturing the absorbent composite of the present invention. The base material supplied from the original fabric roll (a) is made into wet base material (c) using a device such as a water sprayer (b). Then resin particles are blown onto one surface of the wet base material from a rotating drum for adhering resin particles (e1) in the dimples on which resin particles (f) supplied from resin particle feed part (d1) are placed. Then resin particles are blown onto another surface of the wet base material from a rotating drum for adhering resin particles (e2) in the dimples on which resin particles (f) supplied from resin particle feed part (d2) are placed. Then small-sized resin particles are dispersed uniformly from small resin particle feed part (i) to adjust the absorption capabilities of the absorbent composite, and the base material with resin particles adhere to both surfaces is dried by passing through drying part (g) to give a composite with resin particles strongly adhere thereto.

In the method described above, the structure of the rotating drum for adhering resin particles which arranges the water-absorbent resin particles on the base material is important. The drum surfaces have, at pre-determined positions, multiple dimples into which the water-absorbent resin particles can be inserted. These dimples are preferably arranged so as to reduce the probability that the water-absorbent resin particles come in contact with each other. There is an optimal arrangement of dimples that maximizes the absorption capability of the absorbent composite. This is an arrangement whereby spaces are provided between adjacent resin particles to allow them to swell by absorption, and whereby more water-absorbent resin particles can be arranged on the base material.

In this manufacturing method, the outer diameter of the opening of the dimples on the surface of the drum is preferably 1 to 3 times, more preferably 1.2 to 2 times the maximum diameter of the supplied water-absorbent resin particles. The outer diameter of the opening of the dimple on the drum as used in this explanation means the largest value of the distances between any two points on the peripheral border of the opening on the surface of the drum.

If the outer diameter of an opening is too large, it is difficult to operate stably, as multiple water-absorbent resin particles may be inserted into a single dimple or the water-absorbent resin particles once inserted in the dimple will be more likely to fall out of the dimples. On the other hand, if the outer diameter of the opening is too small, water-absorbent resin particles in the dimples may be removed in removing water-absorbent resin particles that adhere to other parts than the dimples due to static electricity or the like even when the particles are held into the dimples with sucking force.

Regarding the structure of the dimple, the peripheral border on the surface of the drum surface may take any form including non-angular shape such as circular and oval, angular shape such as triangular, rectangular and pentagonal and infinite shape. A definite non-angular or angular shape is preferable from the standpoint of manufacturing the drum, and a non-angular shape is desirable from the standpoint of manufacturing the drum and inserting and removing the particles from the dimples.

Regarding the structure of the dimple from the peripheral border on the surface of the drum towards the inside of the drum, the dimples may have the same space from the surface to the inside, or may be wider on the inside than on the surface, or may be narrower on the inside than on the surface. From the standpoint of ease of insertion and removal of the water-absorbent resin particles, it is desirable that the space of the dimples be narrower on the inside than on the surface.

The depth of each dimple on the drum is preferably 0.3 to 2 times, more preferably 0.5 to 1.5 times or still more preferably 0.7 to 1.2 times the average particle size of the water-absorbent resin particles supplied to the drum. If the dimples are too shallow, water-absorbent resin particles in the dimples may be removed in removing water-absorbent resin particles that adhere to other parts than the dimples due to static electricity or the like even when the particles are held into the dimples with sucking force. If the dimples are too deep, multiple water-absorbent resin particles may be inserted into one dimple, making it difficult to adjust the amount of resin adhere to the resulting absorbent composite, and it may also be more difficult to remove the water-absorbent resin particles after insertion, interfering with stable operation.

The drum used in this manufacturing method preferably has a hole at the bottom of each dimple on the surface of the drum through which the gas which is used to blow out the water-absorbent resin particles can pass. The inner diameter of the hole is preferably smaller than the size of the small-sized particles of water-absorbent resin supplied to the drum. If the holes are larger than the small-sized particles, particles smaller than the holes may pass through the holes into the inside of the drum instead of being blown onto the base material, and may be accumulated in the drum and cause problems for operation. The holes may be of any structure as long as they can let the gas through effectively from the inside of the drum to the outside of the drum. In order to avoid clogging of holes with the water-absorbent resin particles, it is preferable that the holes have the structure wider towards the inside of the drum.

In inserting the water-absorbent resin particles into the drum, it is preferable that the particles are inserted under suction condition by depressurizing the inside of the drum. The pressure difference between the outside and inside of the drum in this case is preferably in the range of 0.01 to 500 Torr. If this pressure difference is too small, the particles inserted into the dimples fall out easily. On the other hand, if it is too large, too many particles enter the dimples and they are hard to expel. Therefore, this pressure difference is preferably in the range of 0.05 to 100 Torr, more preferably 0.1 to 50 Torr or still more preferably 0.5 to 5 Torr. This method with suction is extremely desirable because it not only increase the probability of the water-absorbent resin particles being inserted into the dimples, but also can prevent water-absorbent resin particles in the dimples from falling out in removing particles adhering to other parts than the dimples on the drum after inserting the particles into the dimples until blowing out them onto a hydrophilic fabric support.

For this manufacturing method, it is preferable to provide a system for removing the water-absorbent resin particles that adhere to other parts of the drum than the dimples after inserting the water-absorbent resin particles into dimples on the drum until blowing out them onto the base material. The removal method is not particularly limited, and examples include sweeping with a brush, blowing a gas and using vibration. Of these methods, blowing a gas is most desirable.

It is preferable to provide a device for removing static electricity from the drum, because the drum generates static electricity which destabilize the movement of the water-absorbent resin particles during operation.

It is preferable to apply the water-absorbent resin of various particle sizes to adjust the total surface area coefficient and the like after having arranged the large particles with large particle size using the drum. These particles may be applied to only one surface, or may be applied to the both surfaces of the fabric by reversing the fabric followed by applying the particles to another surface as well. To avoid detachment of the particles, it is desirable to once again apply water to the base material before said application of the particles. The method for applying particles is not particularly limited and is preferably one that can apply them uniformly.

It is preferable to convey the base material in this manufacturing method. The method of conveying the base material in this case is not particularly limited. Examples of the method of conveying the base material include those in which the base material is conveyed without any support from above or below and those in which the base material is conveyed along with a conveyor belt or other support that supports it from below. When the water-absorbent resin particles adhere to both surfaces of the base material, it is preferable to introduce a conveyor belt system for the step to convey the surface of the base material to which the particles adhere later under the surface of the drum for adhering. This is because it can prevent resin already adhering to the reverse surface of the base material from falling off when the water-absorbent resin particles are being blown out from the drum. It is also desirable to use a conveyor belt system during the final step of removing water and drying. This is because it can minimize the shrinkage of the base material that may occur during removing water from and drying the base material.

It is preferable that the water-absorbent resin particles used in this manufacturing method have a high salt concentration on the particle surfaces because this results in stronger adhesion when they are blowing out onto the base material. However, it is not preferable that the salt concentration of the surface is too high in the final product. That is, it is desirable to adjust the salt concentration of the particle surface of the water-absorbent resin particles after having adhered the water-absorbent resin to the base material. From the standpoint of productivity, it is better to adjust the salt concentration simultaneously with the drying step rather than separately after the drying step. The salt concentration of the particle surfaces is preferably at least 10% less, more preferably at least 20% less or more preferably at least 30% less compared to the concentration before the treatment.

8. Performance of Absorbent Composite (Absorption Capacity)

In the present invention, the absorption capacity of the absorbent composite means the amount of 0.9% saline absorbed during 3 hours of free absorption. Specifically, a circular absorbent composite with a diameter of 59.5 mm is prepared, and the absorption capacity is measured by the same methods used to measure the absorption capacity of the base material. When there are water-absorbent resin particles that do not adhere or when detachment of the particles has occurred, the water-absorbent resin particles are collected by filtration and left for 10 seconds on a Kimwipe to remove excess water, and count their weight into the measurement. In measuring the capacity of the absorbent composite in which almost 50 wt % of the water-absorbent resin particles do not adhered, the absorbent composite is placed in a T-Bag and measured according to the method for measuring the absorption capacity of the water-absorbent resin particles.

The absorption capacity of the absorbent composite is preferably at least 40 g/g, more preferably at least 45 g/g or still more preferably at least 50 g/g.

(Absorption Amount Per Unit Area)

Absorption amount per unit area is important as an indicator of the absorption capability of the absorbent composite. Absorption amount per unit area is calculated according to (Formula 8) based on the measurement results above.

$$\text{Absorption amount per unit area (g/cm}^2\text{)} = \text{(total weight after absorption (g)} - \text{weight of the absorbent composite (g))/area of the absorbent composite (cm}^2\text{)} \quad \text{(Formula 8)}$$

It is preferable that the absorption amount per unit area is high, and it is preferable to be not less than 0.4 g/cm$^2$, more preferably not less than 0.7 g/cm$^2$, or further more preferably not less than 1 g/cm$^2$.

(Absorption Capacity Under Pressure)

The absorption capacity of the absorbent composite of the present invention under pressure is represented as the amount of 0.9% saline absorbed during 3 hours of absorption under load. Specifically, it is measured as follows using a circular absorbent composite with a diameter of 59.5 mm.

The measurement device is explained roughly with reference to FIG. 2. As shown in FIG. 2, the measurement unit comprises scale 1, container 2 placed on the scale 1, outer air suction pipe 3, conduit 4, glass filter 6 and measurement part 5, which is placed on glass filter 6. Container 2 has opening 2a at the top and opening 2b on the side. Outer air suction pipe 3 is inserted into opening 2a, while conduit 4 is attached to opening 2b. Container 2 also contains a predetermined amount of saline 12. The lower end of outer air suction pipe 3 is immersed in saline 12. Glass filter 6 is formed with a diameter of 70 mm. Container 2 and glass filter 6 are connected to each other via conduit 4. The position of glass filter 6 is adjusted so that its height to be the same as the lower end of outer air suction pipe 3. As shown in FIG. 3, measurement part 5 has filter paper 7, support cylinder 9 and weight 11. Advantec No. 2 with a diameter of 60 mm is used for filter paper 7. In measurement part 5, filter paper 7 and support cylinder 9 are placed on glass filter 6 in this order, with weight 11 placed inside of support cylinder 9. Support cylinder 9 has an inner diameter of 60 mm. The weight of weight 11 is adjusted so that it can apply a uniform load of 0.8 psi on absorbent composite 13. The absorbent capacity under pressure of an absorbent composite was measured using a measurement unit of this configuration. The measurement method is explained below. First, the necessary preparations were made including filling container 2 with a predetermined amount of saline 12, and inserting outer air suction pipe 3 into container 2. Filter paper 7 was then placed on glass filter 6. Concurrently, absorbent composite 13 was placed inside of support cylinder 9, and weight 11 was placed on this absorbent composite 13. Next, support cylinder 9 was placed so that its center was aligned with the center of glass filter 6. After placing support cylinder 9, the weight W (g) of the saline 12 absorbed by absorbent composite 13 was measured every 10 seconds using scale 1. The absorption capacity under pressure of the absorbent composite was determined according to (Formula 9).

$$\text{Absorption capacity under pressure of absorbent composite (g/g)} = \text{weight W (g)/weight of absorbent composite (g)} \quad \text{(Formula 9)}$$

The absorption capacity under pressure of the absorbent composite under load of 0.8 psi is preferably at least 15 g/g, more preferably at least 16 g/g or still more preferably at least 18 g/g. The absorption amount per unit area can also be determined in the same way of the absorption amount per unit area under no pressure. The absorption amount per unit area under pressure of 0.8 psi is preferably 0.1 g/cm$^2$, more preferably at least 0.15 g/cm$^2$ or still more preferably at least 0.2 g/cm$^2$.

An absorbent composite with an absorption capacity of 40 g/g or more, an absorption capacity under pressure of 15 g/g or more under load of 0.8 psi and a tensile breaking strength of 0.6 (N/20 mm) or more is highly absorbent and strong and can be used favorably in disposable diapers and other sanitary materials. The absorption capacity is preferably at least 45 g/g, more preferably at least 50 g/g or still more preferably at least 55 g/g. The absorption capacity under pressure of 0.8 psi is preferably at least 16.5 g/g, more preferably at least 18 g/g or still more preferably at least 20 g/g.

(Absorption Capacity after 1 Minute)

The absorption capacity after 1 minute is an indicator of the initial liquid absorption speed. Because in sanitary material applications such as disposable diapers, bodily fluid needs to be absorbed instantly, it is preferable to have higher absorption capacity after 1 minute. The absorption capacity after 1 minute is determined according to (Formula 10). Specifically, it is measured by the following method.

A piece with a length of 2 cm and a width of 7 cm is cut out from the absorbent composite, and weighed. A 1000 cc glass beaker is filled with 700 cc of saline. A T-Bag with a length of 80 cm and width of 70 cm is weighed, and the T-Bag alone is made to absorb water for 1 minute, centrifuged, and then weighed. This weight is divided by the weight of the T-Bag before absorption to give the absorption capacity after 1 minute of the T-Bag. A T-Bag of the same size is weighed and the absorbent composite is placed therein. In order that the T-Bag can be quickly pulled out from the liquid, a clip with a string attached is prepared and attached to the T-Bag, which is then carefully and quickly immersed in the liquid so that the fabric does not bend or twist. After 1 minute of immersion, it is quickly pulled out by pulling the string. The clip is removed, and the bag is centrifuged at 150 G for 3 minutes and then weighed. The absorption capacity after 1 minute is determined by subtracting the amount absorbed by the T-Bag from the total weight, and dividing the result by the weight of the absorbent composite before absorption. Centrifugation is initiated within 15 seconds after the absorbent composite is pulled out from the liquid.

$$\text{Absorption capacity after 1 minute (g saline/g)} = \text{(weight after centrifugation (g)} - \text{weight of T-bag (g)*absorption capacity after 1 minute of T-Bag)/weight of absorbent composite (g)} \quad \text{(Formula 10)}$$

(Bending Resistance)

The bending resistance of the absorbent composite is determined by the bending resistance D method (heart loop method) described in JIS L1096. The values of front surface and back surface are different when the particle sizes and distribution are different on the front and back, and in the present invention the value of softer one, or in other words the higher value, is determined to be the bending resistance. The bending resistance is preferably 90 mm or less or more preferably 85 mm or less.

9. Method for Using Absorbent Composite

A preferred method for using the absorbent composite of the present invention is using as a constituent element of a bodily fluid-absorbing article. The use of the composite as a constituent element of a bodily fluid-absorbing article is explained below.

(Bodily Fluid-absorbing Article)

In the present invention, the bodily fluid-absorbing article means a bodily fluid-absorbing article comprising a liquid-permeable sheet, a liquid impermeable sheet, and the absorbent composite sandwiched between them, and it includes all articles with the ability to absorb bodily fluids. There are no particular limitations on the bodily fluids absorbed in the present invention, and examples include urine, menstrual blood, mother's milk, soft stool and the like. There are also no particular limitations on the shape of the article, and desirable examples include pads, tapes, pants and the like. Examples include diapers, sanitary napkins, incontinence pads, lactation pads and the like.

When combined with a liquid-permeable sheet and a liquid-impermeable sheet, the absorbent composite of the present invention can form part of a bodily fluid-absorbing article that has a high bodily fluid-absorbing capability while being thin and lightweight. Because there is little risk of the absorber moving or slipping in the bodily fluid-absorbing article during use, moreover, it can stably absorb bodily fluid. In addition, because the proportion of water-absorbent resin is higher than that in conventional bodily fluid-absorbing articles, the amount of absorbed liquid that is released under load (rewetting) is small, and the worn part remains comfortable.

In the present invention, the liquid-permeable sheet may be anything as long as it is in sheet shape and water poured on the sheet permeates through it, and preferably it is a fabric such as that defined by JIS L0206. Fabric is classified as woven fabric, knit fabric, lace, mesh and nonwoven fabric according to the means of forming the sheet, and preferred fabric used in the liquid-permeable sheet of the present invention includes woven, knitted or nonwoven fabric and more preferred fabric is nonwoven. It is preferable to use a sheet with a low water-absorbing ability made of polyethylene, polypropylene or other polyolefin in order to reduce feel of the moisture and improve feel of the sheet against user's skin, and it is preferable to use a sheet made of polyolefin that has been given a water-permeability or hydrophilicity by treatment in order to rapidly transport bodily fluid.

A liquid-impermeable sheet in the present invention can be anything that is in sheet form and is impermeable to water. A material with good gas permeability is preferred for preventing dampness.

It is sufficient for the bodily fluid-absorbing article of the present invention to have at least a liquid-permeable sheet, a liquid-impermeable sheet and an absorbent composite sandwiched between them, but other materials may also be present between the liquid-permeable sheet and the absorbent composite and/or between the liquid-impermeable sheet and the absorbent composite. Another material may also be present outside the liquid-impermeable sheet or liquid-impermeable sheet.

Materials that can be used in this case include fibrous materials such as pulp, particulate materials such as water-absorbent resins, sheet-shaped materials such as tissue, fabric, paper, and the like. These materials may also adhere to the water-absorbent composite of the present invention. These materials may adhere with adhesive, or they may adhere directly to the water-absorbent resin particles of the absorbent composite of the present invention. A bodily fluid-absorbing article preferably includes tape or elastic for fixing the article to the user's body, gathers for preventing leakage from the side and the like.

The shape of the bodily fluid-absorbing article of the present invention may be a square or circle, a rectangle or oval or a combination of trapezoids, or may have an irregular shape. A rectangle or oval or a similar shape having a longer direction and a shorter direction (direction perpendicular to the longer direction) is desirable when it is used for a diaper, sanitary napkin, incontinence pad or the like, as they fit to the crotch of user. FIG. 4 shows an illustrative example of the shape of an absorbent composite having a longer direction. There may also be a part that serves as an overlap width for jointing the composite to another part.

Where the absorbent composite include an overlap width that does not contain water-absorbent resin thereon, it is preferable that the proportion of the water-absorbent resin and the area occupancy rate of the absorbent composite are adjusted to the desired range not counting the overlap width.

The absorbent composites may be used singly or in the combination of two or more in the articles more than one. It is preferable to use only one composite in order to make a thin product. In order to make a product with greater absorbing ability, it is preferable to use more than one. When more than one composite are used, they can be used in piles or in lines. They may also be of exactly the same shape or different shapes. To improve the absorbing capability efficiently, they are preferably overlapped only in the areas where bodily fluids are excreted to, and in order to prevent leakage, they are overlapped in the areas where leakage is likely to occur.

There are no particular limitations on the posture of the absorbent composite in the bodily fluid-absorbing article, and the absorbent composite sheet may be completely spread out, or may be wrinkled or folded.

(Folding of Absorbent Composite in Bodily Fluid-absorbing Article)

When the absorbent composite of the present invention is used as a constituent element of a bodily fluid-absorbing article, the edge of the absorbent composite is preferably folded over to prevent leakage of bodily fluid from the edge. The edge used herein means the area within 15 cm from the periphery of the absorbent composite sheet. The folded part is not particularly limited as long as it is within 15 cm from the periphery and it is preferably within 12 cm, more preferably 8 cm or still more preferably 5 cm or ideally 3 cm. In the present invention, the posture that the absorbent composite is folded over means that a part of the absorbent composite is not on the same plane of the absorbent composite, when the absorbent composite is stretched without using excess force and attached to a board with thumb tacks.

The fold may be towards the liquid-permeable sheet as shown in FIG. 5 or towards the liquid-impermeable sheet as shown in FIG. 6. When another part is on a still different plane from the first fold as shown in FIG. 7, that part is called the second fold.

The composite may be folded once, twice, or many times. Multiple folds are more effective for preventing leakage, but result in extra thickness, so the number of folds should be set so as not to detract from the shape of the composite. When multiple folds are used, their directions and angles can be determined at will. They may be alternating concertina folds as in FIG. 8, or continuous folds in the same direction as in FIG. 9. A part that has been folded once can be folded over again to form a double fold as in FIG. 10. A triple or greater fold is also possible. As shown in FIG. 11, the fold does not have to be a flat fold.

A fold along the edge of the absorbent composite prevents leakage because it has thickness and acts as a physical barrier for the dispersing liquid. Moreover, the folded part can also prevent leakage of liquid after the liquid has reached it, because the folded part has a higher absorption capability than the unfolded part.

The absorbent composite may be folded around the full circumference, or only part Where the shape of the absorbent composite has a long direction and a short direction, such as a rectangle, oval or similar shape, leakage is more likely to occur in the shorter direction, and leakage can therefore be prevented with the minimum amount of folding by folding only the long sides of the absorbent composite. In this case the absorbent composite is preferably either formed with a part for folding as in FIG. 12 A, or with slits to allow folding as in FIG. 12 B. When it is known where bodily fluid needs to be absorbed, it is effective to locate the fold on the edge near that area. In FIG. 12, the dotted area is the folded area.

The length of the folded part is not particularly limited but is preferably at least 2 cm, more preferably at least 5 cm, still more preferably at least 7 cm or ideally at least 10 cm. The longer the fold, the greater the leakage-prevention effect.

Folding may be at one location or at more than one location. The folds may be continuous, or there may be multiple folded areas with gaps between.

The folds may be of any width, but the overlapping part formed by the fold is preferably 0.1 to 100 mm, more preferably 1 to 70 mm, still more preferably 5 to 40 mm or ideally 5 to 20 mm in width. If the fold is too narrow it will have little leakage control effect, on the other hand and little advantage is gained by making it too wide.

In the present invention, when the bodily fluid-absorbing article is spread out on a flat board without excess force and the four corners are fixed with thumb tacks, the angle of folding is the angle between the plane of the bodily fluid-absorbing particle and a straight line between the point immediately before the folds leaves the plane of the bodily fluid-absorbing article and the furthest point from that plane. When there are multiple folds, only the first fold is considered. Angles of folding are shown in FIGS. 5, 6 and 11. The angle of folding is preferably greater than 0° C. and is more preferably at least 30° or still more preferably at least 60° or ideally at least 90°.

The folded part may be fixed with an adhesive. Fixing the folded part with an adhesive is desirable because it prevents slippage of the absorbent composite. The adhesive may be applied on the inside of the folded part to attach the absorbent composite to itself, or may be applied on the outside to attach the absorbent composite to the liquid-permeable sheet, to the liquid-impermeable sheet or to another member.

The absorbent composite may be folded alone, or with the other members. When the absorbent composite is folded with the other members, it is preferable that the other material is in sheet form.

(Adhesive Used in Bodily Fluid-absorbing Article)

The adhesive is preferably applied lineally in the effectively lengthwise direction or in other words in the longer direction between the liquid-permeable sheet and/or liquid-impermeable sheet and the absorbent composite. Another sheet-shaped substance may also be present between the absorbent composite and the liquid permeable sheet and/or liquid-impermeable sheet. In this case, the adhesive may be applied on the absorbent composite itself, or on another sheet, or on the liquid-permeable sheet and/or liquid impermeable sheet. In the present invention, the absorbent composite has a stable shape of a sheet, and is less likely to move or shift in the bodily fluid-absorbing article during use, thus it allows bodily fluid to be stably dispersed and absorbed. The applied adhesive serves as a barrier against the bodily fluid, thereby controls the flow of bodily fluid and allows it to disperse preferentially in the longer direction of the bodily fluid-absorbing article. Normally the bodily fluid-absorbing article has a longer direction and a shorter direction, and if the bodily fluid disperses preferentially in the longer direction, the usage efficiency of the absorbent composite is improved and bodily fluid is less likely to leak in the shorter direction.

The properties of the adhesive used herein are not particularly limited, and it may be either liquid or solid. Adhesive may be used singly, or in combination of two or more. The type of adhesive is also not particularly limited, and examples include solvent type, water dispersion type, hot melt adhesives, reactant type and the like, specifically urea resin adhesives, melamine resin adhesives, phenol resin adhesives, resorcinol adhesives, alpha-olefin adhesiveness, water-soluble polymer-isocyanate adhesives, vinyl acetate resin emulsion adhesives, acrylic emulsion adhesives, vinyl acetate resin adhesives, chloroprene rubber adhesives, nitrile rubber adhesives, SBR adhesives, natural rubber adhesives, epoxy resin adhesives, cyanoacrylate adhesives, polyurethane adhesives, acrylic resin adhesives, anaerobic adhesives, denatured silicone adhesives, inorganic adhesives, paste and the like. Because hydrophilic adhesives disperse easily, and make it difficult to control the surface of the adhesive, a hydrophobic adhesive is preferably used. A hot melt adhesive is preferably used to facilitate the manufacturing process. A hot melt adhesive refers to any adhesive that is solid at room temperature and melts and spreads by heating and consolidates and adhere by cooling, and specific examples are those containing ethylene vinyl acetate copolymer resin, polyamide, polyester, atactic polypropylene, thermoplastic elastomers or the like as principal components, with rosin resin, petroleum resin or the like as tackifiers, as well as waxes, antioxidants, inorganic fillers, plasticizers and the like.

The amount of adhesive may be any amount that provides adhesive effects. The amount of adhesive per unit length is preferably 0.000001 to 0.1 g/cm, more preferably 0.00001 to 0.01 g/cm or still more preferably 0.00003 to 0.0045 g/cm. The applied amount of adhesive per unit area of the absorbent composite is preferably 0.2 to 1000 $g/m^2$, more preferably 2.0 to 100 $g/m^2$. If too much adhesive is applied on the absorbent composite, it will impede the water-absorbent resin from swelling and decrease the absorption capability, and impair the texture. On the other hand, it is not preferable to apply too little adhesive from the standpoint of adhesive strength.

In the present invention the adhesive may be applied in a commonly used pattern such as wavy lines, dots, vertical stripes or the like. When the longer direction of the bodily-fluid absorbing article or the absorbent composite is defined as the lengthwise direction, and the shorter direction is defined as the crosswise direction, it is preferable that the adhesive is applied so as to cause liquid to flow preferentially in the lengthwise direction rather than the crosswise direction, in which leakage is most likely to occur, as it reduce leakage. Examples of shape and directionality in absorbent composites are shown in FIG. 4 with the arrows showing the lengthwise direction, but they are not limited to these examples. It is desirable to apply the adhesive in a pattern that forms barriers extending in the lengthwise direction as a method of making liquid flow preferentially in the lengthwise direction. The flow of liquid is altered by the pattern of the adhesive, as the liquid can not flow over the adhesives, when the liquid disperses to reach to the adhesive. In the present invention, an adhesive pattern that preferentially directs this alteration of flow in the direction of length rather than the direction of width is a pattern of lines extending lengthwise with spaces between them. Desirable examples of such adhesive patterns are shown in FIG. 13, but they are not limited to these examples. In FIG. 13 A, the adhesive is applied linearly in the lengthwise direction. Each line may be a straight line or may be a curved line as in FIG. 13 B. The lines may be continuous, or may be short lines as in FIGS. 13 C and D or patterns of dots as in FIGS. 13 E and F. Preferably at least 60%, more preferably at least 80% of each line is at angles of within 45° to the longer direction. 60% or 80% means the total percentage of the lengths of the straight lines that are at angles of within 45° to the longer direction relative to the total lengths of all the lines. Where the lines are curved, the overall vector of the lines is preferably at angle of within 45° to a straight line in the lengthwise direction. The lines are preferably spaced at intervals of 0.001 to 10 cm, more preferably 0.01 to 5 cm or further more preferably 0.1 to 2 cm. Helical patterns which are arranged in the lengthwise direction as shown in FIG. 13 G is also preferable. The vector of a helical pattern is preferably at an angle of within 45° to the longer direction. The vectors of each helical pattern are preferably spaced at intervals of 0.001 to 10 cm, more preferably 0.01 to 5 cm or further more preferably 0.1 to 2 cm. A single pattern may be used, or multiple patterns may be combined as shown in FIG. 13 H. A pattern of intersecting lines can also be used as in FIG. 13 I. In this case, preferably at least 60% or more preferably at least 80% of the total lines of adhesive are spaced at intervals of 0.001 to 10 cm.

(Evaluating the Capability of a Bodily Fluid-absorbing Article)

Evaluation of Liquid Return (Rewetting), Liquid Dispersion Distance

A sufficiently wide wooden board is placed on a laboratory table, and the four corners of a bodily fluid-absorbing article are stretched but not getting wrinkled and fixed with thumb tacks. A cylindrical pipe with a diameter of 60 mm and a weight of 53.5 g is placed on the center of the absorbent composite. 80 g of saline warmed to 37° C. is dripped through the pipe onto the center of the absorbent composite at a rate of 7 to 8 ml/second. After the saline is no longer visible on the upper surface of the top sheet, the pipe is removed. 5 minutes after the start of dripping, the distance of dispersion in the lengthwise direction is measured and determined to be the liquid dispersion distance.

1 minute after the dripping started, a 10 cm square piece that is cut out from Advantec No. 2 filter paper with a diameter of 150 mm are stacked on the dripping position so that the total weight become about 90 g, and a 3.5 kg load is immediately applied on the filter papers. 3 minutes after the load was applied, the load is removed, the filter papers are taken out from the article and weighed. The amount of the weight of the filter papers increased from the original weight is determined to be the first rewet amount.

9 minutes after the dripping started, the cylinder is replaced. 10 minutes after the dripping started, 80 g more of saline is dripped and the same procedures as the first dripping are repeated. The amount of the weight of the filter papers increased after these procedures is then determined to be the second rewet amount.

19 minutes after the first dripping started, the pipe is replaced, and 20 minutes after the first dripping started, 80 g more of saline is dripped and the same procedures are repeated. The amount of the weight of the filter papers increased after these procedures is then determined to be the third rewet amount.

The rewet amount is an indicator of rewetting or in other words of the feeling of the bodily fluid-absorbing article during use. If the rewet amount is large, the skin will become wet and the article will be unpleasant to wear. The rewet amount is preferably as small as possible to keep the surface of the article dry and make it comfortable to wear. The repeated rewet amounts indicate the feeling of the bodily fluid-absorbing article when it is worn continuously and absorbs bodily fluid repeatedly. The larger the second and third rewet amounts, the more comfortable the article will be when it is used continuously. The first rewet amount is preferably not more than 30 g, more preferably not more than 20 g, further more preferably not more than 10 g or still more preferably not more than 3 g. The second rewet amount is preferably not more than 40 g, more preferably not more than 30 g, further more preferably not more than 25 g or still more preferably not more than 20 g. The third rewet amount is preferably not more than 50 g, more preferably not more than 45 g, further more preferably not more than 40 g or still more preferably not more than 30 g.

The liquid dispersion distance means the distance of the portion that was used to absorb the liquid in the absorbent composite, and the longer the liquid dispersion distance, the higher the usage efficiency of the absorbent composite. If the usage efficiency of the absorbent composite is high, the necessary absorption capability can be attained with a small quantity of absorbent composite, allowing for conservation of resources. If the liquid dispersion distance is long, the absorbent layer after liquid absorption become thin, the likelihood of displacement of the absorbent composite decrease, and the absorbent composite become more comfortable to wear. The liquid dispersion distance is preferably at least 200 mm, more preferably at least 240 mm, further more preferably at least 270 mm or still more preferably at least 300 mm.

Evaluation of Lengthwise Dispersion, Distribution Area

A sufficiently wide wooden board is placed on a laboratory table, and the four corners of a bodily fluid-absorbing article are stretched but not getting wrinkled and fixed with thumb tacks. 50 cc of saline is continuously dripped at a rate of 1 ml/second onto the center of the absorbent composite. 2 minutes after completion of dripping, the length and width of the part into which the liquid dispersed are measured. Lengthwise dispersion is calculated according to Formula 11, and distribution area according to Formula 12.

Lengthwise dispersion=length of dispersion in the lengthwise direction (cm)/length of dispersion in the crosswise direction (cm)   (Formula 11)

Distribution area=length of dispersion in the lengthwise direction (cm)×length of dispersion in the crosswise direction (cm)   (Formula 12)

In a bodily fluid-absorbing article, leakage is normally more likely in the crosswise direction, in which the article generally is shorter. It is preferable that the lengthwise dispersion is high, as it makes liquid flow more readily in the lengthwise direction, and reduces leakage. A higher lengthwise dispersion is also desirable because it increases the usage efficiency of the absorbent composite. The lengthwise dispersion is preferably at least 1.4, more preferably at least 1.7, further more preferably at least 2.0 or still more preferably at least 2.5. In an absorbent composite with good dispersibility, the liquid may disperse as far as it reaches to the lateral edge. Leakage usually does not occur immediately after the liquid reaches to the edge, or is prevented by gathers or the like. However, it is preferable that the length of dispersion in the crosswise direction is shorter than the width of the article, as leakage may occur if a large quantity of liquid is further added.

The distribution area is an indicator of the liquid dispersibility of the article, and it is preferable to use the absorbent composite with higher distribution area in order to increase the usage efficiency of the absorbent composite. If the amount of liquid to be absorbed is kept constant, the absorbent composite with higher distribution area changes less in thickness after absorption and is more stable, because the amount of liquid to be absorbed per unit area decrease as the distribution area increase. If the absorbent composite change little in thickness, moreover, the article is more comfortable to wear without a feeling of pressure to the user. The distribution area is preferably at least 150 cm$^2$, more preferably at least 200 cm$^2$, further more preferably at least 250 cm$^2$ or still more preferably at least 300 cm$^2$.

Evaluating Leakage

In the present invention, leakage is measured as follows. The center of the absorbent composite part in the bodily fluid-absorbing article is marked with a cross mark with a size of about 1 cm. The absorbent composite is fixed with thumb tacks to a horizontal board over a line drawn parallel to the short direction from the center as shown in FIG. 14. When the absorbent composite has gathers or the like, the gathers are also fixed so that the edges of the absorbent composite can be seen from above. A plastic board is then inserted as shown in FIG. 15, and an article is fixed with tape so that they form an angle of 30° at the fixed point. In this case the absorbent composite is stretched but not getting wrinkled.

Saline dyed with edible red is dripped at a rate of 0.1 ml/second onto the point marked with a cross mark. The amount of liquid dripped at the point when the dispersed liquid begins to disperse outside of the edge of the absorbent composite is determined to be the leakage drip amount.

The leakage drip amount is preferably at least 100 ml, more preferably at least 120 ml, further more preferably at least 135 ml or still more preferably at least 150 ml. The leakage drip amount can be increased by increasing the thickness and weight of the absorbent composite, but the article itself is preferably thin and lightweight. In the present invention, therefore, the leakage coefficient as an indicator of leakage resistance per unit area is determined according to (Formula 13) below based on the leakage drip amount, the weight of the absorbent composite and the area of the absorbent composite.

Leakage coefficient=leakage drip amount (ml)/(the weight of the absorbent composite (g)/the area of the absorbent composite (cm$^2$)) (Formula 13)

The weight and area of the absorbent composite are determined by measuring the absorbent composite as a whole. In absorbent composites with the same weight and area, the greater the leakage coefficient, the greater the resistance to leakage. The leakage coefficient is preferably at least 1000, more preferably at least 2000, further more preferably at least 3000 or still more preferably at least 4000. It is preferable that the absorbent composite has both the leakage coefficient within this range and the leakage drip amount within the range described above.

EXAMPLES

Specific examples of the present invention are given below together with comparative examples, and the present invention is not limited to these examples.

Manufacturing 1

Acrylic acid of special grade reagent from Wako Pure Chemical was purified by distillation and used. 100 g of this acrylic acid was dissolved in 91.02 g of water. This aqueous solution was cooled in an ice bath and maintained at a liquid temperature of 30° C. or less, and 117.94 g of 25 wt % aqueous ammonia solution were gradually added to the solution with stirring to give a 40 wt % ammonium acrylate aqueous solution (neutralization rate 100%).

90 g of this 40 wt % ammonium acrylate aqueous solution and 0.0187 g of N,N'-methylenebisacrylamide were added to a 300 ml separable flask. The flask was immersed in a water bath so as to maintain a liquid temperature of 30° C. The water bath was deoxygenated by bubbling with nitrogen gas to substitute the reaction system with nitrogen. 0.43 g of 42 wt % aqueous glycerin solution was then added with a syringe and thoroughly stirred, and 0.0917 g of 30 wt % aqueous hydrogen peroxide solution and 0.0415 g of Rongalite, each dissolved in 1 g of water, were added to initiate polymerization. 5 minutes after the start of the reaction, the internal temperature had risen to 100° C. from the initial temperature of 30° C. This was then heated for 3 hours in a water bath so as to maintain an internal temperature at 70° C. The gel was then taken out from the separable flask, coarsely grounded and dried for 4 hours at 100° C. in an inert oven. After completion of drying, it was pulverized with a homogenizer and classified by sieving into sizes of under 106 µm, 106 to 212 µm, 212 to 300 µm, 300 to 425 µm, 425 to 500 µm, 500 to 600 µm, 600 to 710 µm, 710 to 850 µm, 850 to 1200 µm, 1200 to 1400 µm, 1400 to 1700 µm, 1700 to 2500 µm, 2500 to 3000 µm and over 3000 µm. These were used as water-absorbent resin particles 1. The surface strength of these resin particles was 0.5 N. The overall ammonium salt concentration was 96%, the salt concentration of the surface was 90% and the salt concentration at the center was 97%.

Manufacturing 2

The water-absorbent resin particles 1 manufactured in Manufacturing 1 were heat-treated for 10 minutes in an inert oven at 180° C., and used as water-absorbent resin particles 2. The surface strength was 2.7 N. The overall ammonium salt concentration was 70%, the salt concentration of surface was 30% and the salt concentration at the center was 95%.

Manufacturing Example 3

81.73 g of acrylic acid of special grade reagent from Wako Pure Chemical, 185.71 g of water and 31.78 g of sodium hydroxide were slowly added to a 300 ml flask while the flask was being cooled so that the liquid temperature did not exceed 30° C. (salt concentration 70%). 90 g of this monomer solution and 0.0561 g of N,N'-methylenebisacrylamide were added to a 300 ml separable flask. The flask was immersed in a water bath so as to maintain a liquid temperature at 30° C. The water bath was deoxygenated by bubbling with nitrogen gas to substitute the reaction system with nitrogen. 0.0826 g of 30 wt % of and 0.0518 g of Rongalite, each dissolved in 1 g of water, were added to initiate polymerization. After 10 minutes, the internal temperature had risen to 70° C. from the initial temperature of 30° C. 5 minutes after the internal temperature has reached to the maximum temperature, the solution was heated for 3 hours in a water bath so as to maintain an internal temperature at 75° C. After a lapse of predetermined time, the gel was taken out from the separable flask, coarsely grounded and dried for 4 hours at 100° C. in an inert oven. After completion of drying, it was pulverized with a homogenizer and classified by sieving into sizes of under 106 µm, 106 to 212 µm, 212 to 300 µm, 300 to 425 µm, 425 to 500 µm, 500 to 600 µm, 600 to 710 µm, 710 to 850 µm, 850 to 1200 µm, 1200 to 1400 µm, 1400 to 1700 µm, 1700 to 2500 µm, 2500 to 3000 µm and over 3000 µm. These were used as water-absorbent resin particles 3. The surface strength of the resin was 0.9 N.

Manufacturing 4

A mixture of 0.6 g of isopropyl alcohol, 0.02 g of glycerin and 0.06 g of water was prepared, and dispersed uniformly over 2 g of the water-absorbent resin particles 2 manufactured in Manufacturing 3. These were heated for 10 minutes at 180° C. in an inert oven, and used as water-absorbent resin 4. The surface strength of the resin was 5.9 N.

Manufacturing 5

81.73 g of acrylic acid of reagent special grade from Wako Pure Chemical, 185.71 g of water and 21.8 g of sodium hydroxide were slowly added to a 300 ml flask while cooling the flask with ice so as to keep the liquid temperature not to exceed 30° C. (salt concentration 48%). 90 g of this monomer solution and 0.0561 g of N,N'-methylenebisacrylamide were added to a 300 ml separable flask. The flask was immersed in a water bath so as to maintain a liquid temperature at 30° C. The water bath was deoxygenated by bubbling with nitrogen gas to substitute the reaction system with nitrogen. 0.0826 g of 30 wt % aqueous hydrogen peroxide solution and 0.0518 g of Rongalite, each dissolved in 1 g of water, were added to initiate polymerization. After 10 minutes, the internal temperature had risen to 70° C. from the initial temperature of 30° C. 5 minutes after the internal temperature has reached to the maximum temperature, the solution was heated for 3 hours in a water bath so as to maintain an internal temperature at 75° C. After a lapse of predetermined time, the gel was taken out from the separable flask, coarsely grounded and dried for 4 hours at 100° C. in an inert oven. After completion of drying, it was pulverized with a homogenizer and classified by sieving into sizes of under 106 µm, 106 to 212 µm, 212 to 300 µm, 212 to 300 µm, 300 to 425 µm, 425 to 500 µm, 500 to 600 µm, 600 to 710 µm, 710 to 850 µm, 850 to 1200 µm, 1200 to 1400 µm, 1400 to 1700 µm, 1700 to 2500 µm, 2500 to 3000 µm and over 3000 µm. These were used as water-absorbent resin particles 5. The surface strength of the resin was 1.1 N.

Manufacturing 6

A mixture of 0.6 g of isopropyl alcohol, 0.02 g of glycerin and 0.06 g of water was prepared, and dispersed uniformly over 2 g of the water-absorbent resin particles 5 manufactured in Manufacturing 5. These were heated for 10 minutes at 180° C. in an inert oven, and used as water-absorbent resin particles 6. the surface strength of the resin was 6 N.

Manufacturing 7

Acrylic acid of reagent special grade from Wako Pure Chemical was purified by distillation. 753 g of the purified acrylic acid was cooled in an ice bath and maintained at a liquid temperature at 30° C. or less, and 625 g of 25 wt % aqueous ammonia solution of reagent special grade from Wako Pure Chemical was added gradually, while stirring the solution to give a 66 wt % ammonium acrylate aqueous solution (neutralization rate 100%). 0.0395 g of N,N'-methylenebisacrylamide dissolved in 1 g of water was added and dissolved by stirring the solution, and the mixture was deoxygenated by bubbling with nitrogen gas.

4.3 L of cyclohexane and 7.8785 g of sorbitan monostearate as a surfactant were added to a 12 L autoclave with a nitrogen atmosphere already in the system, and dissolved by stirring at room temperature, and the reaction system was deoxygenated under reduced pressure of 65 kPa. The reaction system was heated, still under reduced pressure, to an internal temperature of 60° C. An aqueous solution of 0.7186 g of ammonium persulfate dissolved in 50 g of water was added to the aforementioned ammonium acrylate aqueous solution. After the internal temperature of the reaction system had reached 60° C., the prepared ammonium acrylate aqueous solution was added to the system, and suspended by stirring at 120 rpm in a flow of nitrogen. Polymerization was initiated in the reaction system maintained at 65 kPa, and at internal temperature of 60° C., and the reaction system was stirred at a stirring speed of 120 rpm for 2 hours to give an emulsion containing a wet gel. The inside of the reaction system was returned to normal pressure with nitrogen, sealed, and heated at an internal temperature of 80° C., the stirring speed was set to 400 rpm, and a mixed solution of 108.8 g of ethanol from Wako Pure Chemical and 8.35 g of glycerin was added over 15 minutes. The system was pressurized with nitrogen, heated to an internal temperature of 110° C. and maintained with stirring for 30 minutes. The pressure was then lowered to normal pressure, and the resulting wet gel was washed three times with 2 L of cyclohexane at 40° C.

The resulting wet gel was collected by filtration, dried in a 70° C. full vacuum and collected. The gel was dried for 6 hours in an inert oven at 70° C. After completion of drying, it was grounded coarsely with a homogenizer and classified by sieving into sizes of under 106 µm, 106 to 212 µm, 212 to 300 µm, 300 to 425 µm, 425 to 500 µm, 500 to 600 µm, 600 to 710 µm, 710 to 850 µm, 850 to 1400 µm, 850 to 1200 µm, 1200 to 1400 µm, 1400 to 1700 µm, 1700 to 2500 µm, 2500 to 3000 µm and over 3000 µm. These were used as water-absorbent resin particles 7. The absorption capacity of these resin particles was 70×. The surface strength of these resin particles was 0.4 N. The overall ammonium salt concentration was 95%, the surface salt concentration was 88% and the center salt concentration was 97%.

The water-absorbent resin particles 7 manufactured in Manufacturing 7 were heat treated for 10 minutes in an inert oven at 180° C. The conditions for this operation are the same as the heat treatment conditions for forming a composite with the base material in the following examples. As a result, the surface salt strength of the water-absorbent resin was 2.5 N, with an overall ammonium salt concentration of 70%, and the salt concentration of the surface of 32% and a the salt concentration at the center of 94%.

Manufacturing 8

The same operations were carried out as in Manufacturing 7 except that the stirring speed during polymerization was changed from 120 rpm to 400 rpm. The resulting particles were water-absorbent resin particles 8. The absorption capacity of these resin particles was 80×. The surface strength of the resin particles was 0.4 N. The overall ammonium salt concentration was 95%, the salt concentration of the surface was 87% and the salt concentration at the center was 97%.

The water-absorbent resin particles 8 manufactured in Manufacturing 8 were heat-treated for 10 minutes in an inert oven at 180° C. The conditions for this operation are the same as the heat treatment conditions for forming a composite with the base material in the following examples. As a result, the surface salt strength of the water-absorbent resin was 2.2 N, with an overall ammonium salt concentration of 68%, the salt concentration of the surface of 33% and the salt concentration at the center of 93%.

Manufacturing 9

Acrylic acid of reagent special grade from Wako Pure Chemical was prepared. 2557.8 g of the reagent acrylic acid was dissolved in 2087.3 g of water. The aqueous solution was cooled in an ice bath, and 3507.0 g of 40.5 wt % aqueous NaOH solution was added gradually with stirring while keeping the liquid temperature at 30° C. or less to give a 40 wt % sodium acrylate aqueous solution.

1733.0 g of the sodium acrylate aqueous solution obtained above was dissolved in 341.5 g of water. 227.7 g of acrylic acid was added to this sodium acrylate aqueous solution to give 2302.2 g of a 40 wt % sodium acrylate/acrylic acid=70/30 aqueous solution. 2.5 g of N,N'-methylenebisacrylamide was added and dissolved as a crosslinking agent, and the mixture was deoxygenated by bubbling with nitrogen gas.

4.3 L of cyclohexane and 7.8785 g of sorbitan monostearate as a surfactant were added to a 12 L autoclave substituted with nitrogen in advance, and dissolved by stirring the solution at room temperature, and the reaction system was deoxygenated under reduced pressure of 65 kPa. The reaction system was heated, still under reduced pressure, to an internal temperature of 60° C. An aqueous solution of 0.7186 g of ammonium persulfate dissolved in 50 g of water was added to the aforementioned sodium acrylate aqueous solution. After the internal temperature of the reaction system had reached 60° C., the prepared sodium acrylate aqueous solution was added to the system, and suspended by stirring at 400 rpm in a flow of nitrogen. Polymerization was initiated in the reaction system maintained at 65 kPa, internal temperature 60° C., and the reaction system was stirred at a stirring speed of 400 rpm for 2 hours to give an emulsion containing a wet gel. The inside of the reaction system was returned to normal pressure with nitrogen, sealed, and heated at an internal temperature of 80° C., the stirring speed was set to 400 rpm, and a mixed solution of 108.8 g of ethanol from Wako Pure Chemical and 4.2 g of glycerin was added over 15 minutes. The system was pressurized with nitrogen, heated to an internal temperature of 110° C. and maintained with stirring for 30 minutes. The pressure was then lowered to normal pressure, and the resulting wet gel was washed three times with 2 L of cyclohexane at 40° C.

The resulting wet gel was collected by filtration, dried in a 70° C. full vacuum and collected. After completion of drying, it was grounded with a homogenizer and classified by sieving into sizes of under 106 μm, 106 to 212 μm, 212 to 300 μm, 300 to 425 μm, 425 to 500 μm, 500 to 600 μm, 600 to 710 μm, 710 to 850 μm, 850 to 1200 μm, 1200 to 1400 μm, 1400 to 1700 μm, 1700 to 2500 μm, 2500 to 3000 μm and over 3000 μm. These were used as water-absorbent resin particles 9. The absorption capacity of these resin particles was 55×. The surface strength of these resin particles was 1.2 N.

Manufacturing 10

Acrylic acid of reagent special grade from Wako Pure Chemical was purified by distillation. 753 g of the purified acrylic acid was cooled in an ice bath and maintained at a liquid temperature of 30° C. or less, and 625 g of 25 wt % aqueous ammonia solution of reagent special grade from Wako Pure Chemical was added gradually with stirring to give a 66 wt % ammonium acrylate aqueous solution (neutralization rate 100%). This was then deoxygenated by bubbling with nitrogen gas.

4.3 L of cyclohexane and 7.53 g of sorbitan monolaurate as a surfactant were added to a 12 L autoclave substituted with a nitrogen atmosphere in advance, and dissolved by stirring at room temperature, and the reaction system was deoxygenated under reduced pressure of 30 kPa. This was heated, still under reduced pressure, to an internal temperature of 40° C. An aqueous solution of 0.7699 g of ammonium persulfate dissolved in 50 g of water was added to the aforementioned ammonium acrylate aqueous solution. After the internal temperature of the reaction system had reached 40° C., the prepared ammonium acrylate aqueous solution was added to the system, and suspended by stirring at 400 rpm in a flow of nitrogen. Polymerization was initiated in the reaction system maintained at 30 kPa, internal temperature 40° C., and the reaction system was stirred at a stirring speed of 400 rpm for 2 hours to give an emulsion containing a wet gel. The pressure was then lowered to normal pressure, and the resulting wet gel was washed three times with 2 L of cyclohexane at 40° C.

The resulting wet gel was collected by filtration, dried in a 70° C. full vacuum and collected. After drying, this was grounded with a homogenizer and classified by sieving into sizes of under 106 μm, 106 to 212 μm, 212 to 300 μm, 300 to 425 μm, 425 to 500 μm, 500 to 600 μm, 600 to 710 μm, 710 to 850 μm, 850 to 1200 μm, 1200 to 1400 μm, 1400 to 1700 μm, 1700 to 2500 μm, 2500 to 3000 μm and over 3000 μm. These were used as water-absorbent resin particles 10. The absorption capacity of these resin particles was 80×. The surface strength of these resin particles was 0.6 N. The overall ammonium salt concentration was 97%, the salt concentration of the surface was 91% and the salt concentration at the center was 98%.

The water-absorbent resin particles 10 manufactured in Manufacturing 10 were heat treated for 10 minutes in an inert oven at 180° C. The conditions for this operation are the same as the heat treatment conditions for forming a composite with the base material in the following examples. As a result, the surface salt strength of the water-absorbent resin was 2.8 N, with an overall ammonium salt concentration of 70%, the salt concentration of the surface of 29% and the salt concentration at the center of 95%.

Manufacturing 11

Acrylic acid of reagent special grade from Wako Pure Chemical was prepared. 2557.8 g of the reagent acrylic acid was dissolved in 2087.3 g of water. This aqueous solution was cooled in an ice bath, and 3507.0 g of 40.5 wt % aqueous NaOH solution was added gradually with stirring while keeping the liquid temperature at 30° C. or less to give a 40 wt % sodium acrylate aqueous solution.

1733.0 g of the sodium acrylate aqueous solution obtained above was dissolved in 341.5 g of water. 227.7 g of acrylic acid was added to this sodium acrylate aqueous solution to give 2302.2 g of a 40 wt % sodium acrylate/acrylic acid=70/30 aqueous solution. 2.5 g of N,N'-methylenebisacrylamide was added and dissolved as a crosslinking agent, and the mixture was deoxygenated by bubbling with nitrogen gas.

4.3 L of cyclohexane and 7.8785 g of sorbitan monostearate as a surfactant were added to a 12 L autoclave substituted with a nitrogen atmosphere in advance, and dissolved by stirring at room temperature, and the reaction system was deoxygenated under reduced pressure of 65 kPa. This was heated, still under reduced pressure, to an internal temperature of 60° C. An aqueous solution of 0.7186 g of ammonium persulfate dissolved in 50 g of water was added to the aforementioned sodium acrylate aqueous solution. After the internal temperature of the reaction system had reached 60° C., the prepared sodium acrylate aqueous solution was added to the system, and suspended by stirring at 400 rpm in a flow of nitrogen. Polymerization was initiated with the reaction system maintained at 65 kPa, internal temperature 60° C., and the reaction system was stirred at a stirring speed of 400 rpm for 2 hours to give an emulsion containing a wet gel. The inside of the reaction system was returned to normal pressure with nitrogen, sealed, and heated at an internal temperature of 80° C., the stirring speed was set to 400 rpm, and 108.8 g of ethanol from Wako Pure Chemical was added over 15 minutes. The system was pressurized with nitrogen, heated to an internal temperature of 110° C. and maintained with stirring for 30 minutes. The pressure was then lowered to normal pressure, and the resulting wet gel was washed with 2 L of cyclohexane three times at 40° C.

The resulting wet gel was collected by filtration, dried in a 70° C. full vacuum and collected. After completion of drying, it was grounded with a homogenizer and classified by sieving into sizes of under 106 μm, 106 to 212 μm, 212 to 300 μm, 300 to 425 μm, 425 to 500 μm, 500 to 600 μm, 600 to 710 μm, 710 to 850 μm, 850 to 1400 μm, 850 to 1200 μm, 1200 to 1400 μm, 1400 to 1700 μm, 1700 to 2500 μm, 2500 to 3000 μm and over 3000 μm. These were used as water-absorbent resin particles 11. The absorption capacity of these resin particles was 57×. The surface strength of these resin particles was 1.1 N.

The material properties of the water-absorbent resin particles 1 to 11 manufactured in Manufacturing 1 to 11 are shown in Table 1.

TABLE 1

| | Average absorption capacity (g/g) | Absorption capacity under pressure (g/g) | Residual monomers (ppm) |
|---|---|---|---|
| Water-absorbent resin particles 1 | 76 | 28 | 170 |
| Water-absorbent resin particles 2 | 83 | 35 | <20 |
| Water-absorbent resin particles 3 | 61 | 26 | 200 |
| Water-absorbent resin particles 4 | 54 | 21.6 | 160 |
| Water-absorbent resin particles 5 | 53 | 23 | 190 |
| Water-absorbent resin particles 6 | 43 | 12.3 | 160 |
| Water-absorbent resin particles 7 | 70 | | <20 |
| Water-absorbent resin particles 8 | 80 | | <20 |
| Water-absorbent resin particles 9 | 55 | | <20 |
| Water-absorbent resin particles 10 | 80 | | <20 |
| Water-absorbent resin particles 11 | 57 | | <20 |
| Water-absorbent resin particles 12 | 76 | 28 | 170 |
| Water-absorbent resin particles 13 | 76 | 28 | 170 |

Example 1

A portion of a circle with a diameter of 59.5 mm was cut out from Bemliese® from Asahi Kasei Fibers Corp. (material properties shown in Table 2), and the weight of the portion was 0.0796 g. Bemliese® is a nonwoven fabric made from 100% cellulose continuous-filament. Because it is a cellulose nonwoven fabric, it has excellent absorption properties. Because it is made from the continuous filaments, it is sufficiently strong when containing water and has excellent liquid dispersibility.

Of the water-absorbent resin particles 1 synthesized in Manufacturing 1, 0.164 g of particles with a particle size of 850 to 1200 μm were arranged on Teflon sheet with a diameter of 59.5 mm so that the particles were not closely packed. This was called Teflon (1). Another Teflon sheet was prepared in the same way and called Teflon (2). The Bemliese® was placed on Teflon (1), and sprayed with 3 ml of water with an atomizer. Teflon (1) was placed upside-down on Teflon (2) with the Bemliese® side of Teflon (1) on top of the particle side of Teflon (2). This was pressed down lightly by hand, left for 1 minute, and heated for 10 minutes at 180° C. in an inert oven. The weight as measured immediately after heating was 0.4061 g. The weight ratio of the water-absorbent resin in the composite is calculated as 80.4%. All of the water-absorbent resin particles were strongly adhered to Bemliese®, and none of the water-absorbent resin became detached when rubbed by hand. It was observed with a scanning electron microscope (JEOL JSM-5300) that all the particles adhere to Bemliese® with fibers incorporated inside the water-absorbent resin.

FIG. 16 is an electron microscope image of the configuration of adhesion (150× enlargement), which was taken from the side at an angle, rather than from above the particles, so that the adhesion configuration appears in the image. This composite was called Example 1.

In FIG. 16, the part inside the circle is an adhering bond between the water-absorbent resin and fibers. The water-absorbent resin particles appear to the upper right of the black part and the fiber part of the base material to the lower left, and the fibers appear black, showing that they are bonded inside the water-absorbent resin particles.

Example 2

An experiment was carried out in the same way as in Example 1 except that resin particles 7 with a particle size of 850 to 1200 μm manufactured in Manufacturing 7 were used. The evaluation results are shown in Table 3.

Example 3

An experiment was carried out in the same way as in Example 1 except that resin particles 8 with a particle size of 850 to 1200 μm manufactured in Manufacturing 8 were used. The evaluation results are shown in Table 3.

Example 4

An experiment was carried out in the same way as in Example 1 except that resin particles 9 with a particle size of 850 to 1200 μm manufactured in Manufacturing 9 were used. The evaluation results are shown in Table 3.

Example 5

An experiment was carried out in the same way as in Example 1 except that resin particles 10 with a particle size of 850 to 1200 μm manufactured in Manufacturing 10 were used. The evaluation results are shown in Table 3.

Example 6

An experiment was carried out in the same way as in Example 1 except that resin particles 11 with a particle size of 850 to 1200 μm manufactured in Manufacturing 11 were used. The evaluation results are shown in Table 3.

Comparative Example 1

81.73 g of reagent acrylic acid (Wako Pure Chemical, reagent special grade), 185.71 g of water and 31.78 g of sodium hydroxide were gradually added in a 300 ml flask with ice cooling so that the liquid temperature did not exceed 30° C. (salt concentration 70%). 90 g of this monomer solution was poured into an atomizer in a nitrogen box, and 0.0561 g of N,N'-methylenebisacrylamide was added. The aqueous solution was deoxygenated by bubbling with nitrogen gas. 1 ml of a solution of 0.022 g of iron chloride (III) hexahydrate dissolved in 100 g of water, 1 ml of 30 wt % hydrogen peroxide solution, and a solution of 0.12 g of L-ascorbic acid dissolved in 1 ml of water were rapidly added and stirred, and the mixture was sprayed over Spun Bond EltasCrimp® PC8020 from Asahi Kasei Fibers Corp. Whole set of this including nonwoven fabric was heated to 60° C. with a hot plate, and polymerized for 1 hour, then the temperature was raised to 120° C. and maintained for 30 minutes to complete polymerization. It was vacuum dried at 100° C., the residual monomer level was measured as 1000 ppm or more.

Comparative Example 2

A composite was prepared in the same way as Example 1 using the water-absorbent resin particles 2 prepared in Manufacturing 2. Particles with a particle size of 850 to 1200 μm were used. Because the ammonium salt concentration near the surface was as low as 30%, only about 35% of the resin particles adhered. The area occupancy rate was measured immediately after heating before the resin had detached. Because the ratio of the particles adhering is low, it was difficult to obtain stable performance. The evaluation results are shown in Table 3.

Comparative Example 3

A composite was prepared in the same way as Example 1 using the water-absorbent resin particles 6 obtained in Manufacturing 6. Particles with a particle size of 850 to 1200 μm were used. The surface strength was as high as 6 N, and only about 25% of the resin adhered. The area occupancy rate was measured immediately after heating before the resin detached. The evaluation results are shown in Table 3.

Comparative Example 4

A composite was prepared in the same way as Example 1 except that no water was added. The particles did not adhere.

Example 7

A composite was prepared in the same way as Example 1 except that 15 g of water was used. Because water remained after 10 minutes heating, it was heated for a further 10 minutes.

Example 8

A composite was prepared in the same way as Example 1 except that the drying conditions were 60° C., 5 hours.

Example 9

A composite was prepared in the same way as Example 1 except that the drying temperature was 370° C. Because it would burn if it was over heated, the dry conditions was checked every few seconds, and heating was terminated at the time when the drying was completed.

TABLE 2

| | Density (g/m$^2$) | Absorption capacity (g/g) | Contact angle (degree) | Absorption speed (mg/sec) | Thickness (mm) | Tensile breaking strength (N/20 mm) | Elongation (cm) | Tensile breaking strength after absorbing saline (N/cm$^2$) |
|---|---|---|---|---|---|---|---|---|
| Bemliese length | 28 | 14 | 0 | 0.74 | 0.45 | 7.2 | 4 | 4.9 |
| Bemliese width | | | | 0.58 | | 1.5 | 12.3 | 1 |
| Nylon Spunbond length | 20 | 7.8 | 111 | 0.27 | 0.15 | 9 | 28.2 | 6.8 |
| Nylon Spunbond width | | | | 0.27 | | 5.8 | 54 | 4 |
| PET Spunbond length | 25 | 6.7 | 124 | 0.16 | 0.12 | 35.3 | 21 | 28.4 |
| PET Spunbond width | | | | 0.15 | | 12.7 | 20 | 12.7 |
| Kinocloth | 40 | 33 | 0 | 0.34 | 1 | 2.9 | 19.6 | 0.68 |
| PP Spunbond | 20 | 5.6 | 135 | | 0.19 | | | |
| Toilet paper | | | | | | | | <0.1 |
| Saran wrap | | 3 | | | | | | |
| Rayon Spunbond length | 25 | 12 | 0 | 0.45 | 0.31 | 7.8 | 3.7 | 5.2 |
| Rayon Spunbond width | | | | 0.35 | | 2 | 8.9 | 1.3 |

The physical properties of the absorbent composites of Examples 1 to 9 and Comparative Examples 2 and 3 are shown in Table 3.

facturing 1 were used and the weight ratio of resin in the absorbent composite was 72.8%. The evaluation results are shown in Table 4.

TABLE 3

| | Absorbent composite | | | | | |
|---|---|---|---|---|---|---|
| | Water-absorbent resin Particles No. | Weight ratio (%) | Adhesion rate (%) | Total surface area coefficient | Area occupancy rate of large particles (%) | Absorption capacity (g/g) | Absorption capacity after 1 minute (g/g) |
| Example 1 | 1 | 80 | 100 | 0.16 | 12 | 55.1 | 7 |
| Example 2 | 7 | 80 | 100 | 0.19 | 13 | 51.3 | 8 |
| Example 3 | 8 | 80 | 100 | 0.18 | 14 | 55.2 | 10 |
| Example 4 | 9 | 80 | 100 | 0.15 | 14 | 41 | 8 |
| Example 5 | 10 | 80 | 100 | 0.2 | 9 | 58.6 | 4 |
| Example 6 | 11 | 80 | 100 | 0.17 | 14 | 42.4 | 5 |
| Example 7 | 1 | 80 | 100 | 0.16 | 12 | 54 | 7 |
| Example 8 | 1 | 80 | 100 | 0.19 | 13 | 55 | 7 |
| Example 9 | 1 | 80 | 100 | 0.16 | 12 | 52 | 7 |
| Comparative Example 2 | 2 | 80 | 35 | 0.16 | 12 | 51 | 4 |
| Comparative Example 3 | 6 | 80 | 25 | 0.19 | 13 | 30 | 2 |
| Comparative Example 4 | 1 | 80 | 0 | 0.16 | 12 | 50 | 4 |

Example 10

An experiment was carried out in the same way as in Example 1 except that the water-absorbent resin particles 1 with a particle size of 500 to 600 μm manufactured in Manufacturing 1 were used and the weight ratio of resin in the absorbent composite was 67.6%. The evaluation results are shown in Table 4.

Example 11

An experiment was carried out in the same way as in Example 1 except that the water-absorbent resin particles 1 with a particle size of 710 to 850 μm manufactured in Manufacturing 1 were used and the weight ratio of resin in the absorbent composite was 72.6%. The evaluation results are shown in Table 4.

Example 12

An experiment was carried out in the same way as in Example 1 except that rayon spun lace was used as the base material (physical properties of rayon span lace shown in Table 2), and the weight ratio of resin in the absorbent composite was 81.5%. The evaluation results are shown in Table 4.

Example 13

An experiment was carried out in the same way as in Example 1 except that the water-absorbent resin particles 1 with a particle size of 1700 to 2500 μm manufactured in Manufacturing 1 were used and the weight ratio of resin in the absorbent composite was 89.2%. The evaluation results are shown in Table 4.

Example 14

An experiment was carried out in the same way as in Example 1 except that the water-absorbent resin particles 1 with a particle size of 710 to 850 μm manufactured in Manu-

Example 15

An experiment was carried out in the same way as in Example 1 except that the weight ratio of resin in the absorbent composite was 66.6%. The evaluation results are shown in Table 4.

Example 16

An experiment was carried out in the same way as in Example 8 except that the weight ratio of resin in the absorbent composite was 71.6%. The evaluation results are shown in Table 4.

Example 17

An experiment was carried out in the same way as in Example 1 except that the water-absorbent resin particles 7 with a particle size of 850 to 1200 manufactured in Manufacturing 7 were used and the weight ratio of resin in the absorbent composite was 80.0%, and rayon spun lace was used as the base material. The evaluation results are shown in Table 4.

Comparative Example 5

An experiment was carried out in the same way as in Example 1 except that the water-absorbent resin particles 1 with a particle size of 300 to 425 μm manufactured in Manufacturing 1 were used and the weight ratio of resin in the absorbent composite was 64%. The evaluation results are shown in Table 4.

The physical properties of the absorbent composites of Examples 10 to 17 and Comparative Example 5 are shown in Table 4.

TABLE 4

| | Water-absorbent resin | | | Absorbent composite | | | | | |
|---|---|---|---|---|---|---|---|---|---|
| | Particles No. | Av. size (μm) | Base material | Weight ratio (%) | Adhesion rate (%) | Total surface area coefficient | Area occupancy rate of large particles (%) | Absorption capacity (g/g) | Absorption capacity Under pressure (g/g) |
| Ex. 10 | 1 | 550 | Bemliese | 67.6 | 100 | 0.15 | 17 | 50 | |
| Ex. 11 | 1 | 780 | Bemliese | 72.6 | 100 | 0.13 | 16 | 47.3 | |
| Ex. 12 | 1 | 1025 | Spunlace | 81.5 | 100 | 0.15 | 12 | 56.5 | |
| Ex. 13 | 1 | 2100 | Bemliese | 89.2 | 100 | 0.15 | 14 | 51.3 | |
| Ex. 14 | 1 | 780 | Bemliese | 72.8 | 100 | 0.13 | 18 | | 15.6 |
| Ex. 15 | 1 | 1025 | Bemliese | 66.6 | 100 | 0.08 | 16 | | 18.7 |
| Ex. 16 | 1 | 2100 | Bemliese | 71.6 | 100 | 0.04 | 19 | | 20.5 |
| Ex. 17 | 1 | 1025 | Spunlace | 80 | 100 | 0.17 | 14 | 50 | |
| Comp. Ex. 5 | 1 | 362.5 | Bemliese | 64 | 100 | 0.19 | 30 | 38 | |

Example 18

A composite of Example 18 was prepared in the same way as Example 1 except that the particles of a mixture of 50 wt % of the water-absorbent particles 1 with a particle size of 850 to 1200 μm manufactured in Manufacturing 1 and 50 wt % of the water-absorbent particles 1 with a particle size of 100 to 300 μm manufactured in Manufacturing 1 was used. 98% of the particles adhered, with fibers incorporated into the water-absorbent resin in all adhesion.

Example 19

A composite of Example 19 was prepared in the same way as Example 1 except that the particles of a mixture of 30% of the water-absorbent particles 1 with a particle size of 850 to 1200 μm manufactured in Manufacturing 1 and 70% of the water-absorbent particles 1 with a particle size of 100 to 300 μm sized particles manufactured in Manufacturing 1 was used. 98% of the particles adhered, with fibers incorporated into the water-absorbent resin in all adhesion.

Example 20

A composite of Example 20 was prepared in the same way as Example 1 except that the particles of a mixture of 30% of the water-absorbent particles 1 with a particle size of 850 to 1200 μm manufactured in Manufacturing 1, 20% of the water-absorbent particles 1 with a particle size of 3000 μm or larger manufactured in Manufacturing 1 and 50% of the water-absorbent particles 1 with a particle size of 100 to 300 μm manufactured in Manufacturing 1 was used. 98% of the particles adhered, with fibers incorporated into the water-absorbent resin in all cases.

Example 21

A composite of Example 21 was prepared in the same way as Example 1 except that the water-absorbent particles 3 with a particle size of 850 to 1200 μm manufactured in Manufacturing 3 were used. All of the water-absorbent resin adhered strongly to Bemliese®, with fibers incorporated into the water-absorbent resin. Compared with the water-absorbent resin particles 1 of Manufacturing 1, the absorption amount absorbed by the composite was slightly lower because absorption amount absorbed by the resin particles was less.

Example 22

A composite of Example 22 was prepared in the same way as Example 1 except that the water-absorbent resin particles 4 with a particle size of 850 to 1200 μm manufactured in Manufacturing 4 were used. Adhesiveness was somewhat weaker because of the higher surface strength, and 67% of the particles adhered.

Example 23

A composite of Example 23 was prepared in the same way as Example 1 except that Asahi Kasei Fibers nylon Spun Bond® (physical properties shown in Table 2) was used instead of Bemliese®. The particles with a particle size of 850 to 1200 μm were used. 92% of the particles adhered.

Example 24

A composite of Example 24 was prepared in the same way as Example 1 except that Oji Kinocloth KS-40® manufactured by Oji Kinocloth, (physical properties shown in Table 2) was used instead of Bemliese®. Oji Kinocloth is a dry pulp nonwoven fabric. The particles with a particle size of 850 to 1200 μm were used. All of the water-absorbent resin particles adhered with fibers incorporated into the water-absorbent resin. Because the strength of pulp is low, the particles easily detached together with the pulp fibers with tweezers.

Example 25

A composite of Example 25 was prepared in the same way as Example 1 except that Asahi Kasei Fibers PET Spunbond® (physical properties shown in Table 2) was used instead of Bemliese®. The particles with a size of 850 to 1200 μm were used. The adhesive force was weak and only 62% of the particles adhered.

Example 26

A composite of Example 26 was prepared in the same way as Example 1 except that Asahi Kasei Fibers polypropylene Spunbond Eltas® P03020 (physical properties shown in Table 2) was used instead of Bemliese®. The particles with a particle size of 850 to 1200 μm were used. The adhesive force was weak, and only 51% of the particles adhered.

Example 27

A composite of Example 27 was prepared in the same way as Example 1 except that Toyo Co. toilet paper "Piason" singles were used instead of Bemliese®. The particles with a particle size of 850 to 1200 μm were used. Because the strength was low when it was wet, it readily tore while being handled.

Example 27-2

A composite of Example 27-2 was prepared in the same way as Example 1 except that the ratio of resin was 94%, the water-absorbent resin particles 1 with a particle size of 850 to 1200 μm manufactured in Manufacturing 1 were used. 95% of the water-absorbent resin particles adhered. The absorbent resin particles were densely packed. Some particles detached after absorption, because some of the particles overlapped with each other.

Reference Example 1

The liquid permeability of "Saran Wrap" from Asahi Kasei Life & Living Co., Ltd. was measured. The water could not pass through the wrap. It is not preferable to use a completely water-impermeable film for sanitary material, because it can be used only for one side.

Comparative Example 7

A mixture of pulp and water-absorbent resin was taken out from absorber of a Pampers Cotton Care® M size from P & G Co., Ltd., and used as Comparative Example 7. The water-absorbent resin did not adhere to the pulp, and the pulp was cottony and did not maintain its shape. The weight ratio of the resin could not be measured by the method of the present invention. Because there was no base material, the area occupancy rate could not be measured.

Comparative Example 8

A top sheet and back sheet were separated from a Rifure Anshin Pad®, 150 cc size from Livedo Corporation, and the absorber alone was taken out. A circular piece of with a diameter of 59.5 mm was cut out from the center of this. The water-absorbent resin adhered to the base material with an adhesive and they did not directly adhere to the base material. This was given as Comparative Example 8.

Comparative Example 9

Acrylic acid of special grade reagent from Wako Pure Chemical was used after being purified by distillation. 10 g of the reagent acrylic acid was dissolved in 91.02 g of water. This aqueous solution was chilled in an ice bath and maintained at a liquid temperature of 30° C. or less and 117.94 g of 25 wt % aqueous ammonia solution was added gradually with stirring to give a 40 wt % ammonium acrylate aqueous solution.

A simple nitrogen box was prepared, and all subsequent operations were carried out in a nitrogen-substituted nitrogen box. 90 g of the 40 wt % ammonium acrylate aqueous solution and 0.0187 g of N,N'-methylenebisacrylamide were added in a 300 ml flask. The aqueous solution was deoxygenated by bubbling with nitrogen gas. The internal temperature at this time was 20° C. 0.43 g of 42 wt % glycerin aqueous solution was then added with a syringe and thoroughly stirred, and 0.0917 g of 30 wt % hydrogen peroxide aqueous solution and 0.0415 g of Rongalite, each dissolved in 1 g of water, were added to initiate polymerization. After the internal temperature began to rise from 20° C., 50 g of the reaction liquid was poured over 3 g of Bemliese® prepared in a tray. This was left for 3 hours, taken out from the nitrogen box, and then dried for 4 hours at 100° C. in an inert oven. This was given as Comparative Example 9. This absorbent composite was hard and difficult to cut or bend. Because it was difficult to measure the absorption capacity of the absorbent composite directly, it was first pulverized in the same way as water-absorbent resin particles and sieve-classified to a size of 106 to 850 μm before being measured. The weight ratio of the resin and area occupancy rate could not be measured for this composite, as it had been pulverized into particles.

Comparative Example 10

A composite was prepared in the same way as Example 1 except that the water-absorbent resin particles 1 with a particle size of 850 to 1200 μm manufactured in Manufacturing 1 were used, and the weight ratio of the resin was 25%. This was given as Comparative Example 10. All the water-absorbent resin particles adhered.

Comparative Example 12

A composite was prepared in the same way as Example 1 except that the water-absorbent resin particles 1 with a particle size of 850 to 1200 μm manufactured in Manufacturing 1 were used, and the ratio of the resin was 55%. This was given as Comparative Example 12. All the water-absorbent resin particles adhered.

The physical properties of the absorbent composites (absorbers) of Examples 18 to 27-2 and Comparative Examples 7 to 12 are shown in Table 5.

TABLE 5

| | | Absorbent resin | | | | | | |
|---|---|---|---|---|---|---|---|---|
| | | Large particles | | Small particles | | Surface | Surface | |
| | Particle No. | Av. particle size (μm) | Ratio (%) | Av. particle size (μm) | Ratio (%) | salt concentration of particles (%) | hardness of particles (N) | Base material |
| Ex. 18 | 1 | 1025 | 50 | 203 | 50 | 90 | 0.5 | Bemliese |
| Ex. 19 | 1 | 1025 | 30 | 203 | 70 | 90 | 0.5 | Bemliese |
| Ex. 20 | 1 | 1025<br><3000 | 30<br>20 | 203 | 50 | 90 | 0.5 | Bemliese |

TABLE 5-continued

| | | | | | | | | | |
|---|---|---|---|---|---|---|---|---|---|
| Ex. 21 | 3 | 1025 | 100 | — | — | | | 0.9 | Bemliese |
| Ex. 22 | 4 | 1025 | 100 | — | — | | | 5.9 | Bemliese |
| Ex. 23 | 1 | 1025 | 100 | — | — | 90 | | 0.5 | Nylon Spunbond |
| Ex. 24 | 1 | 1025 | 100 | — | — | 90 | | 0.5 | Kinocloth |
| Ex. 25 | 1 | 1025 | 100 | — | — | 90 | | 0.5 | PET Spunbond |
| Ex. 26 | 1 | 1025 | 100 | — | — | 90 | | 0.5 | PP Spunbond |
| Ex. 27 | 1 | 1025 | 100 | — | — | 90 | | 0.5 | Piason |
| Ex. 27-2 | 1 | 1025 | 100 | — | — | 90 | | 0.5 | Bemliese |
| Comp. Ex. 7 | *a | | | — | — | | | | None |
| Comp. Ex. 8 | *b | | | — | — | | | | |
| Comp. Ex. 9 | *c | — | — | — | — | — | | — | Bemliese |
| Comp. Ex. 10 | 1 | 1025 | 100 | — | — | 90 | | 0.5 | Bemliese |
| Comp. Ex. 12 | 1 | 1025 | 100 | — | — | 90 | | 0.5 | Bemliese |

| | Absorbent composite | | | | | |
|---|---|---|---|---|---|---|
| | Weight ratio (%) | Adhesion rate (%) | Total surface area Coefficient | Area occupancy rate of large particles (%) | Absorption capacity (g/g) | Absorption capacity under Pressure (g/g) |
| Ex. 18 | 65 | 98 | 0.23 | 10 | 49 | |
| Ex. 19 | 65 | 98 | 0.29 | 6 | 44 | |
| Ex. 20 | 65 | 98 | 0.2 | 8 | 41 | |
| Ex. 21 | 80.5 | 100 | 0.15 | 12 | 43.3 | |
| Ex. 22 | 80.3 | 67 | 0.15 | 14 | 39.6 | |
| Ex. 23 | 87.6 | 92 | 0.19 | 14 | 50.9 | |
| Ex. 24 | 78 | 100 | 0.19 | 14 | 57.8 | |
| Ex. 25 | 80.5 | 62 | 0.14 | 14 | 51 | |
| Ex. 26 | 86 | 51 | 0.14 | 15 | 47 | |
| Ex. 27 | 85 | 100 | 0.19 | 14 | 56 | |
| Ex. 27-2 | 94 | 95 | 0.58 | 31 | | 8 |
| Comp. Ex. 7 | — | 0 | | | 38 | 13 |
| Comp. Ex. 8 | | 0 | | | 38.7 | 12.3 |
| Comp. Ex. 9 | | — | — | — | 18.6 | 13.5 |
| Comp. Ex. 10 | 25 | 100 | 0.01 | 2 | 31.7 | |
| Comp. Ex. 12 | 55 | 100 | 0.05 | 9 | 35 | |

*a: water-absorbent resin in absorber of Pampers Cotton Care ®
*b: Water-absorbent resin in absorber of Rifure Anshin Pad ®
*c: Resin described in Comparative Example 9

Manufacturing 12

Water-absorbent resin particles 12 were manufactured in the same way as Manufacturing 1 except that the particles were classified by sieving using sieves with a sieve opening of 106 μm, 212 μm, 300 μm, 425 μm, 500 μm, 600 μm, 710 μm, 850 μm, 1000 μm, 1180 μm, 1400 μm, 2000 μm and 2500 μm.

Manufacturing 13

Water-absorbent resin particles 13 were manufactured in the same way as in Manufacturing 3 except that the particles were classified by sieving using sieves with a sieve opening of 106 μm, 212 μm, 300 μm, 425 μm, 500 μm, 600 μm, 710 μm, 850 μm, 1000 μm, 1180 μm, 1400 μm, 2000 μm and 2500 μm.

Example 28

A piece with a length of 27 cm and a width of 8 cm was cut out from Bemliese® from Asahi Kasei Fiber. Bemliese® is a nonwoven fabric made of 100% cellulose continuous-filament. As it is a cellulose nonwoven fabric, it has excellent absorption properties. Because it is made of continuous filaments, it is sufficiently strong when containing water and has excellent liquid dispersibility. A piece with a length of 27 cm and a width of 8 cm was cut out from Teflon® sheet, and a line with a length of 25 cm and a width of 6 cm was drawn on it. Another of the same was prepared. 1.5 g of the water-absorbent resin particles 12 that remained on the 1000 μm sieve from Manufacturing 12 were scattered uniformly on the inside of the line on the sheet using a 1180 μm sieve. 1.5 g of the resin particles that remained on the 212 μm sieve were scattered uniformly in the same way using a 300 μm sieve. 1.5 g of the resin particles that remained on the 1000 μm sheet were scattered in the same way on another sheet. 1.2 g of water was sprayed with an atomizer onto the Bemliese®, then it was placed on the prepared sheets to adhere the resin to both surfaces. It was dried for 10 minutes at 180° C. in an inert oven with the portion with no resin being pressed with weights to prevent shrinkage of the Bemliese®. This was given as Example 28.

Examples 29 to 32

Composites were manufactured in the same way as Example 28 except to change the particle size and the used amount of the water-absorbent resin particles 12.

1.5 g of the resin particles that remained on the 500 μm sieve were used on each side for Example 29.

1.5 g of the resin particles that remained on the 850 μm sieve were used on each side and 1.5 g of the resin particles that remained on the 212 μm sieve were used on one side for Example 30.

1.05 g of the resin particles that remained on the 710 μm sieve were used on each side and 2.4 g of resin particles that remained on the 300 μm sieve on one side for Example 31.

1.05 g of the resin particles that remained on the 710 μm sieve were used on each side and 0.975 g of resin particles that remained on the 300 μm sieve on one side for Example 32.

Example 33

A composite of Example 33 was prepared in the same way as Example 28 except that the water-absorbent resin particles 13 of Manufacturing 13 were used. The absorption amount of the composite was slightly less, as the resin particles were not in the form of ammonium salts and absorbed less compared with the water-absorbent resin of Manufacturing 12. Some particles detached after manufacturing, as the salt concentration of the surface was slightly less than that of ammonium salts.

Example 34

A composite of Example 34 was manufactured in the same way as Example 28 except that nylon Spunbond® from Asahi Kasei Fiber was used instead of Bemliese®. This was given as Example 34.

Example 35

A composite of Example 35 was manufactured in the same way as Example 28 except that Oji Kinocloth KS-40® from Oji Kinocloth was used instead of Bemliese®. Oji Kinocloth® is a nonwoven fabric of dry pulp. Because pulp is weak, the particles could be easily detached together with the pulp fibers with tweezers.

Example 36

A composite of Example 36 was manufactured in the same way as Example 28 except that PET Spunbond® from Asahi Kasei Fibers was used instead of Bemliese®. The adhesive force was slightly weak.

Example 37

A composite was manufactured in the same way as Example 28 except to change the particle size and the used amount of the resin particles using resin particles 7 of Manufacturing 7.

1.5 g of resin particles that passed through a 1400 µm sieve but remained on a 850 µm sieve were used on each sides and 1.5 g of resin particles that passed through a 300 µm sieve but remained on a 212 µm sieve were used on one side to give the composite of Example 37.

Example 38

A composite was manufactured in the same way as Example 28 except to change the particle size of resin particles using the resin particles 8 of Manufacturing 8.

1.5 g of resin particles that passed through a 1400 µm sieve but remained on a 850 µm sieve were used on each sides and 1.5 g of resin particles that passed through a 300 µm sieve but remained on a 212 µm sieve were used on one side to give the composite of Example 38.

Example 39

A composite was manufactured in the same way as Example 28 except to change the particle size of resin particles using the resin particles 7 and 8 of Manufacturings 7 and 8.

1.5 g of resin particles that passed through a 1400 µm sieve but remained on a 850 µm sieve of the resin particles 7 manufactured in Manufacturing 7 were used on each sides and 1.5 g of resin particles that passed through a 300 µm sieve but remained on a 212 µm sieve of the resin particles 8 manufactured in Manufacturing 8 were used on one side to give the composite of Example 39.

The physical properties of the absorbent composites of Examples 28 to 39 are shown in Table 6.

TABLE 6

| | Water-absorbent resin | | | | | | | Absorbent composite Weight ratio (%) |
|---|---|---|---|---|---|---|---|---|
| | Large particles | | | Small particles | | | | |
| | Particle No. | Av. particle size (µm) | Weight (material) (g) | Particle No. | Av. particle size (µm) | Weight (material) (g) | Base Material | |
| Ex. 28 | 12 | 1090 | 3 | 12 | 256 | 1.5 | Bemliese | 90 |
| Ex. 29 | 12 | 550 | 3 | — | — | 0 | Bemliese | 87 |
| Ex. 30 | 12 | 925 | 3 | 12 | 256 | 1.5 | Bemliese | 90 |
| Ex. 31 | 12 | 780 | 2.1 | 12 | 363 | 2.4 | Bemliese | 89 |
| Ex. 32 | 12 | 1090 | 2.1 | 12 | 256 | 1.5 | Bemliese | 90 |
| Ex. 33 | 13 | 1090 | 3 | 13 | 256 | 1.5 | Bemliese | 90 |
| Ex. 34 | 12 | 1090 | 3 | 12 | 256 | 1.5 | Nylon Spunbond | 93 |
| Ex. 35 | 12 | 1090 | 3 | 12 | 256 | 1.5 | Kinocloth | 87 |
| Ex. 36 | 12 | 1090 | 3 | 12 | 256 | 1.5 | PET Spunbond | 88 |
| Ex. 37 | 7 | 1125 | 3 | 7 | 256 | 1.5 | Spunlace | 91 |
| Ex. 38 | 8 | 1125 | 3 | 8 | 256 | 1.5 | Spunlace | 91 |
| Ex. 39 | 7 | 1125 | 3 | 8 | 256 | 1.5 | Bemliese | 90 |

| | Absorbent composite | | | | | | |
|---|---|---|---|---|---|---|---|
| | Adhesion rate (%) | Total surface area coefficient | Area occupancy rate of large particles (%) | Total area occupancy rate (%) | Absorption capacity (g/g) | Absorption capacity after 1 min (g/g) | Bending resistance (mm) |
| Ex. 28 | <99 | 0.77 | 14 | 55 | 55 | 15 | 70 |
| Ex. 29 | <99 | 0.49 | 26 | 25 | 53 | 15 | 80 |
| Ex. 30 | <99 | 1 | 16 | 60 | 52 | 14 | 71 |

TABLE 6-continued

| Ex. 31 | <99 | 0.66 | 13 | 66 | 60 | 14 | 69 |
| Ex. 32 | <99 | 0.71 | 15 | 61 | 54 | 14 | 77 |
| Ex. 33 | <99 | 0.75 | 14 | 53 | 50 | 10 | 70 |
| Ex. 34 | 90 | 0.78 | 15 | 50 | 52 | 12 | 73 |
| Ex. 35 | 98 | 0.76 | 14 | 54 | 50 | 16 | 60 |
| Ex. 36 | 60 | 0.75 | 14 | 50 | 50 | 10 | 40 |
| Ex. 37 | <99 | 0.63 | 13 | 54 | 54 | 13 | 73 |
| Ex. 38 | <99 | 0.62 | 14 | 56 | 56 | 16 | 68 |
| Ex. 39 | <99 | 0.7 | 13 | 57 | 57 | 14 | 71 |

Example 40

The apparatus shown in FIG. 17 was prepared. (a) is a fabric roll (base material) of Bemliese® from Asahi Kasei Fiber with a width of 500 mm. The measured density of this fabric was 28 g/m². Gas line and water line were attached to the spray nozzle of water atomizer (b). The sprayed amount of water was adjusted by adjusting the gas pressure and the water pressure in the spray nozzle. A water-absorbent resin particle hopper (d1) (supply part) was provided. Gas blower (i1) was provided on the top of drum (e1) to blow off water-absorbent resin particles from hopper (d1) that adhered to other parts than the dimples on the drum. Dry warm air blower (j1) was provided to dry the surface of the drum before it came into contact with the particles. Drum (e1) had a diameter of 500 mm and a width of 500 mm. The structure of the dimples on the drum surface is shown in FIGS. 18 and 19. FIG. 18 shows the positional relationship of the dimples as seen from above the drum surface. The dimples were arranged such that the distance between the centers of adjacent dimples was about 3.1 mm. FIG. 19 is a cross-section view of a dimple in the depth direction, showing a hole structure extending from the surface of the drum to the inside of the drum, wherein the opening on the drum surface is a circle with a diameter of 1.5 mm and narrows towards the inside of the drum to a diameter of 0.7 mm at a depth of 0.8 mm, and then maintains a diameter of 0.7 mm to the inside of the drum.

Fabric (c), which passed under drum (e1) and to one surface of which the resin particles (f) adhere, then passes between press rolls (l), which strengthens the adhesion between the resin particles and the fabric. The same equipment mentioned above was used for drum (e2), upper hopper (d2), gas blower (i2) and dry warm air blower (j2) as for drum (e1), hopper (d1), gas blower (i1) and dry warm air blower (j1), respectively. The fabric was conveyed by conveyer belt (k) from beneath drum (e2) to the exit of dryer (g). In dryer (g), a distance that the fabric travels is about 2 m, and warm air was blown from the fabric exit towards the fabric entrance. Final take-up roll (h) was operated by hand in order to control the rotational speed so as to maintain a roughly constant deflection of the fabric between the belt conveyer and the final roll.

FIG. 20 shows a structure including internal structure of drum (e1).

The interior of drum (e1) is divided by partition (o1) into reduced pressure space (q1) and normal pressure space. Gas blower (m1) is fixed to the position where the drum contacts the fabric, and emits gas to blow out particles in holes that pass the gas blower (m1). Drum (e1) also has another gas blower (n1), which emits gas to blow out particles that were not blown onto the fabric into residual resin container (p1).

FIG. 21 shows a structure including internal structure of drum (e2).

The interior of drum (e2) is divided by partition (o2) into reduced pressure space (q2) and normal pressure space. Gas blower (m2) is fixed to the position where the drum contacts the fabric, and emits gas to blow out particles in holes that pass the of gas blower (m2). Drum (e2) also has another gas blower (n2), which emits gas to blow out residual resin that were not blown onto the fabric onto the fabric once again.

The water-absorbent resin particles used here were 850 to 1200 µm sized particles manufactured by the method given in Manufacturing 1. 1 kg of these resin particles was placed in each hopper (d1) and hopper (d2). Every time the amount of resin in each hopper decreased to about 300 g during operation, resin was added to the hopper up to 1 kg of resin. This operation was repeated to prevent the resin in the hoppers from being exhausted during operation. Reduced pressure spaces (q1) and (q2) were depressurized from near the axis so as to maintain the pressure of about 700-750 mmHg. Air was blown from gas blowers (i1) and (i2), and the volume of blown air was adjusted so as to bring most of the resin adhere to other parts than the dimples back to the hoppers. Warm dry air was blown from dry warm air blowers (j1) and (j2) to dry the surfaces of the drums. Gas was blown from gas blowers (m1), (m2), (n1) and (n2). Nitrogen gas at 180° C. was supplied through dryer (g) from the exit towards the entrance at a rate of 50 m³/hr. The amount of water sprayed by the water sprayer was adjusted so that the water content of the Bemliese would be 20 g water/m² when the rate of movement of the Bemliese was 0.2 m/minute.

Drums (e1) and (e2) and conveyer belt (k) were rotated so as to ensure the fabric move smoothly, and operation was initiated after adjusting the speed of the fabric to about 0.3 m/minute.

During operation, composite roll (h) was operated by hand so as to maintain a roughly constant deflection between conveyer belt (k) and composite roll (h).

The fabric coming out from the roll 20 to 60 minutes after the initiation of operation was evaluated in various ways.

(Evaluation of Manufactured Absorbent Composite: Adhesion Between Resin and Fabric)

A 10 cm square piece was cut out from the absorbent composite manufactured in Example 40 and the mode of adhesion between the fibers in the nonwoven fabric and the absorbent resin was observed with an optical microscope. The fibers passed through the resin.

(Evaluation of Manufactured Absorbent Composite: the Weight Ratio of Resin of Absorbent Composite)

Part of the absorbent composite manufactured in Example 40 was divided into pieces with a length of 50 cm and 10 pieces of these were selected to measure the ratio of the resin. The ratio of the resin was between 82 and 86 wt %. That is, there was little variation in the weight ratio of the resin in the manufactured absorbent composite. This absorbent composite was divided into pieces with a length of 50 cm and 10 pieces of these were selected at random to measure the ratio of the resin content. The ratio of the resin varied greatly between 70 wt % and 90 wt %, showing that the fabric did not have a stable weight ratio of resin. The weight ratio of the resin in the absorbent composite was calculated by the same methods used in Example 42 below.

(Evaluation of Manufactured Absorbent Composite: Adhesion Between Absorbent Resin and Fabric)

A piece with a length of 50 cm was cut out from the absorbent composite manufactured in Example 40 and was hanged on a bar fixed at about 1 m in height, and the bar was shaken up and down for 60 seconds at a rate of 15 cm/second with a shaking width of 30 cm. The weight ratio of the resin of the absorbent composite was 84 wt %, and only 5 resin particles fell off.

(Evaluation of Manufactured Absorbent Composite: Absorption Amount Under No Pressure)

The amount absorbed under no pressure by the absorbent composite manufactured in Example 40 was 61 g/g. The absorption capacity per unit area was 1 g/cm$^2$.

Example 41

The operation was carried out in the same way as Example 40 except that the water-absorbent resin particles of Manufacturing 3 were used.

(Evaluation of Manufactured Absorbent Composite: Area Occupancy Rate of Absorbent Composite)

The area occupancy rate per one surface of the absorbent composite manufactured in Example 41 was 15.5%.

(Evaluation of Manufactured Absorbent Composite: Adhesion Between Water-Absorbent Resin and Fabric)

A piece with a length of 50 cm was cut out from the absorbent composite manufactured in Example 41 and was hanged on a bar fixed at about 1 m high, and the bar was shaken for 60 seconds up and down at 15 cm/second with a shaking range of 30 cm. The weight ratio of the resin of the absorbent composite was 85 wt %, and only 20 particles of resin fell off.

Example 42

The Water Content of the Base Material is Less than 0.5 Wt %

The operation was carried out in the same way as Example 40 except that the amount of water sprayed by the atomizer was reduced so as to adjust the water content of the Bemliese after having passed under the water atomizer to 0.3 wt %.

The fabric coming out from the machine 20 to 60 minutes after the initiation of operation was used. A piece with a length of 50 cm was cut out from this absorbent composite and was hanged on a bar fixed at about 1 m high, and the bar was shaken 60 times at 30 cm/second with a shaking range of 30 cm. The weight ratio of resin of the absorbent composite was 30 wt % or less. Few resin particles adhered to the fabric that had a low water content. The amount of resin of the absorbent composite is determined by subtracting the weight of the fabric in the absorbent composite from the total weight of the absorbent composite. The weight of the fabric in the absorbent composite was determined by multiplying 0.25 m$^2$ by the density of the fabric in the dry state before use (g/m$^2$) which was measured in advance with the assumption that area of the piece with a length of 50 cm which was cut out for this measurement is 0.25 m$^2$. The weight ratio of the resin in the absorbent composite is given as a percentage and is obtained by dividing the weight of resin in the absorbent composite as calculated by the aforementioned method by the total weight of the absorbent composite.

Example 43

The Water-absorbent Resin Particles Containing More than 50 Wt % Water were Used)

1 kg of the water-absorbent resin particles were placed in a 10 L Teflon container, and 2 kg of water was added all at once with stirring vigorously. After almost all of the water had been absorbed by the water-absorbent resin particles, it was stop to be stirred. The operation was carried out in the same way as Example 40 except that these were used as the water-absorbent resin particles. The fabric coming out from the machine 20 to 60 minutes after the initiation of operation was used. This absorbent composite was divided into pieces with a length of 50 cm and 10 of these pieces were taken at random and the weight ratios of the resin were measured. They varied greatly between 70 wt % and 90 wt %, showing that the weight ratio of the resin was not steady. The weight ratio of the resin of the absorbent composite was calculated by the same methods as in Example 42.

Example 44

The Outer Diameter of the Dimples on the Drum Surface of Coating Machine was Larger than 3 Times the Average Particle Size of the Water-absorbent Resin The operation was carried out in the same way as Example 40 except that drums having surface dimples with an outer diameter of 4 mm were used as drums (e1) and (e2). The fabric coming out from the machine 20 to 60 minutes after the initiation of operation was used. This absorbent composite was divided into pieces with a length of 50 cm and 10 of these pieces were taken at random and the weight ratios of the resin were measured. They varied greatly between 92 wt % and 75 wt %, showing that the weight ratio of the resin was not steady. The weight ratio of the resin of the absorbent composite was calculated by the same methods as in Example 42.

Example 45

The Depth of the Dimples on the Drum Surface of Coating Machine was Larger than 2 Times the Average Particle Size of the Water-absorbent Resin The operation was carried out in the same way as Example 40 except that drums having surface dimples with a depth of 4 mm rather than 0.8 mm were used as drums (e1) and (e2). The fabric coming out from the machine 20 to 60 minutes after the initiation of operation was used. This absorbent composite was divided into pieces with a length of 50 cm and 10 of these pieces were taken at random and the weight ratios of the resin were measured, they varied greatly between 92 wt % and 75 wt %, showing that the weight ratio of the resin was not steady. The weight ratio of the resin of the absorbent composite was calculated by the same methods as in Example 42.

Example 46

PET Nonwoven Fabric was Used

The coating machine was operated in the same way as Example 40 except that PET nonwoven fabric was used as the fabric. The fabric coming out from the machine 20 to 60 minutes after the initiation of operation was used. A piece with a length of 50 cm was cut out from this absorbent composite and hanged on a bar at about 1 m high and the bar was shaken up and down for 60 seconds at a rate of 15 cm/second with a shaking range of 30 cm. The weight ratio of the resin of the absorbent composite was 30 wt % or less, and few resin particles adhered to the PET nonwoven fabric. The weight ratio of the resin of the absorbent composite was calculated as in Example 42.

Example 47

PP Nonwoven Fabric was Used

The coating machine was operated in the same way as Example 40 except that PP nonwoven fabric was used as the fabric. The fabric coming out from the machine 20 to 60 minutes after the initiation of operation was used. A piece with a length of 50 cm length was cut out from this absorbent composite and hanged on a bar fixed at about 1 m high and the bar was shaken 60 times at a rate of 30 cm/second with a shaking range of 30 cm. The weight ratio of the resin of the absorbent composite was 30 wt % or less, and few resin particles adhered to the PP nonwoven fabric. The weight ratio of the resin of the absorbent composite was calculated as in Example 42.

Example 48

A piece with a length of 37 cm and with a width of 21 cm was cut out from Bemliese®. A piece with a length of 37 cm and with a width of 21 cm was cut out from Teflon® in the same way, and a line with a length of 35 cm and a width of 19 cm was drawn on it. Another of the same was prepared. 6.6 g of the particles with a particle size of 1000 to 1180 µm of Manufacturing 1 were used as the large particles and scattered uniformly on the inside of the line on the sheet using a 1180 µm sieve. Likewise, 6.65 g of the particles with a particle size of 212 to 300 µm of Manufacturing 1 were used as the small particles and scattered uniformly using a 300 µm sieve. 6.7 g of the particles with a particle size of 1000 to 1180 µm were scattered in the same way on another sheet. 8 g of water was applied with an atomizer over the Bemliese®, then it was placed and pressed on the resin particles. A further 2 g of water was then applied to the Bemliese®, and adhere the resin particles to the reverse surface. 3 g of water was sprayed on the Bemliese®, and it was dried for 10 minutes at 180° C. in an inert oven with the portion with no resin being pressed with weights to prevent shrinkage of the Bemliese®.

A Munee Nobiru Fit® M size diaper from Unicharm Co., Ltd. was prepared, the top sheet and back sheet were separated from by melting the hot melt adhesive with the heat of dryer. A piece with a length of 33 cm and a width of 17 cm was cut out from the manufactured absorbent composite and was sandwiched between the sheets, and the edges of the top sheet and the back sheet that were not in contact with the absorbent composite were adhered to each other with the non-corrosive quick-drying adhesive seal material TSE397 from GE Toshiba Silicones Co., Ltd. to give a bodily fluid-absorbing article of Example 48.

Example 49

The absorber of a Munee Nobiru Fit® M size diaper from Unicharm Co., Ltd. was broken apart and the pulp and water-absorbent resin were simultaneously set in a screened shaker. The pulp was collected with tweezers, as it aggregated. This operation was repeated to completely separate the water-absorbent resin from the pulp. An absorbent composite was prepared in the same way as Example 48, and the 3 g of pulp was scattered thereon using a sieve. This was sandwiched between the top sheet and the back sheet in the same way as Example 48 to give a bodily fluid-absorbing article. The feeling of the article was improved by introducing a pulp layer.

Example 50

A bodily fluid-absorbing article was prepared in the same way as Example 48 except that the particle size of the large particles was changed from 500 to 600 µm to 1000 to 1180 µm, and small particles were not used. This was used as Example 50.

Example 51

A bodily fluid-absorbing article was prepared in the same way as Example 48 except that the particle size of the large particles was changed to 710 to 850 µm and the used mount of the large particles was changed to 4.65 g per one side and the particle size of the small particles was changed to 300 to 425 µm and the used mount of the small particles was changed to 10 g. This was used as Example 51.

Example 52

A bodily fluid-absorbing article was prepared in the same way as Example 48 except that the resin of Manufacturing 3 was used. This was used as Example 52.

Example 53

A bodily fluid-absorbing article was prepared in the same way as Example 48 except that the absorbent composite and water-impermeable sheet were adhered to each other with water-repellent hot melt adhesive ME117 from Japan NSC Co., Ltd. as shown in FIG. 22. This was used as Example 53. The adhesive was spread vertically and horizontally on the absorbent composite as shown in FIG. 22. The absorbent composite was stable and did not shift in the article.

Example 54

A bodily fluid-absorbing article was prepared in the same way as Example 48 except that the resin particles with a particle size of 710 to 850 µm were used as the large particles on both sides, 6.1 g per one side, and 4 g of the resin particles with a particle size of 212 to 300 µm were used as the small particles. This was used as Example 54.

Comparative Example 13

A Unicharm Co. M-size Munee Nobiru Fit® diaper was used as Comparative Example 13. The absorber, which was a mixture of pulp and water-absorbent resin, was thick and had low absorption ability.

Comparative Example 14

An M-size Pampers Cotton Care® diaper from P&G Co., Ltd. was used as Comparative Example 14. The absorber, which was a mixture of pulp and water absorbent resin, was thick and had low absorption capability.

The physical properties of the bodily fluid-absorbing articles of Examples 48 to 54 and Comparative Examples 13 and 14 are shown in Table 7.

TABLE 7

| | Absorbent composite | | | | | | Bodily fluid-absorbing article | | | |
|---|---|---|---|---|---|---|---|---|---|---|
| | Absorbent resin Particle | Weight | Weight ratio | Adhesion rate | Absorption capacity | Absorption capacity After 1 min. | Bending resistance | Rewetting (g) | | | Liquid dispersion distance |
| | No. | (g) | (%) | (%) | (g/g) | (g/g) | (mm) | 1st | 2nd | 3rd | (mm) |
| Ex. 48 | 1 | 16 | 90 | 100 | 55 | 15 | 70 | 0.4 | 8 | 18 | 280 |
| Ex. 50 | 1 | 12 | 87 | 100 | 53 | 15 | 80 | 0.3 | 9 | 19 | 260 |
| Ex. 51 | 1 | 14 | 89 | 100 | 60 | 14 | 69 | 0.8 | 14 | 21 | 270 |
| Ex. 52 | 3 | 17 | 90 | 100 | 50 | 10 | 70 | 5 | 17 | 24 | 275 |
| Ex. 53 | 1 | 16 | 90 | 100 | 55 | 15 | 70 | 0.3 | 7 | 17 | 270 |
| Ex. 54 | 1 | 13 | 88 | 100 | 68 | 14 | 74 | 0.3 | 10 | 20 | 285 |
| CE 13 | *d | 28 | — | 0 | 21 | 7 | — | 12 | 40 | 51 | 210 |
| CE 14 | *e | 24 | — | 0 | 21 | 9 | — | 1.6 | 28 | 40 | 180 |

*d: Absorbent resin from absorber of Munee Nobiru Fit ®
*e: Absorbent resin from absorber of Pampers Cotton Care ®

Example 55

A bodily fluid-absorbing article of Example 55 was prepared in the same way as Example 48 except for the following changes.

Pieces with a length of 37 cm and a width of 25 cm were cut from the Bemliese® and Teflon sheet. A line with a length of 35 cm and a width of 23 cm was drawn on the Teflon sheet. 8.0 g and 8.1 g of large particles were dispersed on the front surface and the back surface, respectively, and 8 g of small particles were dispersed.

A piece with a length of 33 cm and a width of 21 cm was cut from the manufactured composite, and inserted between the top sheet and the back sheet with being folded as shown in FIG. 23.

Example 56

A bodily fluid-absorbing article was prepared in the same way as Example 55 except that the particle size of the large particles was changed to 500 to 600 μm, and no small particles were used. This was used as Example 56.

Example 57

A bodily fluid-absorbing article was prepared in the same way as Example 55 except that the water-repellent hot-melt adhesive ME117 from Japan NSC Co., Ltd. was used as the adhesive.

The physical properties of the bodily fluid-absorbing articles of Examples 55 to 57 are shown in Table 8. This was used as Example 57.

TABLE 8

| | Absorbent composite | | | | | | Bodily fluid-absorbing article | | | | | |
|---|---|---|---|---|---|---|---|---|---|---|---|---|
| | Absorbent resin Particles | Weight | Weight ratio | Adhesion rate | Absorption capacity | Absorption capacity after 1 min | Rewetting (g) | | | Liquid dispersion distance | Wetting drip volume | Wetting |
| | No. | (g) | (%) | (%) | (g/g) | (g/g) | 1st | 2nd | 3rd | (mm) | (ml) | coefficient |
| Ex. 55 | 1 | 20 | 90 | 100 | 55 | 15 | 0.2 | 6 | 16 | 300 | 160 | 5300 |
| Ex. 56 | 1 | 15 | 87 | 100 | 55 | 15 | 0.5 | 7 | 18 | 275 | 140 | 6000 |
| Ex. 57 | 1 | 20 | 90 | 100 | 55 | 15 | 0.2 | 6 | 15 | 310 | 165 | 5100 |
| CE 13 | *d | 28 | — | 0 | 21 | 7 | 12 | 40 | 51 | 210 | 42 | 800 |
| CE 14 | *e | 24 | — | 0 | 21 | 9 | 1.6 | 28 | 40 | 180 | 55 | 800 |

*d: Absorbent resin from absorber of Munee Nobiru Fit ®
*e: Absorbent resin from absorber of Pampers Cotton Care ®

Example 58

A bodily fluid-absorbing article of Example 58 was prepared in the same way as Example 48 except that the absorbent composite was adhered to the water-permeable sheet and water-impermeable sheet in the pattern shown in FIG. 24.

Example 59

A bodily fluid-absorbing article of Example 59 was prepared in the same way as Example 58 except that the water-repellent hot-melt adhesive ME117 from Japan NSC Co., Ltd. was used as the adhesive. (Example 60)

A bodily fluid-absorbing article of Example 60 was prepared in the same way as Example 50 except that the absorbent composite was adhered to the water-permeable sheet and water-impermeable sheet in the pattern shown in FIG. 24. The physical properties of the bodily fluid-absorbing articles of Examples 58 to 60 are shown in Table 9.

TABLE 9

| | Absorbent composite | | | | | Bodily fluid-absorbing article | | | | | |
|---|---|---|---|---|---|---|---|---|---|---|---|
| Absorbent resin Particles | Weight | Weight ratio | Adhesion rate | Absorption capacity | Absorption capacity after 1 min | Rewetting (g) | | | Liquid dispersion distance | Lengthwise dispersion | Distribution area |
| No. | (g) | (%) | (%) | (g/g) | (g/g) | 1st | 2nd | 3rd | (mm) | | (cm²) |
| Ex. 58 | 1 | 16 | 90 | 100 | 55 | 15 | 0.3 | 7 | 18 | 300 | 2.8 | 300 |
| Ex. 59 | 1 | 16 | 90 | 100 | 55 | 15 | 0.2 | 7 | 16 | 310 | 3 | 360 |
| Ex. 60 | 1 | 12 | 87 | 100 | 53 | 15 | 0.5 | 8 | 19 | 275 | 2.7 | 270 |
| CE 13 | *d | 28 | — | 0 | 21 | 7 | 12 | 40 | 51 | 210 | 1.1 | 90 |
| CE 14 | *e | 24 | — | 0 | 21 | 9 | 1.6 | 28 | 40 | 180 | 1.1 | 80 |

*d: Absorbent resin from absorber of Munee Nobiru Fit ®
*e: Absorbent resin from absorber of Pampers Cotton Care ®

DESCRIPTION OF THE DRAWINGS

FIG. 13 shows an example of an adhesive application pattern.

FIG. 22 shows the pattern of adhesive on the bodily fluid-absorbing article of Example 53.

FIG. 24 is a simplified diagram of the structure of the bodily fluid-absorbing article of Example 58.

Figure 1:
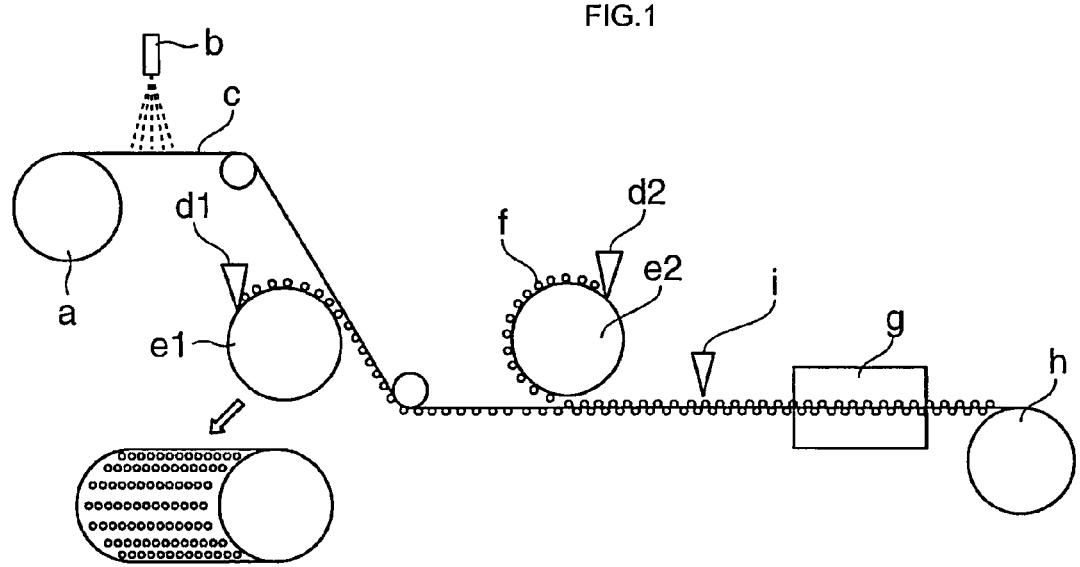
FIG. 1 is an explanatory diagram of a desirable manufacturing device for manufacturing the absorbent composite of the present invention.
Figure 2:
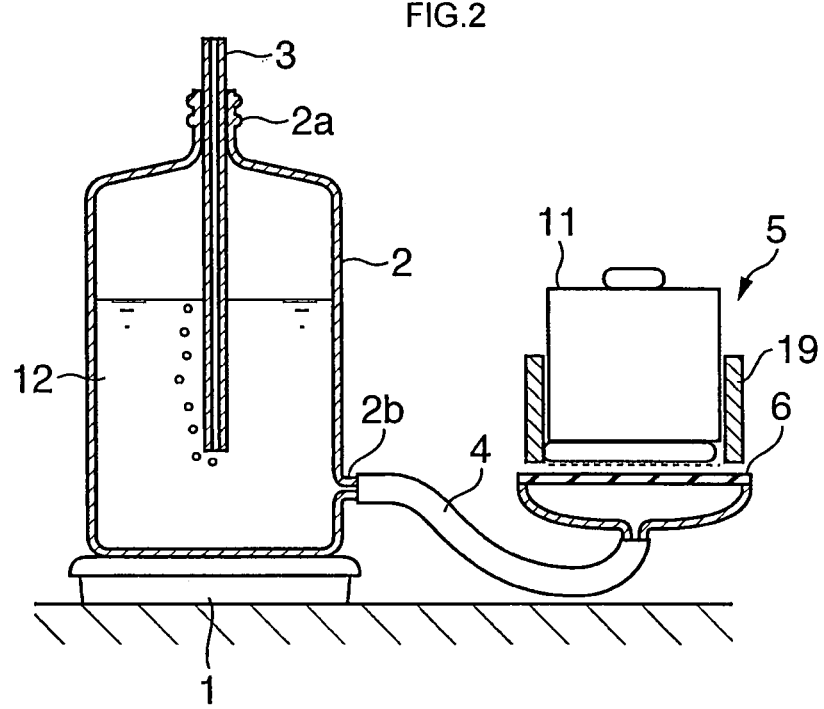
FIG. 2 is an explanatory diagram of a measurement unit for measuring the absorption capacity of an absorbent composite under pressure in the present invention.
Figure 3:
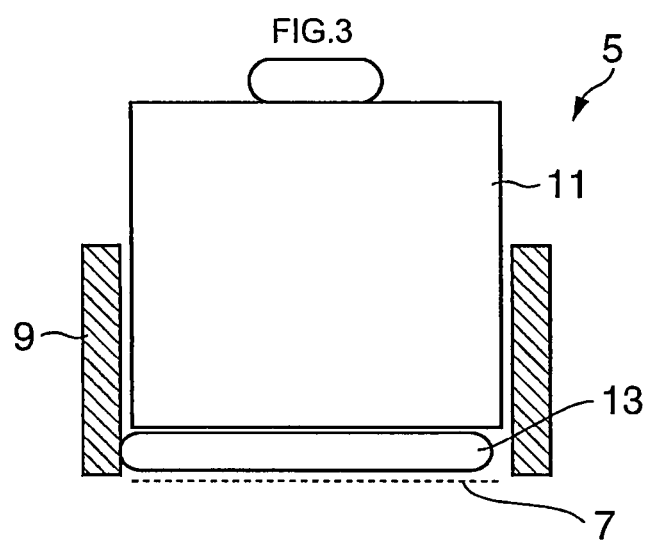
FIG. 3 shows an enlarged explanatory view of the measurement part 5 in FIG. 2.
Figure 4:
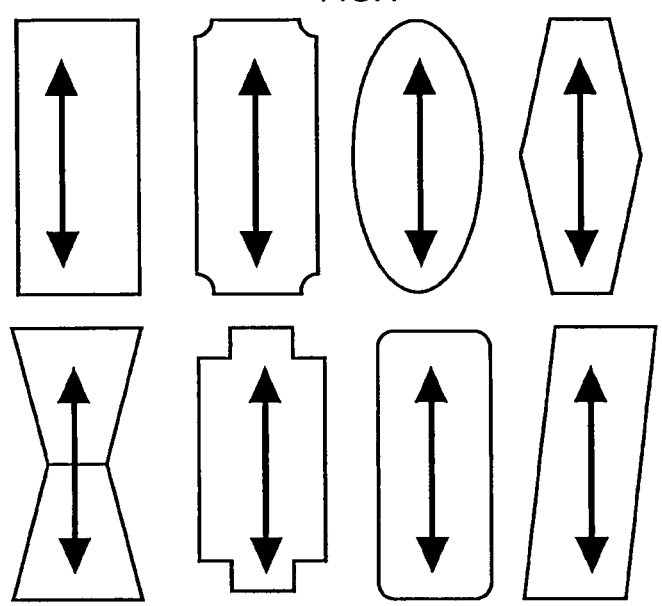
FIG. 4 shows examples of shapes of absorbent composites with the longer directions.
Figure 5:
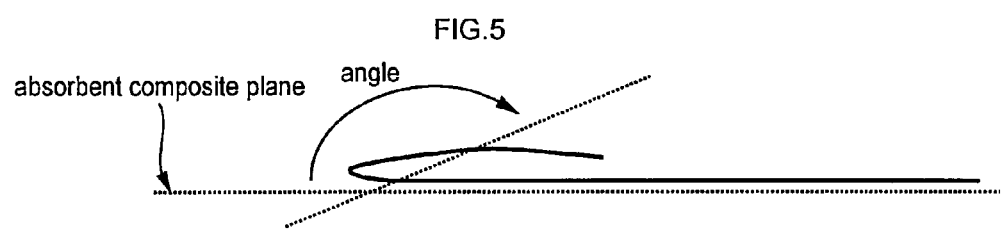
FIG. 5 shows an example of folding of an absorbent composite.
Figure 6:
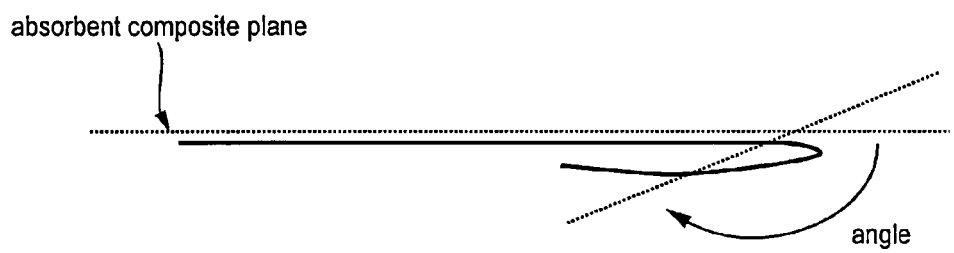
FIG. 6 shows an example of folding of an absorbent composite.
Figure 7:
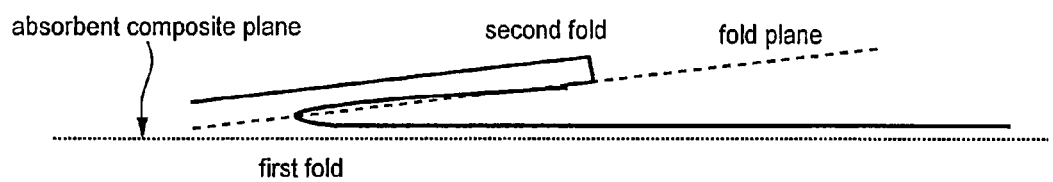
FIG. 7 shows an example of folding of an absorbent composite.
Figure 8:
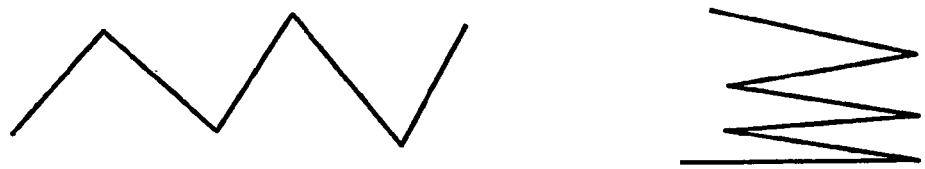
FIG. 8 shows an example of folding of an absorbent composite.
Figure 9:
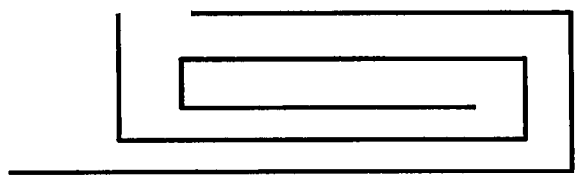
FIG. 9 shows an example of folding of an absorbent composite.
Figure 10:
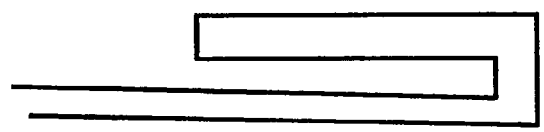
FIG. 10 shows an example of folding of an absorbent composite.
Figure 11:
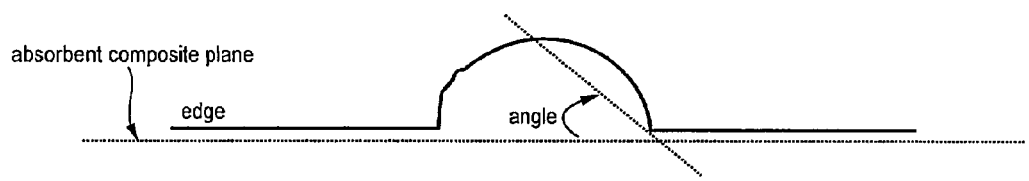
FIG. 11 shows an example of folding of an absorbent composite.
Figure 12:
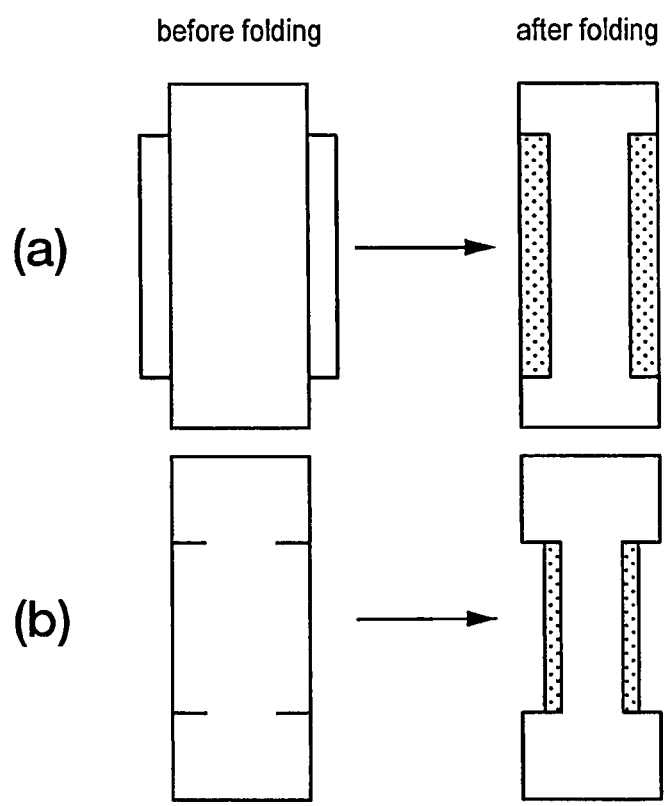
FIG. 12 shows an example of folding of an absorbent composite.
Figure 14:
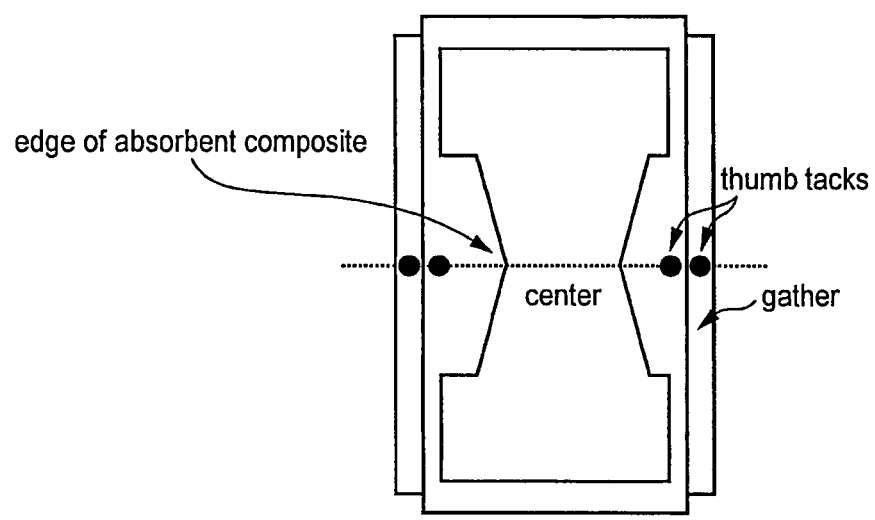
FIG. 14 is an explanatory diagram of a leakage evaluation test.
Figure 15:
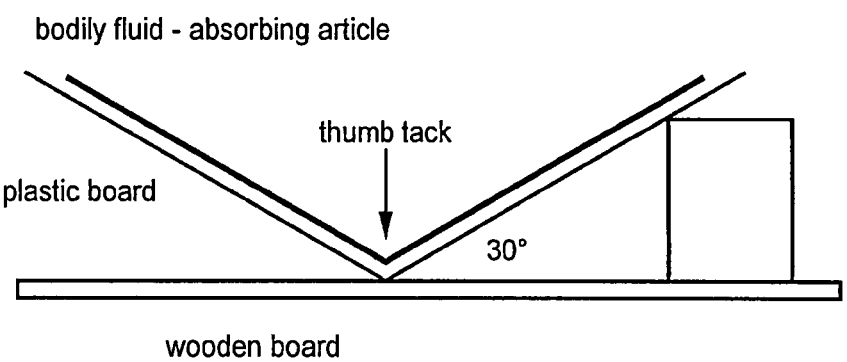
FIG. 15 is an explanatory diagram of a leakage evaluation test.
Figure 16:
FIG. 16 is an electron microscope image showing adhesion with the fibers penetrating the absorbent resin.
Figure 17:
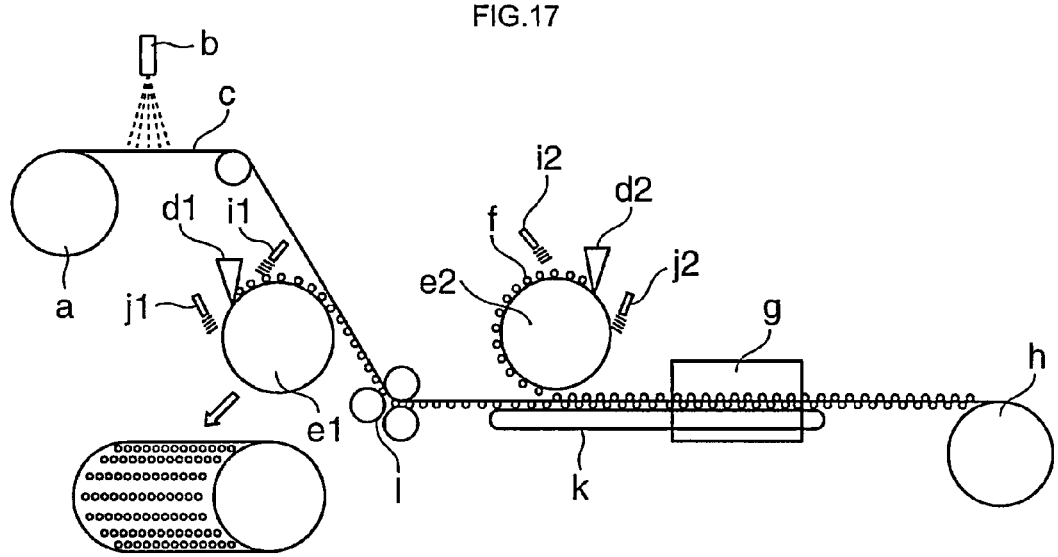
FIG. 17 is an explanatory diagram of one example of a manufacturing device for manufacturing the absorbent composite of the present invention.
Figure 18:
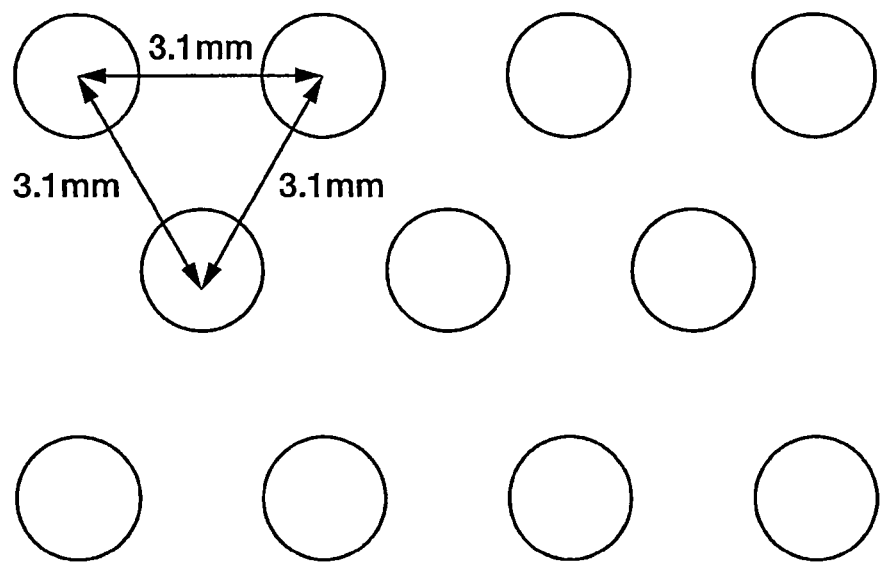
FIG. 18 is a simplified diagram showing the arrangement of dimples on the drum surface in the device of FIG. 17.
Figure 19:
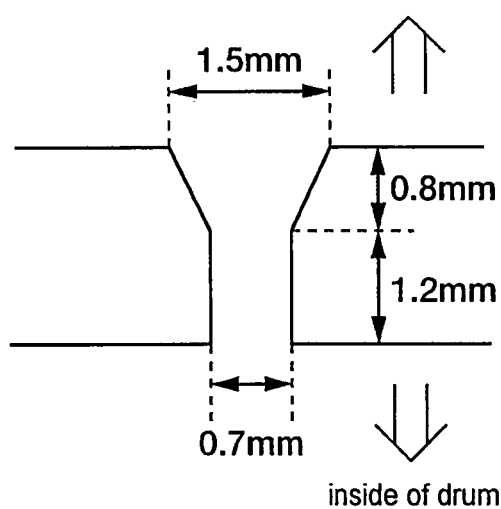
FIG. 19 is a simplified diagram showing the dimples on the drum surface in the device of FIG. 17 in the direction of depth.
Figure 20:
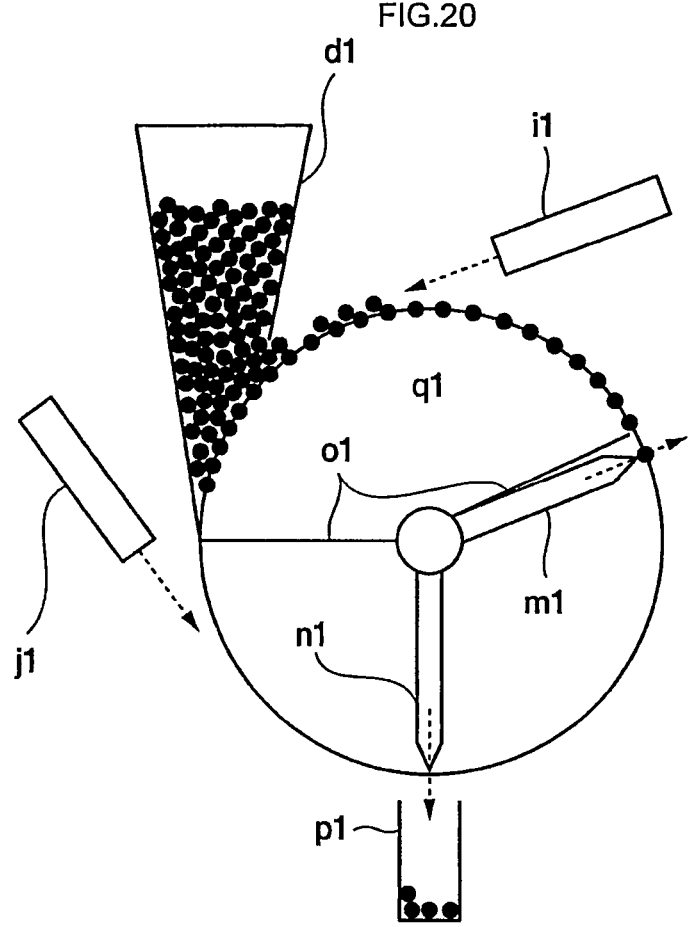
FIG. 20 is a simplified diagram showing the first drum in the device of FIG. 17.
Figure 21:
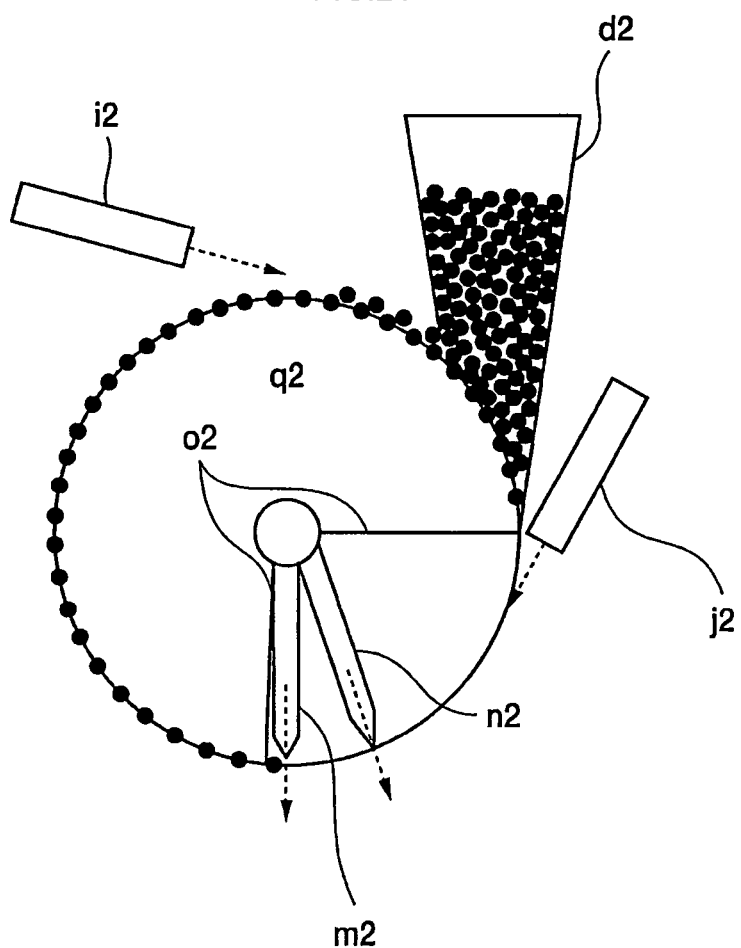
FIG. 21 is a simplified diagram showing the second drum in the device of FIG. 17.
Figure 23:
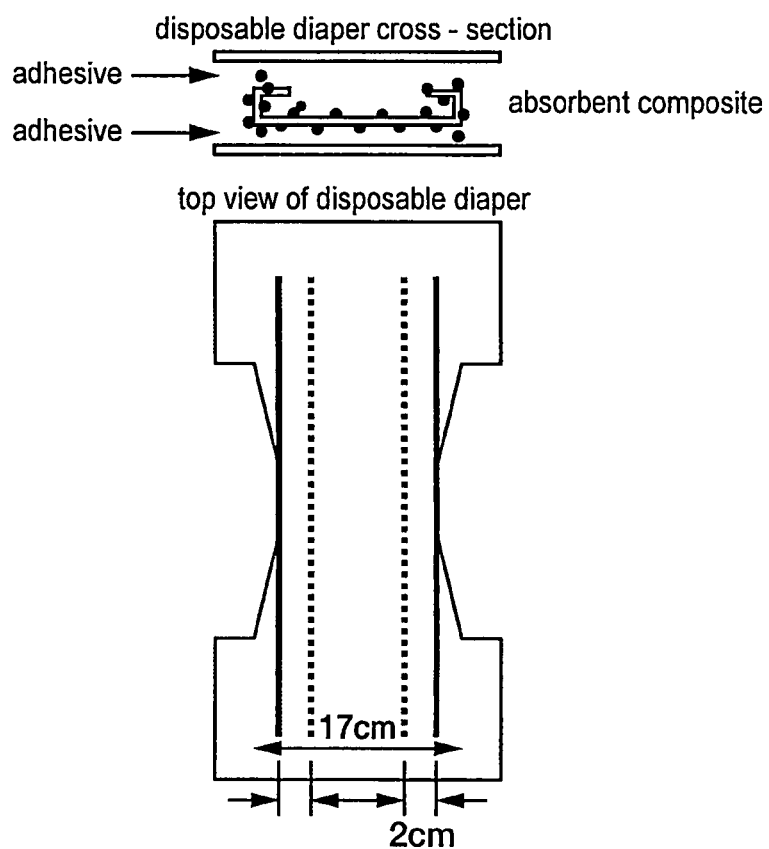
FIG. 23 is a simplified diagram of the structure of the bodily fluid-absorbing article of Example 55.

We claim:

1. An absorbent composite comprising: a base material and water-absorbent resin particles;
   wherein the following conditions are fulfilled:
   the weight ratio of water-absorbent resin relative to the total weight of the base material and water-absorbent resin is 65 to 99 wt %;
   the water-absorbent resin particles adhering directly to the base material constitute 50 wt % or more of the total water-absorbent resin particles;
   the average absorption capacity of the water-absorbent resin particles is greater than 50 g/g;
   the surface strength of the water-absorbent resin particles before being adhered to the base material is 0.1 to 5.5 N; and
   the amount of residual monomers in the water-absorbent resin is 200 ppm or less.

2. The absorbent composite according to claim 1, wherein the resin area occupancy rate of the water-absorbent resin particles in the particle size range of from 550 μm to 2100 μm is 1 to 30% on at least one side of the base material.

3. The absorbent composite according to claim 1, wherein the total surface area coefficient is 0.3 to 3.

4. The absorbent composite according to claim 1, wherein the water-absorbent resin particles comprises larger particles having a particle size range of from 550 μm to 2100 μm,
at least some of the larger particles are adhered to the base material, and
the larger particles adhered to the base material having a surface salt concentration that is at least 10 mol % lower than a salt concentration at a center thereof.

5. The absorbent composite according to claim 1, wherein the particle size distribution of the water-absorbent resin particles fulfills the following conditions:
particles that can pass through a sieve with a sieve opening of 300 μm constitute 10 to 50 wt % of the total weight of water-absorbent resin; and
Particles that cannot pass through a sieve with a sieve opening of 3000 μm constitute 10 wt % or less of the total weight of water-absorbent resin.

6. The absorbent composite according to claim 1, wherein the water-absorbent resin particles are amorphous resin particles manufactured by aqueous solution polymerization followed by pulverization and/or resin particles manufactured by reverse-phase suspension polymerization.

7. The absorbent composite according claim 1, wherein the absorption capacity under pressure of the water-absorbent resin particles is 20 g/g or more.

8. The absorbent composite according to claim 1, wherein the water-absorbent resin constituting the water-absorbent resin particles is a resin having carboxylic acid groups in the side chains, and 50% or more of the acid groups in the water-absorbent resin before being adhered to the base material are neutralized in the form of ammonium salts.

9. The absorbent composite according to claim 1, wherein the water-absorbent resin constituting the water-absorbent resin particles is a copolymer consisting primarily of a polyacrylic acid salt.

10. The absorbent composite according to claim 1, wherein the contact angle of the base material with an aqueous ammonium polyacrylate solution with a solution viscosity of 74 cps is 130° or less.

11. The absorbent composite according to claim 1, wherein the tensile breaking strength of the base material after having absorbed saline is 0.6 N/20 mm or more in both a lengthwise direction and a crosswise direction.

12. The absorbent composite according to claim 1, wherein the base material is fabric and/or paper.

13. The absorbent composite according to claim 1, wherein the base material fulfills the following conditions:
the ratio between the tensile breaking elongation in a lengthwise direction and that in a crosswise direction is 1:1.2 to 1:10; and
the ratio between the tensile breaking strength in the lengthwise direction and that in the crosswise direction is 1.2:1 to 10:1.

14. The absorbent composite according to claim 1, wherein the absorption capacity of the base material is 6 g/g or more.

15. The absorbent composite according to claim 1, wherein the absorption speed of the base material is 0.35 mg/second or more.

16. The absorbent composite according to claim 1, wherein the base material is paper and/or fabric consisting of cellulose fibers.

17. The absorbent composite according to claim 16, wherein the base material is cellulose non-woven fabric.

18. The absorbent composite according to claim 1, wherein the base material has edges that are folded and fixed in place.

19. The absorbent composite according to claim 1, wherein an adhesive is applied linearly in a length direction.

20. The absorbent composite according to claim 19, wherein the adhesive is a hot-melt adhesive.

21. A method for manufacturing an absorbent composite comprising a base material and water-absorbent resin particles, comprising: making the base material and/or the water-absorbent resin absorb water, followed by removing water from and drying the base material and the water-absorbent resin while making them be in contact with each other, wherein the following conditions are fulfilled:
the weight ratio of water-absorbent resin relative to the total weight of the base material and water-absorbent resin is 65 to 99 wt %;
the water-absorbent resin particles adhering directly to the base material constitute 50 wt % or more of the total water-absorbent resin particles;
the average absorption capacity of the water-absorbent resin particles is greater than 50 g/g;
the surface strength of the water-absorbent resin particles before being adhered to the base material is 0.1 to 5.5 N; and
the amount of residual monomers in the water-absorbent resin is 200 ppm or less.

22. The method for manufacturing an absorbent composite according to claim 21, comprising the following steps:
making the water-absorbent resin particles and/or the base material absorb water in the amount of 10 to 3000 wt % of the water-absorbent resin particles to be adhered;
making the base material be in contact with the water-absorbent resin particles; and
removing water from and drying the base material and the water-absorbent resin particles.

23. The method for manufacturing an absorbent composite according to claim 21, wherein drying is carried out under heat conditions at a heating temperature of 70 to 350° C. with a treatment time of 1 to 1000 seconds.

24. The method for manufacturing an absorbent composite according to claim 23, wherein the water-absorbent particles used are particles where the salt concentration on the surface has been reduced by drying treatment with heating by 10% or more compared to the value before treatment.

25. A method for manufacturing an absorbent composite comprising a base material and water-absorbent resin particles, using a device comprising: a base material feed part; a rotating drum for adhering the resin particles to the base material; a part for supplying the resin particles to the rotating drum; a drying part for removing water from the base material with the resin particles adhered thereto; and a part for supplying a specific amount of moisture to the base material and/or resin particles, wherein the device has the following features:
the rotating drum has multiple dimples on its surface, and each of the dimples has a ventilation hole at its bottom, through which a gas can blow out from the inside of the rotating drum, the method for manufacturing comprising: adhering the water-absorbent resin particles to a base material followed by drying the water-absorbent resin particles and the base material;
wherein the method fulfills the following conditions
the water content of the base material before spraying is 50 to 500 wt %;
the water content of the water-absorbent resin particles before spraying is 1 to 50 wt %;
the water-absorbent resin particles are adhered to the base material by spraying the water-absorbent resin particles placed in advance in the dimples of the rotating drum onto the base material while making the cloth-like base material be in contact with the surface of the rotating drum;

the outer diameter of the openings of the dimples on the surface of the rotating drum is 1 to 3 times the maximum particle diameter of the water-absorbent resin particles used; and the depth of the dimples on the rotating drum is 0.3 to 2 times the average particle size of the water-absorbent resin particles used, wherein the following conditions are fulfilled:

the weight ratio of water-absorbent resin relative to the total weight of the base material and water-absorbent resin is 65 to 99 wt %;

the water-absorbent resin particles adhering directly to the base material constitute 50 wt % or more of the total water-absorbent resin particles;

the average absorption capacity of the water-absorbent resin particles is greater than 50 g/g the surface strength of the water-absorbent resin particles before being adhered to the base material is 0.1 to 5.5 N; and the amount of residual monomers in the water-absorbent resin is 200 ppm or less.

* * * * *

UNITED STATES PATENT AND TRADEMARK OFFICE
CERTIFICATE OF CORRECTION

PATENT NO. : 8,778,490 B2
APPLICATION NO. : 11/920232
DATED : July 15, 2014
INVENTOR(S) : Tsutomu Akiyama et al.

It is certified that error appears in the above-identified patent and that said Letters Patent is hereby corrected as shown below:

On the Title Page

Column 2, Item [56] (Other Publications), Line 2, Delete "Appiication" and insert -- Application --, therefor.

In the Claims

Column 69, Line 25, In Claim 7, Delete "according claim" and insert -- according to claim --, therefor.

Column 71, Line 19, In Claim 25, Delete "g/g" and insert -- g/g; --, therefor.

Signed and Sealed this
Twenty-eighth Day of October, 2014

Michelle K. Lee
*Deputy Director of the United States Patent and Trademark Office*